US005703076A

United States Patent [19]

Talley et al.

[11] Patent Number: 5,703,076
[45] Date of Patent: *Dec. 30, 1997

[54] RETROVIRAL PROTEASE INHIBITORS

[75] Inventors: John J. Talley; Daniel P. Getman, both of Chesterfield; Ko-Chung Lin, St. Louis; Gary A. DeCrescenzo, St. Peters; Donald J. Rogier, Jr., St. Louis; John N. Freskos, Clayton, all of Mo.

[73] Assignee: G. D. Searle & Co., Skokie, Ill.

[*] Notice: The term of this patent shall not extend beyond the expiration date of Pat. No. 5,475,027.

[21] Appl. No.: 449,966

[22] Filed: May 25, 1995

Related U.S. Application Data

[62] Division of Ser. No. 148,817, Nov. 8, 1993, Pat. No. 5,475,027, which is a continuation of Ser. No. 886,547, May 20, 1992, abandoned, which is a continuation-in-part of Ser. No. 789,644, Nov. 14, 1991, abandoned, which is a continuation-in-part of Ser. No. 615,210, Nov. 19, 1990, abandoned.

[51] Int. Cl.$^6$ .................. C07C 275/18; A61K 31/17
[52] U.S. Cl. .................. 514/237.5; 514/255; 514/330; 514/423; 514/565; 514/588; 514/595; 544/176; 544/391; 546/226; 548/567; 562/49; 562/507; 562/560; 564/47; 564/56; 564/59
[58] Field of Search ................ 564/47, 56, 59; 562/439; 544/176, 391; 546/226; 548/567; 514/237.5, 255, 330, 423, 565, 595, 588

[56] References Cited

U.S. PATENT DOCUMENTS

| H725 | 1/1990 | Gordon | 548/533 |
|---|---|---|---|
| 4,477,441 | 10/1984 | Boger et al. | 424/177 |
| 4,514,391 | 4/1985 | Gordon et al. | 514/2 |
| 4,548,926 | 10/1985 | Matsueda et al. | 514/19 |
| 4,599,198 | 7/1986 | Hoover | 560/333 |
| 4,616,088 | 10/1986 | Ryono et al. | 546/336 |
| 4,668,769 | 5/1987 | Hoover | 530/331 |
| 4,668,770 | 5/1987 | Boger et al. | 530/331 |
| 4,757,050 | 7/1988 | Natarajan et al. | 514/16 |
| 4,963,530 | 10/1990 | Hemmi et al. | 514/19 |
| 4,977,277 | 12/1990 | Rosenberg et al. | 549/215 |
| 5,157,041 | 10/1992 | Handa et al. | 514/314 |

FOREIGN PATENT DOCUMENTS

| 0 104 041 | 3/1984 | European Pat. Off. |
| 0 114 993 | 8/1984 | European Pat. Off. |
| 0 172 347 | 2/1986 | European Pat. Off. |
| 0 223 437 | 5/1987 | European Pat. Off. |
| 0 264 795 | 4/1988 | European Pat. Off. |
| 0 337 714 | 10/1989 | European Pat. Off. |
| 0 342 541 | 11/1989 | European Pat. Off. |
| 0 346 847 | 12/1989 | European Pat. Off. |
| 0 356 223 | 2/1990 | European Pat. Off. |
| 0 389 898 | 10/1990 | European Pat. Off. |
| 0 393 445 | 10/1990 | European Pat. Off. |
| 0 393 457 | 10/1990 | European Pat. Off. |
| 0 402 646 | 12/1990 | European Pat. Off. |
| 2184730 | 7/1987 | United Kingdom |
| 2200115 | 7/1988 | United Kingdom |
| 2209752 | 5/1989 | United Kingdom |
| WO 84/03044 | 8/1984 | WIPO |
| WO93/13066 | 7/1993 | WIPO |

OTHER PUBLICATIONS

Roberts et al, *Science*, 248, 358 (1990).
Krohn et al, *J.Med.Chem.*, 34, 3340 (1991).
Getman et al, *J.Med.Chem.*, 36, 288 (1993).
Reetz et al, *Angew.Chem.Int.Ed.*, 26, 1141–1143 (1987).
J.R. Parikh, *J.Amer.Chem. Soc.*, 89, 5505–5507 (1967).
Erickson et al, *Science*, 249:527–533 (1990).
Drugs of the Future, 1991, 16(3), 210–212.
Meek et al, *Nature*, 343:90–92, (1990).
Pept. Struct. Funct. Proc. Am. Pept. Sym. 8th ed. by V.J. Hunby and D.H. Rich, pp. 511–520 (1983).
McQuade et al, "A Synthetic HIV–1 Protease Inhibitor with Antiviral Activity Arrests HIV–Like Particle Maturation", *Science*, 274, 454 (1990).
Rosenberg et al, *J. Med. Chem.*, 30, 1224–1228 (1987).
Fittkau, *J. Prakt. Chem*, 315, 1037–1044 (1973).

*Primary Examiner*—Bernard Dentz
*Attorney, Agent, or Firm*—Banner & Witcoff, Ltd.

[57] ABSTRACT

Urea-containing hydroxyethylamine compounds are effective as retroviral protease inhibitors, and in particular as inhibitors of HIV protease.

35 Claims, No Drawings

RETROVIRAL PROTEASE INHIBITORS

This is a divisional of application Ser. No. 08/148,817 filed Nov. 8, 1993 now U.S. Pat. No. 5,475,027, which is a continuation of application Ser. No. 07/886,547, filed May 20, 1992 now abandoned, which is a continuation-in-part of application Ser. No. 07/789,644, filed Nov. 14, 1991 now abandoned, which is a continuation-in-part of application Ser. No. 07/615,210, filed Nov. 19, 1990 now abandoned.

BACKGROUND OF THE INVENTION

1. Field of the Invention

The present invention relates to retroviral protease inhibitors and, more particularly, relates to novel compounds and a composition and method for inhibiting retroviral proteases. This invention, in particular, relates to urea-containing hydroxyethylamine protease inhibitor compounds, a composition and method for inhibiting retroviral proteases such as human immunodeficiency virus (HIV) protease and for treatment or prophylaxis of a retroviral infection, e.g., an HIV infection. The subject invention also relates to processes for making such compounds as well as to intermediates useful in such processes.

2. Related Art

During the replication cycle of retroviruses, gag and gag-pol gene products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease that processing of the gag precursor protein is prevented. Thus, attempts have been made to inhibit viral replication by inhibiting the action of retroviral proteases.

Retroviral protease inhibition typically involves a transition-state mimetic whereby the retroviral protease is exposed to a mimetic compound which binds (typically in a reversible manner) to the enzyme in competition with the gag and gag-pol proteins to thereby inhibit replication of structural proteins and, more importantly, the retroviral protease itself. In this manner, retroviral replication proteases can be effectively inhibited.

Several classes of mimetic compounds have been proposed, particularly for inhibition of proteases, such as for inhibition of HIV protease. Such mimetics include hydroxyethylamine isosteres and reduced amide isosteres. See, for example, EP 0346 847; EP O 342,541; Roberts et al, "Rational Design of Peptide-Based Proteinase Inhibitors," Science, 248, 358 (1990); and Erickson et al, "Design Activity, and 2.8 Å Crystal Structure of a $C_2$ Symmetric Inhibitor Complexed to HIV-1 Protease," Science, 249, 527 (1990).

Several classes of mimetic compounds are known to be useful as inhibitors of the proteolytic enzyme renin. See, for example, U.S. Pat. No. 4,599,198; U.K. 2,184,730; G.B. 2,209,752; EP O 264 795; G.B. 2,200,115 and U.S. SIR H725. Of these, G.B. 2,200,115, GB 2,209,752, EP O 264,795, U.S. SIR H725 and U.S. Pat. No. 4,599,198 disclose urea-containing hydroxyethylamine renin inhibitors. However, it is known that, although renin and HIV proteases are both classified as aspartyl proteases, compounds which are effective renin inhibitors generally cannot be predicted to be effective HIV protease inhibitors.

BRIEF DESCRIPTION OF THE INVENTION

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes. The subject compounds are characterized as urea-containing hydroxyethylamine inhibitor compounds.

DETAILED DESCRIPTION OF THE INVENTION

In accordance with the present invention, there is provided a retroviral protease inhibiting compound of the formula:

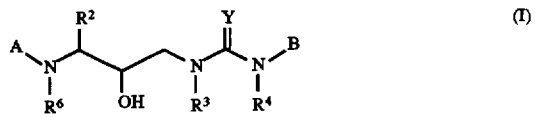

or a pharmaceutically acceptable salt, prodrug or ester thereof
wherein:
A represents R, $R^{13}$ and radicals represented by the formula:

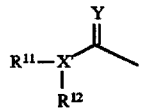

wherein R represents hydrogen and alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxycarbonyl, heteroaroyl, alkyl, aryl, aralkyl, aryloxyalkyl, heteroaryloxyalkyl, hydroxyalkyl, aminocarbonyl, aminoalkanoyl and mono- and disubstituted aminocarbonyl and aminoalkanoyl radicals wherein the substituents are selected from alkyl, aryl, aralkyl, cycloalkyl, cycloalkylalkyl, heteroaryl, heteroaralkyl, heteroalkyl and heterocycloalkylalkyl radicals or in the case of a disubstituted aminoalkanoyl radical, said substitutents along with the nitrogen atom to which they are attached form a heterocycloalkyl or heteroaryl radical;

$R^2$ represents alkyl, aryl, cycloalkyl, cycloalkylalkyl and aralkyl radicals, which radicals are optionally substituted with a group selected from —$OR^9$, —$SR^9$, and halogen radicals, wherein $R^9$ represents hydrogen and alkyl radicals;

$R^3$ represents alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals where said substitutents are selected from alkyl, aryl, aralkyl, cycloalkyl, cycloalkylalkyl, heteroaryl, heteroalkyl, heterocycloalkyl, and heterocycloalkylalkyl radicals or, in the case of a disubstituted aminoalkanoyl radical, said substituents along with the nitrogen atom to which they are attached, form a heterocycloalkyl or a heteroaryl radical;

X' represents O, C(R$^{17}$) where R$^{17}$ represents hydrogen and alkyl radicals, and N;

Y and Y' independently represent O,S and NR$^{15}$ wherein R$^{15}$ represents radicals as defined for R$^3$;

R$^4$, R$^5$, R$^{11}$ and R$^{12}$ independently represent hydrogen and radicals as defined by R$^3$, or R$^4$ and R$^5$, and/or R$^{11}$ and R$^{12}$ together with the nitrogen atom to which they are bonded represent heterocycloalkyl and heteroaryl radicals, or R$^{11}$ and R$^{12}$ together with a carbon atom to which they are attached represent cycloalkyl and aryl radicals;

B represents R$^5$ and radicals represented by the formula:

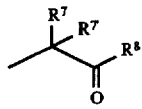

wherein:

R$^7$ and R$^{7'}$ represent radicals as defined for R$^3$ and amino acid side chains selected from valine, isoleuceine, glycine, alanine, allo-isoleucine, asparagine, leucine, glutamine and t-butylglycine;

R$^8$ represents an amide derivative of an amino acid;

R$^{13}$ represents radicals represented by the formula:

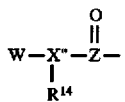

wherein X" is as defined above for X'; Z represents C or S(O), W represents hydrogen and radicals defined by R$^5$, provided that when X" is O, W is absent; R$^{14}$ represents radicals as defined for R$^1$ and R$^3$, or R$^{14}$ and W together with X" form a four to eight-membered cyclic compound wherein the remaining members are carbon, which cyclic compound is saturated or unsaturated; and R$^6$ represents hydrogen and alkyl radicals.

A preferred class of retroviral inhibitor compounds of the present invention are those represented by the formula:

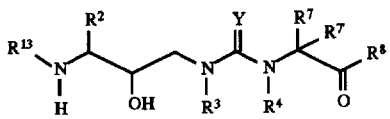

or a pharmaceutically acceptable salt, prodrug or ester thereof wherein Y, R$^2$, R$^3$, R$^4$, R$^7$, R$^{7'}$ and R$^8$, are as defined above; and R$^{13}$ represents radicals as defined for R and radicals of the formula described above wherein Z is carbon and X" is oxygen.

Preferably, R$^3$ represents radicals as defined above which contain no α-branching, e.g., as in an isopropyl radical or a t-butyl radical. The preferred radicals are those which contain a —CH$_2$— moiety between the nitrogen of the urea and the remaining portion of the radical. Such preferred groups include, but are not limited to, benzyl, isobutyl, n-butyl, isoamyl, cyclohexylmethyl and the like.

Another preferred class of compounds are those represented by the formula:

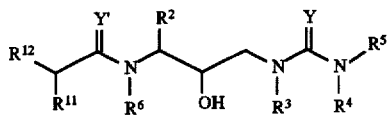

or a pharmaceutically acceptable salt, prodrug or ester thereof wherein X', R$^2$, R$^3$, R$^4$, R$^5$, R$^6$, R$^{11}$, R$^{12}$, Y and Y' are as defined above with respect to Formula II.

Yet another preferred class of compounds are those represented by the formula:

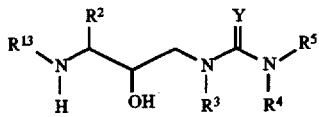

or a pharmaceutically acceptable salt, prodrug or ester thereof wherein Y, R$^2$, R$^3$, R$^4$, R$^5$, and R$^{13}$ are as defined above with respect to Formula II.

As utilized herein, the term "alkyl", alone or in combination, means a straight-chain or branched-chain alkyl radical containing from 1 to about 10, preferably from 1 to about 8, carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radial having one or more double bonds and containing from 2 to about 18 carbon atoms preferably from 2 to about 8 carbon atoms. Examples of suitable alkenyl radicals include ethenyl, propenyl, allyl, 1,4-butadienyl and the like. The term "alkynyl", alone or in combination, means a straight-chain hydrocarbon radical having one or more triple bonds and containing from 2 to about 10 carbon atoms. Examples of alkynyl radicals include ethynyl, propynyl, (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl" means an alkyl radical which contains from about 3 to about 8 carbon atoms and is cyclic. The term "cycloalkylalkyl" means an alkyl radical as defined above which is substituted by a cycloalkyl radical containing from about 3 to about 8, preferably from about 3 to about 6, carbon atoms. Examples of such cycloalkyl radicals include cyclopropyl, cyclobutyl, cyclopentyl, cyclohexyl and the like. The term "aryl", alone or in combination, means a phenyl or naphthyl radical which optionally carries one or more substituents selected from alkyl, alkoxy, halogen, hydroxy, amino and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aralkoxy carbonyl", alone or in combination, means a radical of the formula —C(O)—O-aralkyl in which the term "aralkyl" has the significance given above. An example of an aralkoxycarbonyl radical is benzyloxycarbonyl. The term "aryloxy" means a radical of the formula aryl-o- in which the term aryl has the significance given above. The term "alkanoyl", alone or in combination, means an acyl radical derived from an alkanecarboxylic acid, examples of which include acetyl, propionyl, butyryl, valeryl, 4-methylvaleryl, and the like. The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl,2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl,4-methoxyhydrocinnamoyl, and the like. The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The heterocyclyl or heterocycloalkyl portion of a heterocyclylcarbonyl, heterocyclyloxycarbonyl, heterocyclylalkoxycarbonyl, or heterocyclyalkyl group or the like is a saturated or partially unsaturated monocyclic, bicyclic or tricyclic heterocycle which contains one or more hetero atoms selected from nitrogen, oxygen and sulphur, which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e. =N—) by oxido and which is attached via a carbon atom. The heteroaryl portion of a heteroaroyl, heteroaryloxycarbonyl, or a heteroaralkoxy carbonyl group or the like is an aromatic monocyclic, bicyclic, or tricyclic heterocycle which contains the hetero atoms and is optionally substituted as defined above with respect to the definition of heterocyclyl. Examples of such heterocyclyl and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, pyrazinyl, pyrimidinyl, furyl, thienyl, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl (e.g., 1,2,3,4-tetrahydro-1-oxoisoquinolinyl, etc.), quinoxalinyl, β-carbolinyl, 2-benzofurancarbonyl, 2-benzimidazolyl and the like. The term "cycloalkylalkoxycarbonyl" means an acyl group derived from a cycloalkylalkoxycarboxylic acid of the formula cycloalkylalkyl-O-COOH wherein cycloalkylalkyl has the significance given above. The term "aryloxyalkanoyl" means an acyl radical of the formula aryl-O-alkanoyl wherein aryl and alkanoyl have the significance given above. The term "heterocyclyloxycarbonyl" means an acyl group derived from heterocyclyl-O-COOH wherein heterocyclyl is as defined above. The term "heterocyclylalkanoyl" is an acyl radical derived from a heterocyclyl-substituted alkane carboxylic acid wherein heterocyclyl has the significance given above. The term "heterocyclylalkoxycarbonyl" means an acyl radical derived from a heterocyclyl-substituted alkane-O-COOH wherein heterocyclyl has the significance given above. The term "heteroaryloxycarbonyl" means an acyl radical derived from a carboxylic acid represented by heteroaryl-O-COOH wherein heteroaryl has the significance given above. The term "aminoalkanoyl" means an acyl group derived from an amino-substituted alkanecarboxylic acid wherein the amino group can be a primary, secondary or tertiary amino group containing substituents selected from hydrogen, and alkyl, aryl, aralkyl, cycloalkyl, cycloalkylalkyl radicals and the like. The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, and alkyl, aryl, aralkyl, cycloalkyl, cycloalkylalkyl radicals and the like. The term "halogen" means fluorine, chlorine, bromine or iodine. The term "leaving group" generally refers to groups readily displaceable by a nucleophile, such as an amine, a thiol or an alcohol nucleophile. Such leaving groups are well known and include carboxylates, N-hydroxysuccinimide, N-hydroxybenzotriazole, halides, triflates, tosylates —OR and —SR and the like. Preferred leaving groups are indicated herein where appropriate.

Procedures for preparing the compounds of Formula I are set forth below. It should be noted that the general procedure is shown as it relates to preparation of compounds having the specified stereochemistry, for example, wherein the stereochemistry about the hydroxyl group is designated as (R). However, such procedures are generally applicable, as illustrated in Example 45, to those compounds of opposite configuration, e.g., where the stereochemistry about the hydroxyl group is (S).

Preparation of Compounds of Formula I

The compounds of the present invention represented by Formula I above can be prepared utilizing the following general procedure. An N-protected chloroketone derivative of an amino acid having the formula:

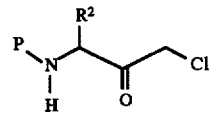

wherein P represents an amino protecting group, and $R^2$ is as defined above, is reduced to the corresponding alcohol utilizing an appropriate reducing agent. Suitable amino protecting groups are well known in the art and include carbobenzoxy, butyryl, t-butoxycarbonyl, acetyl, benzoyl and the like. A preferred amino protecting group is carbobenzoxy. A preferred N-protected chloroketone is N-benzyloxycarbonyl-L-phenylalanine chloromethyl ketone. A preferred reducing agent is sodium borohydride. The reduction reaction is conducted at a temperature of from −10° C. to about 25° C., preferably at about 0° C., in a suitable solvent system such as, for example, methanol tetrahydrofuran, and the like. The N-protected chloroketones are commercially available from Bachem, Inc., Torrance, Calif. Alternatively, the chloroketones can be prepared by the procedure set forth in S. J. Fittkau, J. Prakt. Chem., 315, 1037 (1973), and subsequently N-protected utilizing procedures which are well known in the art.

The resulting alcohol is then reacted, preferably at room temperature, with a suitable base in a suitable solvent system to produce an N-protected amino epoxide of the formula:

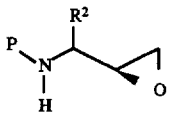

wherein P and R² are as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Alternatively, a protected amino epoxide can be prepared starting with an L-amino acid which is reacted with a suitable protecting group in a suitable solvent to produce an amino-protected L-amino acid ester of the formula:

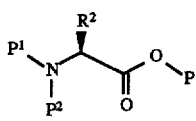

wherein P, P¹ and P² independently represent hydrogen and amino-protecting groups as defined above with respect to P, provided that P¹ and P² are not both hydrogen; and R² is as defined above.

The amino-protected L-amino acid ester is then reduced, to the corresponding alcohol. For example, the amino-protected L-amino acid ester can be reduced with diisobutylaluminum hydride at –78° C. in a suitable solvent such as toluene. The resulting alcohol is then converted, by way of a Swern Oxidation, to the corresponding aldehyde of the formula:

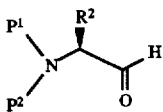

wherein P¹, P² and R² are as defined above. Thus, a dichloromethane solution of the alcohol is added to a cooled (–75° to –68° C.) solution of oxalyl chloride in dichloromethane and DMSO in dichloromethane and stirred for 35 minutes.

The aldehyde resulting from the Swern Oxidation is then reacted with a halomethyllithium reagent, which reagent is generated in situ by reacting an alkyllithium or arylithium compound with a dihalomethane represented by the formula X¹CH₂X² wherein X¹ and X² independently represent I, Br or Cl. For example, a solution of the aldehyde and chloroiodomethane in THF is cooled to –78° C. and a solution of n-butyllithium in hexane is added. The resulting product is a mixture of diastereomers of the corresponding amino-protected epoxides of the formulas:

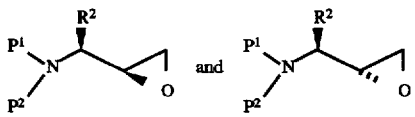

The diastereomers can be separated by chromatography or, alternatively, once reacted in subsequent steps the diastereomeric products can be separated.

The amino epoxide is then reacted, in a suitable solvent system, with an equal amount, or preferably an excess of, a desired amine of the formula:

wherein R³ is hydrogen or is as defined above. The reaction can be conducted over a wide range of temperatures, e.g., from about 10° C. to about 100° C., but is preferably, but not necessarily, conducted at a temperature at which the solvent begins to reflux. Suitable solvent systems include those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula R³NH₂ include benzyl amine, isobutylamine, n-butyl amine, isopentyl amine, isoamylamine, cyclohexanemethyl amine, naphthylene methyl amine and the like. The resulting product is a 3-(N-protected amino)-3-(R²)-1-(NHR³)-propan-2-ol derivative (hereinafter referred to as an amino alcohol) can be represented by the formula:

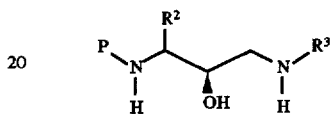

wherein P, R² and R³ are as described above.

For producing compounds of Formula I wherein R⁵ is hydrogen, the resulting amino alcohol described above is then reacted, in a suitable solvent system, with an isocyanate of the formula R⁴NCO wherein R⁴ is as defined above. Where Y in Formula I above is sulfur, the resulting amino alcohol is reacted with an isothiocyanate of the formula R⁴NCS under similar conditions. Suitable solvent systems include tetrahydrofuran, methylene chloride, and the like and mixtures thereof. The resulting product is a urea derivative of the amino alcohol or the corresponding sulfur analog thereof and can be represented by the formula:

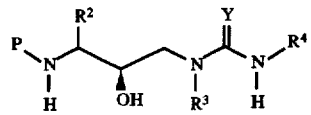

wherein P, Y, R², R³ and R⁴ are as defined above. The isocyanates of the formula R⁴NCO can be prepared by the reaction of an amine (R³NH₂) with phosgene, triphosgene, carbodiimidazole, or carbonate ((RO)₂CO) under conditions well-known in the art. The isothiocyanates of the formula R₄NCS can be prepared by similar procedures, e.g., reaction of the amine with thiophosgene, which are also well known in the art. In addition, the isocyanates and isothiocyanates are commercially available from Aldrich Chemical Company.

For preparing compounds of Formula I wherein R⁵ is other than hydrogen, the resulting amino alcohol described above is then reacted, in a suitable solvent system, with a compound represented by the formula:

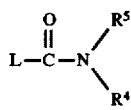

wherein R⁴ and R⁵ are as described above and L represents a leaving group such as a halide, e.g., chloride, imidazole radical, the radical p—NO₂—(C₆H₄)—O—, and the like. A preferred compound represented by this formula is a carbamoyl chloride. The corresponding sulfur analogs can be utilized where Y of Formula I is S.

The urea derivative of the amino alcohol and the corresponding sulfur analog can be represented by the formula:

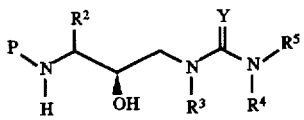

Following preparation of the urea derivative, or corresponding analogs wherein Y is S, the amino protecting group P can be removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a .suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative.

The amine salt derivative can then be reacted with a carboxylate represented by the formula:

wherein R is as defined above and L is an appropriate leaving group such as a halide. A solution of the free amine (or amine acetate salt) and about 1.0 equivalent of the carboxylate are mixed in an appropriate solvent system and optionally treated with up to five equivalents of a base such as, for example, N-methylmorpholine, at about room temperature. Appropriate solvent systems include tetrahydrofuran, methylene chloride or N,N-dimethylformamide, and the like, including mixtures thereof.

Preparation of Compounds of Formula II

The compounds of the present invention represented by Formula II can be prepared utilizing the following general procedure. Following the procedure for preparing compounds of Formula I, an N-protected amino epoxide is reacted with an excess of a desired amine. The resulting product is the amino alcohol described above which is subsequently reacted with a desired amino acid ester hydrochloride in a suitable solvent system and in the presence of a coupling agent to produce a compound of the formula:

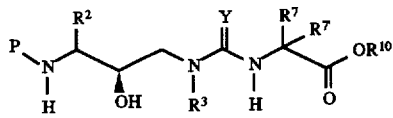

wherein P, Y, $R^2$, $R^3$, $R^7$ and $R^{7'}$ are as defined above and $R^{10}$ is an alkyl radical derived from the amino acid ester. Preferred solvent systems include chloroform, methylene chloride, tetrahydrofuran, and the like, including mixtures thereof. Preferred coupling agents include carbonyldiimidazole, phosgene, triphosgene, and the like.

The compounds of Formula II can also be prepared by well known peptide coupling techniques, two of which are illustrated in the Examples hereof, and by a novel Curtius Rearrangement technique. The Curtius Rearrangement technique involves treatment of a statine derivative of the formula:

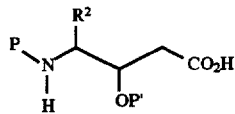

wherein P and $R^2$ are as defined above and P' is a suitable hydroxy protecting group such as a silyl ether, preferably a t-butyldimethylsilyl group, with one equivalent of diphenoxylphosphoryl azide $(PhO)_2 PON_3$ and triethylamine to form an acyl azide followed by heating in an inert solvent, such as warm toluene, preferably at about 80 degrees C. for about three hours, to afford an isocyanate derivative. The isocyanate derivative is then trapped with an amino acid ester derivative and the protecting group removed by treatment with a fluoride source, such as tetra-n-butylammonium fluoride to provide a compound of the formula:

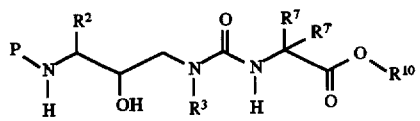

wherein P, $R^2$, $R^3$, $R^7$, $R^{7'}$ and $R^{10}$ are as defined above. The resulting compound is then reacted with an amino acid, and then deprotected and reacted with a carboxylate as set forth for preparing compounds of Formula II.

Preparation of Compounds of Formula III

The compounds of the present invention represented by Formula III can be prepared by the following generalized procedure. Following the procedure for preparing compounds of Formula I above, the urea derivative, or corresponding sulfur analog thereof, of an amino alcohol is prepared having the formula:

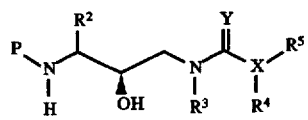

wherein P, Y, $R^2$, $R^3$, $R^4$, and $R^5$ are as defined above. The amino protecting group is then removed following the procedure as outlined above for preparing compounds of Formula I and reacted again with either an isocyanate of the formula $R^{11}$ NCO, an isothiocyanate of the formula $R^{11}$NCS or a compound of the formula:

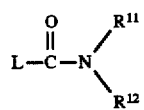

wherein $R^{11}$, $R^{12}$ and L are as defined above to form the bis-urea derivative or C or O analog thereof represented by the formula:

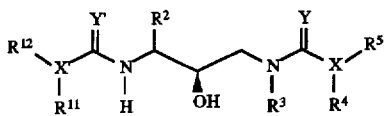

wherein X', Y, Y', R², R³, R⁴, R⁵, R¹¹ and R¹² are as defined above.

Preparation of Compounds of Formula IV

To prepare compounds of Formula IV, the above-described urea derivative, or sulfur analog, is prepared and the amino-protecting group removed following the procedure for preparing compounds of Formula I. The urea derivative or analog thereof is then reacted with an acylating agent, such as an isocyanate, isothiocyanate, acyl halide, sulfonyl halide, carbamoyl halide, chloroformate and the like according to the procedures described above and/or by procedures which are well known in the art.

It is contemplated that for preparing compounds of the Formulas having R⁶, the compounds can be prepared following the procedure set forth above and, prior to coupling the urea derivative or analog thereof, e.g. coupling, to the amino acid PNH(CH₂),CH(R¹)COOH, carried through a procedure referred to in the art as reductive amination. Thus, a sodium cyanoborohydride and an appropriate aldehyde R⁶C(O)H or ketone R⁶C(O)R⁶ can be reacted with the urea derivative compound or appropriate analog at room temperature in order to reductively aminate any of the compounds of Formulas I–VI. It is also contemplated that where R³ of the amino alcohol intermediate is hydrogen, the inhibitor compounds of the present invention wherein R³ is an alkyl radical, or other substituent wherein the α-C contains at least one hydrogen, can be prepared through reductive amination of the final product of the reaction between the amino alcohol and the amine or at any other stage of the synthesis for preparing the inhibitor compounds.

Contemplated equivalents of the general formulas set forth above for the antiviral compounds and derivatives as well as the intermediates are compounds otherwise corresponding thereto and having the same general properties wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Examples 1–45 illustrate compounds outside the scope of the present invention, but the general procedures described therein can be utilized to prepare compounds of the present invention as shown in Examples 46–52 which illustrate compounds of the present invention.

All reagents were used as received without purification. All proton and carbon NMR spectra were obtained on either a Varian VXR-300 or VXR-400 nuclear magnetic resonance spectrometer.

EXAMPLE 1

Preparation of [1S-[1R*(R*), 2S*]]- N¹[3-[[[(1,1-dimethylethyl)amino]carbonyl](2-methylpropyl)amino]-2-hydroxy-1-(phenylmethyl)propyl]-2-[(2-quinolinylcarbonyl)amino]-butanediamide Part A. To a solution of 75.0 g (0.226 mol) of N-benzyloxycarbonyl-L-phenylalanine chloromethyl ketone in a mixture of 807 mL of methanol and 807 mL of tetrahydrofuran at −2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1 L). The solution was washed sequentially with 1M potassium hydrogen sulfate, saturated sodium bicarbonate and then saturated sodium chloride solutions. After drying over anhydrous magnesium sulfate and filtering, the solution was removed under reduced pressure. To the resulting oil was added hexane (approx. 1 L) and the mixture warmed to 60° C. with swirling. After cooling to room temperature, the solids were collected and washed with 2 L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150°–151° C. and M+Li+=340.

Part B. To a solution of 6.52 g (0.116 mol, 1.2 equiv.) of potassium hydroxide in 968 mL of absolute ethanol at room temperature, was added 32.3 g (0.097 mol) of N-CBZ-3(S)-amino-1-chloro-4-phenyl-2(S)-butanol. After stirring for fifteen minutes, the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl-3(S)-amino-1,2(S)-epoxy-4-phenylbutane, mp 102°–103° C. and MH+298.

Part C. A solution of N-benzyloxycarbonyl 3(S)-amino-1,2-(S)-epoxy-4-phenylbutane (1.00 g, 3.36 mmol) and isobutylamine (4.90 g, 67.2 mmol, 20 equiv.) in 10 mL of isopropyl alcohol was heated to reflux for 1.5 hours. The solution was cooled to room temperature, concentrated in vacuo and then poured into 100 mL of stirring hexane whereupon the product crystallized from solution. The product was isolated by filtration and air dried to give 1.18 g, 95% of N=[[3(S)-phenylmethylcarbamoyl)amino-2(R)-hydroxy-4-phenylbutyl]N-[(2-methylpropyl)]amine mp 108.0°–109.5° C., MH+ m/z=371.

Part D. A solution of [2(R), 3(S)]-N-[[3-(phenylmethylcarbamoyl)amino]-2-hydroxy-4-phenylbutyl] N-[(2-methylpropyl)]amine in 10 ml of tetrahydrofuran was treated with tert-butylisocyanate (267 mg, 2.70 mmol) at room temperature for 5 minutes. The solvent was removed in vacuo and replaced with ethyl acetate. The ethyl acetate solution was washed with 5% citric acid, water, and brine, dried over anhydrous $MgSO_4$, filtered and concentrated in vacuo to give 1.19 g, 97% of [2(R), 3(S)]-N-[[3-(phenylmethylcarbamoyl)amino]-2-hydroxy-4-phenyl]-1-[(2-methylpropyl)]amino-2-(1,1-dimethyl)amino]carbonyl] butane, MH+ m/z-470.

Part E. A solution of (1.00 g, 2.21 mmol) [2(R), 3(S)]-N-[[3-(phenylmethylcarbamoyl)amino]-2-hydroxy-4-phenyl]-1-[(2-methylpropyl)]amino-1-(1,1-dimethylethyl)amino] carbonyl]butane in 20 mL of methanol was hydrogenated over 10% palladium-on-carbon for 4 hours to give [2(R), 3(S)]-N-[[3-amino]-2-hydroxy-4-phenyl]-1-[(2-methylpropyl)amino-1-(1,1-dimethylethyl)amino]carbonyl] butane 720 mg, 97%.

Part F. A solution of N-Cbz-L-asparagine (602 mg, 2.26 mmol) and N-hydroxybenzotriazole (493 mg, 3.22 mmol) in 2 mL of dimethylformamide was cooled to 0° C. and treated with EDC (473 mg, 2.47 mmol). The solution was allowed to stir at 0° C. for 20 minutes and then treated with [2(R), 3(S)]-N-[[3-amino]-2-hydroxy-4-phenyl]-1-[(2-methylpropyl)]amino-1-(1,1-dimethylethyl)amino] carbonyl]butane (720 mg, 2.15 mmol) in 1 mL of dimethylformamide. The solution was allowed to warm to room temperature and held at this temperature for 7 hours. The reaction mixture was then poured into 100 mL of 60% saturated aqueous sodium bicarbonate whereupon a white precipitate formed that was isolated by filtration. The filter cake was washed with water, 5% aqueous citric acid, water and then dried in vacuo to give 1.04 g, 83% of [1S-[1R* (R*), 2S*]]- $N^1$[3-[[[(1,1-dimethylethyl)amino]carbonyl](2-methylpropyl)amino]-2-hydroxy-1-(phenylmethyl)propyl]-2-[(phenylmethylcarbamoyl)amino]-butanediamide, mp. 164.0°–166.5° C., MH+m/z=584.

Part G. A solution of [1S-[1R*(R*), 2S*]]- $N^1$[3-[[[(1,1-dimethylethyl)amino]carbonyl](2-methylpropyl)amino]-2-hydroxy-1-(phenylmethyl)propyl]-2-[(phenylmethylcarbamoyl)amino]-butanediamide (1.00 g, 1.72 mmol) in 10 mL of methanol was hydrogenated over 10% palladium-on-carbon for 4 hours to give [1S-[1R*(R*), 2S*]]-$N^1$[3-[[[(1,1-dimethylethyl)amino]carbonyl](2-methylpropyl)amino]-2-hydroxy-1-(phenylmethyl)propyl]-2-amino]-butanediamide, 784 mg, 99%.

Part H. A mixture of [1S-[1R*(R*), 2S*]]- $N^1$[3-[[[(1,1-dimethylethyl)amino]carbonyl](2-methylpropyl)amino]-2-hydroxy-1-(phenylmethyl)propyl]-2-amino]-butanediamide, (784 mg, 1.70 mmol), 2-quinoline carboxylic acid N-hydroxysuccinimide ester (459 mg, 1.70 mmol), N-methylmorpholine (343 mg, 3.40 mmol) in 5 mL of dichloromethane was stirred at room temperature for 15 minutes. The solvent was removed in vacuo and replaced with ethyl acetate and the solution washed with 5% aqueous citric acid, saturated aqueous sodium bicarbonate, brine, dried over anhydrous $MgSO_4$, filtered and concentrated in vacuo. The crude product was recrystallized from acetone/ hexane to give 790 mg, 77% of [1S-[1R*(R*), 2S*]]-$N^1$[3-[[[(1,1-dimethylethyl)amino]carbonyl](2-methylpropyl)amino]-2-hydroxy-1-(phenylmethyl)propyl]-2-[(2-quinolinylcarbonyl)amino]-butanediamide, mp 107.0°–109.8° C., MH+=605.

EXAMPLE 2

The procedure described in Example 1, part C-H, was used to prepare [1S-[1R*(R*), 2S*]]- $N^1$[3-[[[(1,1-dimethylethyl)amino]carbonyl](3-methylbutyl)amino]-2-hydroxy-1-(phenylmethyl)propyl]-2-[(2-quinolinylcarbonyl)amino]-butanediamide.

a) From the reaction of 1.06 g (3.56 mmol) of N-benzyloxycarbonyl 3(S)-amino-1,2-(S)-epoxy-4-phenylbutane and 6.25 g (71.7 mmol) of isoamylamine, one obtains 1.27 g (92%) of [2(R), 3(S)]-N-[[3-(phenylmethylcarbamoyl)amino]-2-hydroxy-4-phenylbutyl] N-[(3-methylbutyl)]amine, mp 130°–132° C. and MH* 385. This amine (400 mg, 1.04 mmol) was then reacted with tert-butylisocyanate (110 mg, 1.11 mmol) to afford 500 mg (100%) of [2(R), 3(S)]-N-[[3-(phenylmethylcarbamoyl) amino]-2-hydroxy-4-phenyl]-1-[(3-methylbutyl)]amino-1-(1,1-dimethylethyl)amino]carbonyl]butane; as an oil, MH+484.

b) The CBZ protected compound (530 mg, 1.10 mmol) was then deprotected by hydrogenation over 10% palladium-on-carbon and the resulting free amine coupled with N-CBZ-L-asparagine (377 mg, 1.42 mmol) in the presence of N-hydroxybenzotriazole (290 mg, 2.15 mmol) and EDC (300 mg, 1.56 mmol) to yield 430 mg (53%) of [1S-[1R* (R*), 2S*]]- $N^1$[3-[[[(1,1-dimethylethyl)amino]carbonyl](3-methylbutyl)amino]-2-hydroxy-1-(phenylmethyl)propyl]-2-[(phenylmethylcarbamoyl)amino]-butanediamide, mp 148°–151° C. (dec) and MH+598. This compound (370 mg, 0.619 mmol) was then deprotected by hydrogenation over 10% palladium-on-carbon and the resulting free amine coupled with 2-quinolinecarboxylic acid N-hydroxysuccinimide ester (193 mg, 0.714 mmol), in the presence of N-methylmorpholine, to afford 310 mg (70%) of pure [1S-[1R*(R*), 2S*]]- $N^1$[3-[[[(1,1-dimethylethyl)amino] carbonyl](3-methylbutyl)amino]-2-hydroxy-1-(phenylmethyl)propyl]-2-[(2-quinolinylcarbonyl)amino]-butanediamide; mp 93.5°–95.5° C. and MH+619.

EXAMPLE 3

The procedure described in Example 1, part C-H, was used to prepare [1S-[1R*(R*), 2S*]]- $N^1$[3-[[[(1,1-dimethylethyl)amino]carbonyl]2-napthylmethyl)amino]-2-hydroxy-1-(phenylmethyl)propyl]-2-[(2-quinolinylcarbonyl)amino]-butanediamide.

a) From the reaction of 1.80 g (6.05 mmol) of N-benzyloxycarbonyl 3(S)-amino-1,2-(S)-epoxy-4-phenylbutane and 1.15 g (7.31 mmol) of 2-(aminomethyl) naphthalene, one obtains 2.11 g (77%) of [2(R), 3(S)]-N-[ [3-(phenylmethylcarbamoyl)amino]-2-hydroxy-4-phenylbutyl]N-[(2-napthylmethyl)]amine, MH+455. This amine (366.8 mg, 0.807 mmol) was then reacted with tert-butylisocyanate (66.4 mg, 0.67 mmol) to afford 350.0 mg (94%) of [2(R), 3(S)]-N-[[3-(phenylmethylcarbamoyl) amino]-2-hydroxy-4-phenyl]-1-[(2-napthylmethyl)]amino-1-(1,1-dimethylethyl)amino]carbonyl]butane; as an oil, MH+554.

b) The CBZ protected compound (330 mg, 0.596 mmol) was then deprotected by hydrogenation over 10% palladium-on-carbon and the resulting free amine coupled with N-CBZ-L-asparagine (165.1 mg, 0.62 mmol) in the presence of N-hydroxybenzotriazole (142.3 mg, 0.93 mmol) and EDC (130.7 mg, 0.68 mmol) to yield 161.7 mg (41%) of [1S-[1R*(R*), 2S*]]- $N^1$[3-[[[(1,1-dimethylethyl)amino] carbonyl](2-napthylmethyl)amino]-2-hydroxy-1-(phenylmethyl)propyl]-2-[(phenylmethylcarbamoyl)amino] -butanediamide; mp 151°–152° C. (dec) and MH+668. This compound (91.0 mg, 0.136 mmol) was then deprotected by hydrogenation over 10% palladium-on-carbon and the resulting free amine coupled with 2-quinolinecarboxylic acid N-hydroxysuccinimide ester (36.8 mg, 0.136 mmol), in the presence of N-methylmorpholine, to afford 65.8 mg (70%) of pure [1S-[1R*(R*), 2S*]]- $N^1$[3-[[[(1,1-dimethylethyl)amino]carbonyl](2-napthylmethyl)amino]-2- hydroxy-1-(phenylmethyl)propyl]-2-[(2-quinolinylcarbonyl)amino]-butanediamide; mp 119°–120° C. and MH+689.

EXAMPLE 4

The procedure described in Example 1, part C-H, was used to prepare [1S-[1R*(R*), 2S*]]- N$^1$[3-[[[(1,1-dimethylethyl)amino]carbonyl](2-phenylethyl)amino]-2-hydroxy-1-(phenylmethyl)propyl]-2-[(2-quinolinylcarbonyl)amino]-butanediamide.

a) From the reaction of 1.00 g (3.36 mmol) of N-benzyloxycarbonyl 3(S)-amino-1,2-(S)-epoxy-4-phenylbutane and 8.19 g (67.0 mmol) of 2-phenethyl amine, one obtains 1.10 g (79%) of [2(R), 3(S)]-N-[[3-(phenylmethylcarbamoyl)amino]-2-hydroxy-4-phenylbutyl] N-[(2-phenylethyl)]amine, mp 137°–138° C. and MH+419. This amine (750 mg, 1.79 mmol) was then reacted with tert-butylisocyanate (178 mg, 1.79 mmol) to afford 897 mg *(97%) of [2(R), 3(S)]-N-[[3-(phenylmethylcarbamoyl)amino]-2-hydroxy-4-phenyl]-1-[(2-phenylethyl)]amino-1-(1,1-dimethylethyl)amino]carbonyl]butane; as an oil, MH+518.

b) The CBZ protected compound (897 mg, 1.73 mmol) was then deprotected by hydrogenation over 10% palladium-on-carbon and the resulting free amine coupled with N-CBZ-L-asparagine (620.7 mg, 2.33 mmol) in the presence of N-hydroxybenzotriazole (509.5 mg, 3.33 mmol) and EDC (488.0 mg, 2.55 mmol) to yield 1.00 g (92%) of [1S-[1R*(R*), 2S*]]- N$^1$[3[[[(1,1-dimethylethyl)amino]carbonyl](2-phenylethyl)amino]-2-hydroxy-1-(phenylmethyl)propyl]-2-[(phenylmethylcarbamoyl)amino]-butanediamide; mp 145 (dec) and MH+632. This compound (860 mg, 1.36 mmol) was then deprotected by hydrogenation over 10% palladium-on-carbon and the resulting free amine coupled with 2-quinolinecarboxylic acid N-hydroxysuccinimide ester (338 mg, 1.25 mmol), in the presence of N-methylmorpholine, to afford 450.4 mg (55%) of pure [1S-[1R*(R*), 2S*]]- N$^1$[3[[[(1,1-dimethylethyl)amino]carbonyl](2-phenylethyl)amino]-2-hydroxy-1-(phenylmethyl)propyl]-2-[(2-quinolinylcarbonyl)amino]-butanediamide; mp 139°–140° C. and MH+653.

EXAMPLE 5

The procedure described in Example 1, part C-H, was used to prepare [1S-[1R*(R*), 2S*]]- N$^1$[3-[[[(1,1-dimethylethyl)amino]carbonyl](2,2-dimethylpropyl)amino]-2-hydroxy-1-(phenylmethyl)propyl]-2-[(2-quinolinylcarbonyl)amino]-butanediamide.

a) From the reaction of 1.00 g (3.36 mmol) of N-benzyloxycarbonyl 3(S)-amino-1,2-(S)-epoxy-4-phenylbutane and 7.9 mL (approx. 67 mmol) of neopentyl amine, one obtains 0.69 g (49%) of [2(R), 3(S)]-N-[[3-(phenylmethylcarbamoyl)amino]-2-hydroxy-4-phenylbutyl] N-[(2,2-dimethylpropyl)]amine, MH+385. This amine (686 mg, 1.78 mmol) was then reacted with tert-butylisocyanate (180 mg, 1.78 mmol) to afford 860 mg (100%) of [2(R), 3(S)]-N-[[3-(phenylmethylcarbamoyl)amino]-2-hydroxy-4-phenyl]-1-[(2,2-dimethylpropyl)]amino-1-(1,1-dimethylethyl)amino]carbonyl]butane; MH+484.

b) The CBZ protected compound (860 mg, 1.78 mmol) was then deprotected by hydrogenation over 10% palladium-on-carbon and the resulting free amine coupled with N-CBZ-L-asparagine (471 mg, 1.77 mmol) in the presence of N-hydroxybenzotriazole (406 mg, 2.66 mmol) and EDC (374 mg, 1.95 mmol) to yield 326 mg (34%) of [1S-[R*(R*), 2S*]]- N$^1$[3-[[[(1,1-dimethylethyl)amino]carbonyl](2,2-dimethylpropyl)amino]-2-hydroxy-1-(phenylmethyl) propyl]-2-[(phenylmethylcarbamoyl)amino]-butanediamide; mp 177°–178° C. and MH+598. This compound (245 mg, 0.41 mmol) was then deprotected by hydrogenation over 10% palladium-on-carbon and the resulting free amine coupled with 2-quinolinecarboxylic acid N-hydroxy- succinimide ester (111 mg, 0.41 mmol), in the presence of N-methylmorpholine, to afford 150 mg (59%) of pure [1S-[R*(R*), 2S*]]- N$^1$[3-[[[(1,1-dimethylethyl)amino]carbonyl](2,2-dimethylpropyl)amino]-2-hydroxy-1-(phenylmethyl)propyl]-2-[(2-quinolinylcarbonyl)amino]-butanediamide; mp 115°–117° C. and MH+619.

EXAMPLE 6

The procedure described in Example 1, part C-H, was used to prepare [1S-[R*(R*), 2S*]]- N$^1$[3-[[[(1,1-dimethylethyl)amino]carbonyl](4-methoxyphenylmethyl)amino]-2-hydroxy-1-(phenylmethyl)propyl]-2-[(2-quinolinylcarbonyl)amino]-butanediamide;

a) From the reaction of 1.00 g (3.36 mmol) of N-benzyloxycarbonyl 3(S)-amino-1,2-(S)-epoxy-4-phenylbutane and 9.2 g (67 mmol) of 4-methoxybenzyl amine, one obtains 1.12 g (76%) of [2(R), 3(S)]-N-[[3-(phenylmethylcarbamoyl)amino]-2-hydroxy-4-phenylbutyl] N-[(4-methoxyphenylmethyl)]amine, MH+435. This amine (1.12 g, 2.58 mmol) was then reacted with tert-butylisocyanate (260 mg, 2.58 mmol) to afford 1.35 g (98%) of [2(R), 3(S)]-N-[[3-(phenylmethylcarbamoyl)amino]-2-hydroxy-4-phenyl]-1-[(4-methoxyphenylmethyl)]amino-1-(1,1-dimethylethyl)amino]carbonyl]butane; MH+534.

b) The CBZ protected compound (1.35 g, 2.53 mmol) was then deprotected by hydrogenation over 10% palladium-on-carbon and the resulting free amine coupled with N-CBZ-L-asparagine (684 mg, 2.57 mmol) in the presence of N-hydroxybenzotriazole (590 mg, 3.85 mmol) and EDC (543 mg, 2.83 mmol) to yield 442 mg (29%) of [1S-[1R*(R*), 2S*]]- N$^1$[3-[[[(1,1-dimethylethyl)amino]carbonyl](4-methoxyphenylmethyl)amino]-2-hydroxy-1-(phenylmethyl) propyl]-2-[phenylmethylcarbamoyl)amino]-butanediamide; mp 175° C. (dec) and MH+648. This compound (345 mg, 0.53 mmol) was then deprotected by hydrogenation over 10% palladium-on-carbon and the resulting free amine coupled with 2-quinolinecarboxylic acid N-hydroxy-succinimide ester (118 mg, 0.44 mmol), in the presence of N-methylmorpholine, to afford 108 mg (31%) of pure [1S-[1R*(R*), 2S*]]- N$^1$[3-[[[(1,1-dimethylethyl)amino] carbonyl](4-methoxyphenylmethyl)amino]-2-hydroxy-1-(phenylmethyl)propyl]-2-[(2-quinolinylcarbonyl)amino]-butanediamide; mp 220° C. (dec) and MLi+675.

EXAMPLE 7

The procedure described in Example 1, part C-H, was used to prepare [1S-[1R*(R*), 2S*]]- N$^1$[3-[[[(1,1-dimethylethyl)amino]carbonyl](n-butyl)amino]-2-hydroxy-1-(phenylmethyl)propyl]-2-[(2-quinolinylcarbonyl)amino]-butanediamide.

a) From the reaction of 1.48 g (5.0 mmol) of N-benzyloxycarbonyl 3(S)-amino-1,2-(S)-epoxy-4-phenylbutane and 7.314 g (100.0 mmol) of n-butyl amine, one obtains 1.50 g (80%) of [2(R), 3(S)]-N-[[3-(phenylmethylcarbamoyl)amino]-2-hydroxy-4-phenylbutyl] N-[n-butyl)]amine. This amine (1.48 g, 4.0 mmol) was then reacted with tert-butylisocyanate (396 mg, 4.0 mmol) to afford 1.87 g (100%) of [2(R), 3(S)]-N-[[3-(phenylmethylcarbamoyl)amino]-2-hydroxy-4-phenyl]-1-[

(n-butyl)]amino-1-(1,1-dimethylethyl)amino]carbonyl] butane as an oil.

b) The CBZ protected compound (1.87 g, 4.0 mmol) was then deprotected by hydrogenation over 10% palladium-on-carbon and the resulting free amine coupled with N-CBZ-L-asparagine (1.05 g, 3.96 mmol) in the presence of N-hydroxybenzotriazole (535 mg, 7.9 mmol) and EDC (759 mg, 3.96 mmol) to yield 1.75 g (76%) of [1S-[1R*(R*), 2S*]]- N¹[3-[[[(1,1-dimethylethyl)amino]carbonyl](n-butyl)amino]-2-hydroxy-1-(phenylmethyl)propyl]-2-[(phenylmethylcarbamoyl)amino]-butanediamide; mp 166°–167° C. and MH+584.

EXAMPLE 8

The procedure described in Example 1, part C-H, was used to prepare [1S-[1R*(R*), 2S*]]- N¹[3-[[[(1,1-dimethylethyl)amino]carbonyl](phenylmethyl)amino]-2-hydroxy-1-(phenylmethyl)propyl]-2-[(2-quinolinylcarbonyl)amino]-butanediamide.

a) From the reaction of 1.48 g (5.0 mmol) of N-benzyloxycarbonyl 3(S)-amino-1,2-(S)-epoxy-4-phenylbutane and 10.68 g (100.0 mmol) of benzyl amine, one obtains 1.88 g (95%) of [2(R), 3(S)]-N-[[3-(phenylmethylcarbamoyl)amino]-2-hydroxy-4-phenylbutyl] N-[(phenylmethyl)]amine. This amine (1.88 g, 4.65 mmol) was then reacted with tert-butylisocyanate (460.0 mg, 4.6 mmol) to afford 2.24 g (96%) of [2(R), 3(S)]-N-[[3-(phenylmethylcarbamoyl)amino]-2-hydroxy-4-phenyl]-1-[(phenylmethyl)]amino-1-(1,1-dimethylethyl)amino] carbonyl]butane.

b) The CBZ protected compound (2.22 g, 4.4 mmol) was then deprotected by hydrogenation over 10% palladium-on-carbon and the resulting free amine coupled with N-CBZ-L-asparagine (1.17 g, 4.4 mmol) in the presence of N-hydroxybenzotriazole (1.19 g, 8.8 mmol) and EDC (843 mg, 4.4 mmol) to yield 2.11 g (78%) of [1S-[1R*(R*), 2S*]]- N¹[3-[[[(1,1-dimethylethyl)amino]carbonyl] (phenylmethyl)amino]-2-hydroxy-1-(phenylmethyl)propyl] -2-[(phenylmethylcarbamoyl)amino]-butanediamide; mp 156°–158° C. and MH+618. This compound (1.0 g, 1.62 mmol) was then deprotected by hydrogenation over 10% palladium-on-carbon and the resulting free amine coupled with 2-quinolinecarboxylic acid N-hydroxysuccinimide ester (437 mg, 1.62 mmol), in the presence of N-methylmorpholine, to afford 640 mg (62%) of pure [1S-[1R*(R*), 2S*]]- N¹[3-[[[(1,1-dimethylethyl)amino] carbonyl](phenylmethyl)amino]-2-hydroxy-1-(phenylmethyl)propyl]-2-[(2-quinolinylcarbonyl)amino]-butanediamide; mp 110.5°–112.5° C. and MH+639.

EXAMPLE 9

Additional exemplary compounds are listed in Table 1. These compounds were prepared according to the following general procedures.

General Procedure for the Synthesis of 1,3-Diamino 4-phenyl Butan-2-ol Derivatives A mixture of the amine R³NH₂ (20 equiv.) in dry isopropyl alcohol (20mL/mmol of epoxide to be converted) was heated to reflux and then treated with an N-Cbz amino epoxide of the formula:

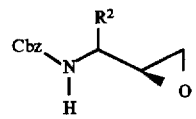

from a solids addition funnel over a 10–15 minute period. After the addition is complete the solution was maintained at reflux for an additional 15 minutes and the progress of the reaction monitored by TLC. In nearly all cases the reaction was found to be complete after this time period. The reaction mixture was then concentrated in vacuo to give an oil that was treated with n-hexane with rapid stirring whereupon the ring opened material precipitated from solution. Precipitation was generally complete within 1 hr and the product was then isolated by filtration on a Büchner funnel and then air dried. The product was further dried in vacuo. This method affords amino alcohols of sufficient purity for most purposes.

The above described amino epoxide can be prepared as shown in Example 6 or, alternatively can be prepared as follows.

Step A:

A solution of L-phenylalanine (50.0 g, 0.302 mol), sodium hydroxide (24.2 g, 0.605 mol) and potassium carbonate (83.6 g, 0.605 mol) in water (500 ml) is heated to 97° C. Benzyl bromide (108.5 ml, 0.912 mol) is then slowly added (addition time ~25 min). The mixture is then stirred at 97° C. for 30 minutes. The solution is cooled to room temperature and extracted with toluene (2×250 ml). The combined organic layers are then washed with water, brine, dried over magnesium sulfate, filtered and concentrated to give an oil product. The crude product is then used in the next step without purification.

Step B:

The crude benzylated product of the above step is dissolved in toluene (750 ml) and cooled to –55° C. A 1.5M solution of DIBAL-H in toluene (443.9 ml, 0.666 mol) is then added at a rate to maintain the temperature between –55° to –50° C. (addition time-1 hour). The mixture is stirred for 20 minutes at –55° C. The reaction is quenched at –55° C. by the slow addition of methanol (37 ml). The cold solution is then poured into cold (5° C.) 1.5N HCl solution (1.8 L). The precipitated solid (approx. 138 g) is filtered off and washed with toluene. The solid material is suspended in a mixture of toluene (400 ml) and water (100 ml). The mixture is cooled to 5° C., treated with 2.5N NaOH (186 ml) and then stirred at room temperature until the solid is dissolved. The toluene layer is separated from the aqueous phase and washed with water and brine, dried over magnesium sulfate, filtered and concentrated to a volume of 75 ml (89 g). Ethyl acetate (25 ml) and hexane (25 ml) are then added to the residue upon which the alcohol product begins to crystallize. After 30 min., an additional 50 ml hexane is added to promote further crystallization. The solid is filtered off and washed with 50 ml hexane to give approximately 35 g of material. A second crop of material can be isolated by refiltering the mother liquor. The solids are combined and recrystallized from ethyl acetate (20 ml) and hexane (30 ml) to give, in 2 crops, approximately 40 g (40% from L-phenylalanine) of analytically pure alcohol product. The mother liquors are combined and concentrated (34 g). The residue is treated with ethyl acetate and hexane which profides an additional 7 g (~7% yield) of slightly impure solid product. Further optimization in the recovery from the mother liquor is probable.

Step C:

A solution of oxalyl chloride (8.4 ml, 0.096 mol) in dichloromethane (240 ml) is cooled to –74° C. A solution of DMSO (12.0 ml, 0.155 mol) in dichloromethane (50 ml) is then slowly added at a rate to maintain the temperature at −74° C. (addition time ~1.25 hr). The mixture is stirred for 5 min. followed by addition of a solution of the alcohol (0.074 mol) in 100 ml of dichloromethane (addition time −20 min., temp. −75° C. to −68° C.). The solution is stirred at −78° C. for 35 minutes. Triethylamine (41.2 ml, 0.295 mol) is then added over 10 min. (temp. −78° to −68° C.) upon which the ammonium salt precipitated. The cold mixture is stirred for 30 min. and then water (225 ml) is added. The dichloromethane layer is separated from the aqueous phase and washed with water, brine, dried over magnesium sulfate, filtered and concentrated. The residue is diluted with ethyl acetate and hexane and then filtered to further remove the ammonium salt. The filtrate is concentrated to give the desired aldehyde product. The aldehyde was carried on to the next step without purification.

Temperatures higher than −70° C. has been reported in the literature for the Swern oxidation. Other Swern modifications and alternatives to the Swern oxidations are also possible.

A solution of the crude aldehyde 0.074 mol and chloroiodomethane (7.0 ml, 0.096 mol) in tetrahydrofuran (285 ml) is cooled to −78° C. A 1.6M solution of n-butyllithium in hexane (25 ml, 0.040 mol) is then added at a rate to maintain the temperature at −75° C. (addition time-15 min.). After the first addition, additional chloroiodomethane (1.6 ml, 0.022 mol) is added again, followed by n-butyllithium (23 ml, 0.037 mol), keeping the temperature at −75° C. The mixture is stirred for 15 min. Each of the reagents, chloroiodomethane (0.70 ml, 0.010 mol) and n-butyllithium (5 ml, 0.008 mol) are added 4 more times over 45 min. at −75° C. The cooling bath is then removed and the solution warmed to 22° C. over 1.5 hr. The mixture is poured into 300 ml of saturated aq. ammonium chloride solution. The tetrahydrofuran layer is separated. The aqueous phase is extracted with ethyl acetate (1×300 ml). The combined organic layers are washed with brine, dried over magnesium sulfate, filtered and concentrated to give a brown oil (27.4 g). The product could be used in the next step without purification. The desired diastereomer can be purified by recrystallization at a subsequent step.

Alternately, the product could be purified by chromatography.

General procedure for the Reaction of Amino Alcohols With Isocyanates: Preparation of Ureas A solution from the amino alcohol in tetrahydrofuran (THF) was treated at room temperature with the appropriate isocyanate of formula $R^4NCO$ via syringe under nitrogen. After the reaction has stirred for ~5 m the progress of the reaction was monitored by TLC. In nearly all cases the reaction was complete. The solvent was removed in vacuo and the product obtained was of sufficient purity for most purposes. The product may be further purified by dissolution in ethyl acetate and washing with 5% aqueous citric acid, water, and brine. The solvent is dried over anhydrous magnesium sulfate, filtered and concentrated in vacuo to give the pure urea.

General Procedure for the Removal of the Protecting Groups by Hydrogenolysis with Palladium on Carbon A. Alcohol Solvent The Cbz-protected peptide derivative was dissolved in methanol (ca.20 mL/mmol) and 10% palladium on carbon catalyst is added under a nitrogen atmosphere. The reaction vessel is sealed and flushed 5 times with nitrogen and then 5 times with hydrogen. The pressure is maintained at 50 psig for 1–16 hours and then the hydrogen replaced with nitrogen and the solution filtered through a pad of celite to remove the catalyst. The solvent is removed in vacuo to give the free amino derivative of suitable purity to be taken directly on to the next step.

B. Acetic Acid Solvent

The Cbz-protected peptide derivative was dissolved in glacial acetic acid (20 mL/mmol) and 10% palladium on carbon catalyst is added under a nitrogen atmosphere. The reaction vessel is flushed 5 times with nitrogen and 5 times with hydrogen and then maintained at 40 psig for about 2 h. The hydrogen was then replaced with nitrogen and the reaction mixture filtered through a pad of celite to remove the catalyst. The filtrate was concentrated and the resulting product taken up in anhydrous ether and evaporated to dryness 3 times. The final product, the acetate salt, was dried in vacuo and is of suitable purity for subsequent conversion.

General Procedure for Removal of Boc-protecting Group with 4N Hydrochloric Acid in Dioxane The Boc-protected amino acid or peptide is treated with a solution of 4N HCl in dioxane with stirring at room temperature. Generally the deprotection reaction is complete within 15 minutes, the progress of the reaction is monitored by thin layer chromatography (TLC). Upon completion, the excess dioxane and HCl are removed by evaporation in vacuo. The last traces of dioxane and HCl are best removed by evaporation again from anhydrous ether or acetone. The hydrochloride salt thus obtained is thoroughly dried in vacuo and is suitable for further reaction.

EDC/HOBt Coupling of Cbz-Asparagine (General Procedure)

N-CBZ-(L-asparagine (1.10 eq) and N-hydroxybenzotriazole (HOBt) (1.5 eq) are dissolved in dry dimethylformamide (DMF) (2–5 mL/mmol) and cooled in an ice bath. 1-(3-dimethylaminopropyl)-3-ethylcarbodiimide hydrochloride (EDC) (1.10 eq) is added to the stirring solution and maintained at 0° C. for 10 minutes. A solution of the amino component (free amine), 1.0 eq in DMF (1–2 mL/mmol), is added. [In the case of the amine hydrochloride or acetate salt, an equivalent of N-methylmorpholine is also added.] The reaction mixture is stirred at 0° C. for 1 hour and then at room temperature for ~5–6 hours. The reaction mixture is then poured into a rapidly stirring solution of 60% saturated aqueous sodium bicarbonate (ca-50 mL/mmol). An immediate white precipitate forms which is collected on a Büchner funnel and the solid washed thoroughly with saturated aqueous sodium bicarbonate, water, 5% aqueous citric acid solution and water. The product is thoroughly dried in vacuo and redissolved in DMF, filtered and reprecipitated by the addition to water. The precipitated product is isolated by filtration, washed again with water and dried in vacuo.

General Procedure for Acylation with 2-Quinoline Carboxylic Acid N-Hydroxysuccinimide Ester A solution of the free amine (or amine acetate salt) and 1.0 equivalent of N-hydroxysuccinimide 2-quinoline carboxylate in anhydrous dichloromethane was treated with 1.5 equivalents of N-methylmorpholine (NMM) at room temperature. The progress of the reaction was monitored by TLC and when the reaction was complete the reaction mixture was diluted with additional dichloromethane and the solution washed with saturated aqueous sodium bicarbonate, 5% aqueous citric acid, water and brine. The solution was dried over anhydrous magnesium sulfate, filtered and concentrated in vacuo. The product thus obtained was recrystallized from a mixture of acetone and hexane.

TABLE 1

| Entry No. | R | R³ | R⁴ |
|---|---|---|---|
| 1. | Cbz[a] | CH₃ | n-Butyl |
| 2. | Cbz | i-Butyl | CH₃ |
| 3. | Cbz | i-Butyl | n-Butyl |
| 4. | Q[b] | i-Butyl | n-Butyl |
| 5. | Cbz | i-Propyl | n-Butyl |
| 6. | Q | i-Propyl | n-Butyl |
| 7. | Cbz | C₆H₅ | n-Butyl |
| 8. | Cbz | —CH₂-cyclohexyl | n-Butyl |
| 9. | Cbz | —CH₂-phenyl | n-Butyl |
| 10. | Q | —CH₂-phenyl | n-Butyl |
| 11. | Cbz | cyclohexyl | n-Butyl |
| 12. | Cbz | i-Butyl | n-Propyl |
| 13. | Cbz | i-Butyl | —CH₂CH(CH₃)₂ |
| 14. | Cbz | (R)—CH(CH₃)-phenyl | n-Butyl |
| 15. | Cbz | —CH₂-cyclohexyl | i-Propyl |
| 16. | Cbz | —CH₂-cyclohexyl | —CH₂CH₂CH(CH₃)₂ |
| 17. | Cbz | i-Butyl | —CH₂CH₃ |
| 18. | Cbz | i-Butyl | —CH(CH₃)₂ |
| 19. | Cbz | i-Butyl | cyclohexyl |
| 20. | Q | i-Butyl | cyclohexyl |
| 21. | Cbz | —CH₂-cyclohexyl | —(CH₂)₂CH(CH₃)₂ |

TABLE 1-continued

[Structure: R-NH-CH(CONH₂-CH₂-)-C(=O)-NH-CH(CH₂Ph)-CH(OH)-CH₂-N(R³)-C(=O)-NH-R⁴]

| Entry No. | R | R³ | R⁴ |
|---|---|---|---|
| 22. | Cbz | (CH₂)₂CH(CH₃)₂ | —CH(CH₃)₂ |
| 23. | Q | i-Butyl | —CH(CH₃)₂ |
| 24. | Cbz | i-Butyl | —C(CH₃)₃ |
| 25. | Q | i-Butyl | —C(CH₃)₃ |
| 26. | Cbz | —CH₂-(2-naphthyl) | —C(CH₃)₃ |
| 27. | Q | —CH₂-(2-naphthyl) | —C(CH₃)₃ |
| 28. | Cbz | —(CH₂)₂CH(CH₃)₂ | —C(CH₃)₃ |
| 29. | Q | —(CH₂)₂CH(CH₃)₂ | —C(CH₃)₃ |
| 30. | Cbz | —CH₂C₆H₅ | —C(CH₃)₃ |
| 31. | Q | —CH₂C₆H₅ | —C(CH₃)₃ |
| 32. | Cbz | —(CH₂)₂C₆H₅ | —C(CH₃)₃ |
| 33. | Cbz | —(CH₂)₂C₆H₅ | —C(CH₃)₃ |
| 34. | Cbz | n-Butyl | —C(CH₃)₃ |
| 35. | Cbz | n-Pentyl | —C(CH₃)₃ |
| 36. | Cbz | n-Hexyl | —C(CH₃)₃ |
| 37. | Cbz | —CH₂C₆H₅ | —C(CH₃)₃ |
| 38. | Cbz | —CH₂C(CH₃)₃ | —C(CH₃)₃ |
| 39. | Q | —CH₂C(CH₃)₃ | —C(CH₃)₃ |
| 40. | Cbz | —CH₂CH₂—N(morpholino) | —C(CH₃)₃ |
| 41. | Cbz | —CH₂C₆H₅OCH₃(para) | —C(CH₃)₃ |
| 42. | Cbz | —CH₂-(3-pyridyl) | —C(CH₃)₃ |
| 43. | Cbz | —CH₂-(4-pyridyl) | —C(CH₃)₃ |
| 44. | Cbz | —(CH₂)₂C(CH₃)₃ | —C(CH₃)₃ |
| 45. | Q | —(CH₂)₂C(CH₃)₃ | —C(CH₃)₃ |
| 46. | Cbz | —(CH₂)₄OH | —C(CH₃)₃ |
| 47. | Q | —(CH₂)₄OH | —C(CH₃)₃ |
| 48. | Q | —CH₂-(4-fluorophenyl) | —C(CH₃)₃ |

TABLE 1-continued
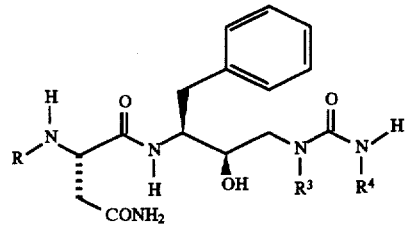
| Entry No. | R | R³ | R⁴ |
|---|---|---|---|
| 49. | Q | 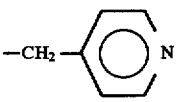 —CH₂— | —C(CH₃)₃ |
| 50. | 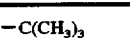 | —(CH₂CH(CH₃)₂ | —C(CH₃)₃ |
| 51. | 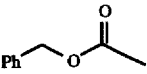 | —(CH₂CH(CH₃)₂ | —C(CH₃)₃ |
| 52. |  | —(CH₂CH(CH₃)₂ | —C(CH₃)₃ |
| 53. | 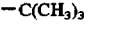 | —(CH₂CH(CH₃)₂ | —C(CH₃)₃ |
| 54. | 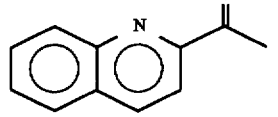 | —(CH₂CH(CH₃)₂ | —C(CH₃)₃ |
| 55. |  | —(CH₂CH(CH₃)₂ | —C(CH₃)₃ |
| 56. | 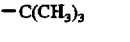 | —(CH₂CH(CH₃)₂ | —C(CH₃)₃ |
| 57. | 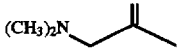 | —(CH₂CH(CH₃)₂ | —C(CH₃)₃ |
| 58. | 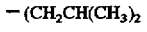 | —(CH₂CH(CH₃)₂ | —C(CH₃)₃ |

TABLE 1-continued
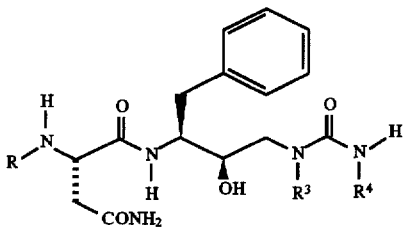
| Entry No. | R | R³ | R⁴ |
|---|---|---|---|
| 59. | 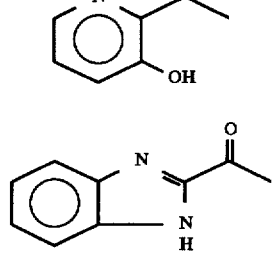 | —(CH₂CH(CH₃)₂ | —C(CH₃)₃ |
| 60. | 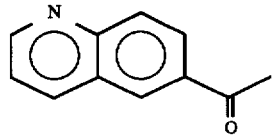 | —(CH₂CH(CH₃)₂ | —C(CH₃)₃ |
| 61. | 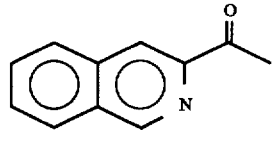 | —(CH₂CH(CH₃)₂ | —C(CH₃)₃ |
| 62. | 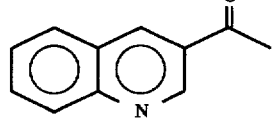 | —(CH₂CH(CH₃)₂ | —C(CH₃)₃ |
| 63. | 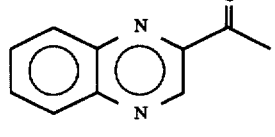 | —(CH₂CH(CH₃)₂ | —C(CH₃)₃ |
| 64. | 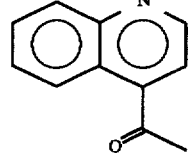 | —(CH₂CH(CH₃)₂ | —C(CH₃)₃ |
| 65. | 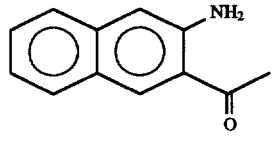 | —(CH₂CH(CH₃)₂ | —C(CH₃)₃ |
| 66. |  | —(CH₂CH(CH₃)₂ | —C(CH₃)₃ |

TABLE 1-continued

Structure:
R-NH-CH(CONH₂-CH₂)-C(=O)-NH-CH(CH₂-C₆H₅)-CH(OH)-CH₂-N(R³)-C(=O)-NH-R⁴

| Entry No. | R | R³ | R⁴ |
|---|---|---|---|
| 67. | 1-isoquinolinylcarbonyl (isoquinoline with C(=O)) | —(CH₂CH(CH₃)₂) | —C(CH₃)₃ |
| 68. | 2-aminobenzoyl (o-NH₂-C₆H₄-C(=O)—) | —(CH₂CH(CH₃)₂) | —C(CH₃)₃ |
| 69. | 1-hydroxy-2-naphthoyl (1-OH-naphthalene-2-C(=O)—) | —(CH₂CH(CH₃)₂) | —C(CH₃)₃ |

ᵃbenzyloxycarbonyl
ᵇ2-quinolinylcarbonyl

EXAMPLE 10

Following the generalized procedures set forth in Example 9, the compounds set forth in Table 2 were prepared.

TABLE 2

Structure:
A-NH-CH(CH₂-C₆H₅)-CH(OH)-CH₂-N(R³)-C(=O)-NH-R⁴

| Entry | A | R³ | R⁴ |
|---|---|---|---|
| 1. | Cbz—Val | i-amyl | t-Bu |
| 2. | Cbz—Leu | i-amyl | t-Bu |
| 3. | Cbz—Ile | i-amyl | t-Bu |
| 4. | Ac-D-homo-Phe | i-Bu | n-Bu |
| 5. | Qui—Orn(γ-Cbz) | —CH₂—C₆H₅ | t-Bu |
| 6. | Cbz—Asn | —CH₂CH=CH₂ | t-Bu |
| 7. | Acetyl-t-BuGly | i-amyl | t-Bu |
| 8. | Acetyl-Phe | i-amyl | t-Bu |
| 9. | Acetyl-Ile | i-amyl | t-Bu |
| 10. | Acetyl-Leu | i-amyl | t-Bu |
| 11. | Acetyl-His | i-amyl | t-Bu |
| 12. | Acetyl-Thr | i-amyl | t-Bu |
| 13. | Acetyl-NHCH(C(CH₃)₂(CH₃))C(O)— | i-amyl | t-Bu |
| 14. | Cbz—Asn | i-amyl | t-Bu |
| 15. | Cbz—Ala | i-amyl | t-Bu |
| 16. | Cbz—Ala | i-amyl | t-Bu |
| 17. | Cbz-beta-cyanoAla | i-amyl | t-Bu |
| 18. | Cbz-t-BuGly | i-amyl | t-Bu |
| 19. | Q-t-BuGly | i-amyl | t-Bu |
| 20. | Q-SCH₃Cys | i-amyl | t-Bu |
| 21. | Cbz—SCH₃Cys | i-amyl | t-Bu |
| 22. | Q-Asp | i-amyl | t-Bu |
| 23. | Cbz—(NHCH(C(CH₃)₂(SCH₃))C(O)— | i-amyl | t-Bu |
| 24. | Cbz—EtGly | i-amyl | t-Bu |
| 25. | Cbz—PrGly | i-amyl | t-Bu |
| 26. | Cbz—Thr | i-amyl | t-Bu |
| 27. | Q-Phe | i-amyl | t-Bu |
| 28. | Cbz—Phe | i-amyl | t-Bu |

EXAMPLE 11

Following the generalized procedure of Example 9, the compounds listed in Table 3 were prepared.

TABLE 3

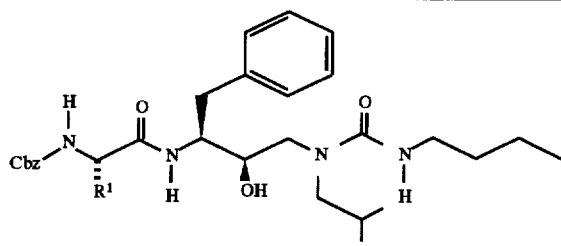

| Entry | R¹ |
|---|---|
| 1 | $CH_2SO_2CH_3$ |
| 2 | (R)—$CH(OH)CH_3$ |
| 3 | $CH(CH_3)_2$ |
| 4 | (R,S)$CH_2SOCH_3$ |
| 5 | $CH_2SO_2NH_2$ |
| 6 | $CH_2SCH_3$ |
| 7 | $CH_2CH(CH_3)_2$ |
| 8 | $CH_2CH_2C(O)NH_2$ |
| 9 | (S)—$CH(OH)CH_3$ |

EXAMPLE 12

Following the generalized procedures of Example 9, the compounds set forth in table 4 were prepared.

TABLE 4

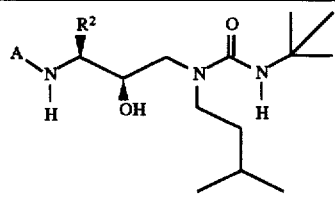

| Entry | R² | A |
|---|---|---|
| 1. | n-Bu | Cbz—Asn |
| 2. | cyclohexylmethyl | Cbz—Asn |
| 3. | n-Bu | Boc |
| 4. | n-Bu | Cbz |
| 5. | $C_6H_5CH_2$ | Boc |
| 6. | $C_6H_5CH_2$ | Cbz |
| 7. | $C_6H_5CH_2$ | benzoyl |
| 8. | cyclohexylmethyl | Cbz |
| 9. | n-Bu | Q-Asn |
| 10. | cyclohexylmethyl | Q-Asn |
| 11. | $C_6H_5CH_2$ | Cbz—Ile |
| 12. | $C_6H_5CH_2$ | Q-Ile |
| 13. | $C_6H_5CH_2$ | Cbz-t-BuGly |
| 14. | $C_6H_5CH_2$ | Q-t-BuGly |
| 15. | $C_6H_5CH_2$ | Cbz—Val |
| 16. | $C_6H_5CH_2$ | Q-Val |
| 17. | 2-naphthylmethyl | Cbz—Asn |
| 18. | 2-naphthylmethyl | Q-Asn |
| 19. | 2-naphthylmethyl | Cbz |
| 20. | n-Bu | Cbz—Val |
| 21. | n-Bu | Q-Val |
| 22. | n-Bu | Q-Ile |
| 23. | n-Bu | Cbz-t-BuGly |
| 24. | n-Bu | Q-t-BuGly |
| 25. | p-F($C_6H_4$)$CH_2$ | Q-Asn |
| 26. | p-F($C_6H_4$)$CH_2$ | Cbz |
| 27. | p-F($C_6H_4$)$CH_2$ | Cbz—Asn |

EXAMPLE 13

The compounds listed in Table 5 were prepared according to the generalized procedures of Example 9.

TABLE 5

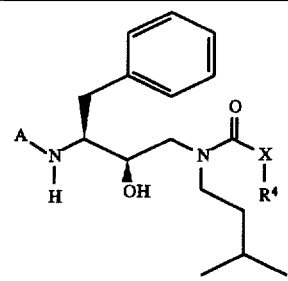

| Entry | XR⁴ | A |
|---|---|---|
| 1. | —NH$^t$Bu | Cbz—Asn |
| 2. | —NEt₂ | Cbz |
| 3. | —NHC(CH₃)₂CH₂CH₃ | Cbz |

EXAMPLE 14

The compounds of Table 6 were prepared according to the generalized procedures set forth in Example 9 except that instead of an isocyanate, an isothiocyanate equivalent was utilized.

TABLE 6

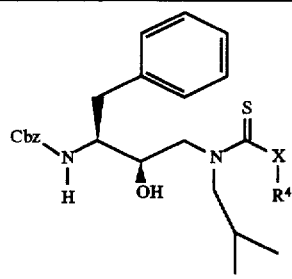

| Entry | XHR⁴ |
|---|---|
| 1. | NHEt |
| 2. | NH$^t$Bu |

The Cbz group of the compounds shown in Examples 13 and 14 can be removed as described in Example 9 and the resulting compound can be coupled to a desired α- or β-amino acid or the like to produce compounds of the present invention.

EXAMPLE 15

The compounds shown in Table 7 were prepared according to the following general procedure.

This general procedure represents a Curtius Rearrangement and reaction with the amino alcohol derivative as prepared following the general procedure in Example 9.

To a solution of 1 mmol of carboxylic acid in 12 mL of toluene and 3 mmol of triethylamine at 90° C. under a nitrogen atmosphere, was added 1 mmol of diphenylphosphoryl azide. After 1 hour, a solution of 1 mmol of amino alcohol derivative in 3.5 mL of either N,N-dimethylformamide or toluene was added. After 1 hour, the solvent was removed under reduced pressure, ethyl acetate and water added and the layers separated. The organic layer was washed with 5% citric acid, sodium bicarbonate, brine, dried, filtered and concentrated to afford the crude product.

This was then recrystallized or chromatographed on silica gel to afford the purified final compound.

TABLE 7

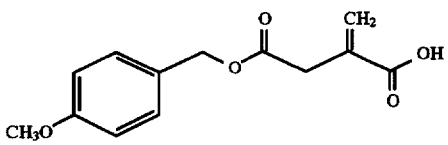

| R³ | R⁴ |
|---|---|
| —CH₂CH(CH₃)₂ | —C(CH₃)₃ |
| —CH₂CH₂CH(CH₃)₂ | 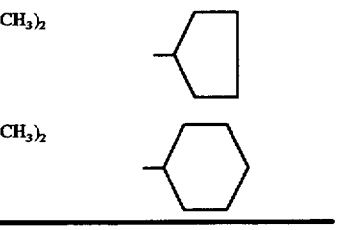 |
| —CH₂CH₂CH(CH₃)₂ |  |
| —CH₂CH₂CH(CH₃)₂ |  |
| —CH₂CH₂CH(CH₃)₂ |  |

EXAMPLE 16

A. Preparation of 4(4-methoxybenzyl)itaconate

A 5 L three-necked round bottomed flask equipped with constant pressure addition funnel, reflux condenser, nitrogen inlet, and mechanical stirrer was charged with itaconic anhydride (660.8 g, 5.88 mol) and toluene (2300 mL). The solution was warmed to reflux and treated with 4-methoxybenzyl alcohol (812.4 g, 5.88 mol) dropwise over a 2.6 h period. The solution was maintained at reflux for an additional 1.5 h and then the contents were poured into three 2 L erlenmeyer flasks to crystallize. The solution was allowed to cool to room temperature whereupon the desired mono-ester crystallized. The product was isolated by filtration on a Buchner funnel and air dried to give 850.2 g, 58% of material with mp 83°–85° C., a second crop, 17% was isolated after cooling of the filtrate in an ice bath. ¹H NMR (CDCl₃) 300 MHz 7.32(d, J=8.7 Hz, 2H), 6.91(d, J=8.7 Hz, 2H), 6.49(s, 1H), 5.85(s, 1H), 5.12(s, 2H), 3.83(s, 3H), 3.40(s, 2H).

B. Preparation of Methyl 4(4-methoxybenzyl) itaconate

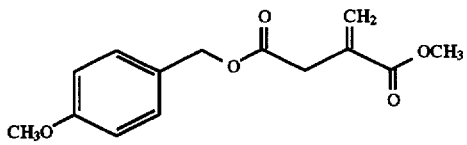

A 5 L three-necked round bottomed flask equipped with reflux condenser, nitrogen inlet, constant pressure addition funnel and mechanical stirrer was charged with 4(4-methoxybenzyl) itaconate (453.4 g, 1.81 mol) and treated with 1,5-diazabicyclo[4.3.0]non-5-ene (275.6 g, 1.81 mol), (DBN), dropwise so that the temperature did not rise above 15° C. To this stirring mixture was added a solution of methyl iodide (256.9 g, 1.81 mol) in 250 mL of toluene from the dropping funnel over a 45 m period. The solution was allowed to warm to room temperature and stirred for an additional 3.25 h.

The precipitated DBN hydroiodide was removed by filtration, washed with toluene and the filtrate poured into a separatory funnel. The solution was washed with sat. aq. NaHCO₃ (2×500 mL), 0.2N HCl (1×500 mL), and brine (2×500 mL), dried over anhyd. MgSO₄, filtered, and the solvent removed in vacuo. This gave a clear colorless oil, 450.2 g, 94% whose NMR was consistent with the assigned structure. ¹H NMR (CDCl₃) 300 MHz 7.30(d, J=8.7 Hz, 2H), 6.90(d, J=8.7 Hz, 2H), 6.34(s, 1H), 5.71 (s, 1H), 5.09(s, 2H), 3.82(s, 3H), 3.73(s, 3H), 3.38(s, 2H). ¹³C NMR (CDl₃) 170.46, 166.47, 159.51, 133.55, 129.97, 128.45, 127.72, 113.77, 66.36, 55.12, 51.94, 37.64.

C. Preparation of Methyl 4(4-methoxybenzyl) 2(R)-methylsuccinate

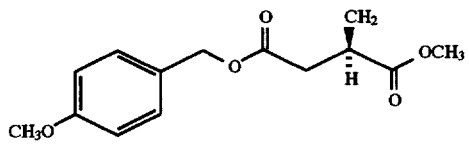

A 500 mL Fisher-Porter bottle was charged with methyl 4(4-methoxybenzyl) itaconate (71.1 g, 0.269 mol), rhodium (R,R) DiPAMP catalyst (204 mg, 0.269 mmol, 0.1 mol %) and degassed methanol (215 mL). The bottle was flushed 5 times with nitrogen and 5 times with hydrogen to a final pressure of 40 psig. The hydrogenation commenced immediately and after ca. 1 h the uptake began to taper off, after 3 h the hydrogen uptake ceased and the bottle was flushed with nitrogen, opened and the contents concentrated on a rotary evaporator to give a brown oil that was taken up in boiling iso-octane (ca. 200 mL, this was repeated twice), filtered through a pad of celite and the filtrate concentrated in vacuo to give 66.6 g, 93% of a clear colorless oil, ¹H NMR (CDCl₃ 300 MHz 7.30(d, J=8.7 Hz, 2H), 6.91 (d, J=8.7 Hz, 2H), 5.08(s, 2H), 3.82(s, 3H), 3.67(s, 3H), 2.95 (ddq, J=5.7, 7.5, 8.7 Hz, 1H), 2.79(dd, J=8.1, 16.5 Hz, 1H), 2.45(dd, J=5.7, 16.5 Hz, 1H), 1.23(d, J=7.5 Hz, 3H).

D. Preparation of Methyl 2(R)-methylsuccinate

A 3 L three-necked round-bottomed flask equipped with a nitrogen inlet, mechanical stirrer, reflux condenser and constant pressure addition funnel was charged with methyl 4(4-methoxybenzyl) 2(R)-methylsuccinate (432.6 g, 1.65 mol) and toluene (1200 mL). The stirrer was started and the solution treated with trifluoroacetic acid (600 mL) from the dropping funnel over 0.25 h. The solution turned a deep purple color and the internal temperature rose to 45° C. After stirring for 2.25 h the temperature was 27° C. and the solution had acquired a pink color. The solution was concentrated on a rotary evaporator. The residue was diluted with water (2200 mL) and sat. aq. NaHCO₃ (1000 mL). Additional NaHCO₃ was added until the acid had been neutralized. The aqueous phase was extracted with ethyl acetate (2×1000 mL) to remove the by-products and the aqueous layer was acidified to pH=1.8 with conc. HCl. This solution was extracted with ethyl acetate (4×1000 mL), washed with brine, dried over anhyd. MgSO₄, filtered and concentrated on a rotary evaporator to give a colorless liquid 251 g, >100% that was vacuum distilled through a short path apparatus cut 1: bath temperature 120° C.@>1 mm, bp 25°–29° C.; cut 2: bath temperature 140° C.@0.5 mm, bp 95°–108° C., 151 g, $[\alpha]_D$@25° C.=+1.38° C.(c=15.475, MeOH), $[\alpha]_D$=+8.48° C. (neat); cut 3: bath temperature 140° C., bp 108° C., 36 g, $[\alpha]_D$@25° C.=+1.49° C.(c=15.00, MeOH), $[\alpha]_D$=+8.98° C. (neat). Cuts 2 and 3 were combined to give 189 g, 78% of product, ¹H NMR (CDCl₃) 300 MHz 11.6(brs, 1H), 3.72(s, 3H), 2.92(ddq, J=5.7, 6.9, 8.0 Hz, 1H), 2.81 (dd, J=8.0, 16.8 Hz, 1H), 2.47(dd, J=5.7, 16.8 Hz, 1H), 1.26(d, J=6.9 Hz, 3H).

E. Preparation of Methyl Itaconate

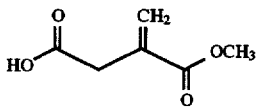

A 50 mL round bottomed flask equipped with reflux condenser, nitrogen inlet and magnetic stir bar was charged with methyl 4(4-methoxybenzyl) itaconate (4.00 g, 16 mmol). The solution was kept at room temperature for 18 hours and then the volatiles were removed in vacuo. The residue was taken up in ethyl acetate and extracted three times with saturated aqueous sodium bicarbonate solution. The combined aqueous extract was acidified to pH=1 with aqueous potassium bisulfate and then extracted three times with ethyl acetate. The combined ethyl acetate solution was washed with saturated aqueous sodium chloride, dried over anhydrous magnesium sulfate, filtered, and concentrated in vacuo. The residue was then vacuum distilled to give 1.23 g, 75% of pure product, bp 85–87@0.1 mm. ¹H NMR (CDCl₃) 300 MHz 6.34(s, 1H), 5.73(s, 2H), 3.76(s, 3H), 3.38(s, 2H). ¹³C NMR (CDCl₃) 177.03, 166.65, 129.220, 132.99, 52.27, 37.46.

F. Curtius Rearrangement of Methyl 2(R)-methylsuccinate: Preparation of Methyl N-MOz-α-methyl β-alanine.

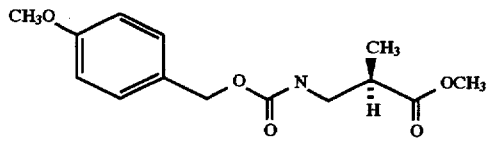

A 5 L four necked round bottomed flask equipped with a nitrogen inlet, reflux condenser, mechanical stirrer, constant pressure addition funnel, and thermometer adapter was charged with methyl 2(R)-methylsuccinate (184.1 g, 1.26 mol), triethylamine (165.6 g, 218 mL, 1.64 mol, 1.3 equivalents), and toluene (1063 mL). The solution was warmed to 85° C. and then treated dropwise with a solution of diphenylphosphoryl azide (346.8 g, 1.26 mol) over a period of 1.2 h. The solution was maintained at that temperature for an additional 1.0 h and then the mixture was treated with 4-methoxybenzyl alcohol (174.1 g, 1.26 mol) over a 0.33 h period from the dropping funnel. The solution was stirred at 88° C. for an additional 2.25 h and then cooled to room temperature. The contents of the flask were poured into a separatory funnel and washed with sat. aq. NaHCO₃ (2×500 mL), 0.2N HCl (2×500 mL), brine (1×500 mL), dried over anhyd. MgSO₄, filtered, and concentrated in vacuo to give 302.3 g, 85% of the desired product as a slightly brown oil. ¹H NMR (CDCl₃) 300 MHz 7.32(d, J=8.4 Hz, 2H), 6.91 (d, J=8.4 Hz, 2H), 5.2(brm, 1H), 5.05(s, 2H), 3.83(s, 3H), 3.70(s, 3H), 3.35(m, 2H), 2.70(m, 2H), 1.20(d, J=7.2 Hz, 3H).

G. Hydrolysis of Methyl N-Moz-α-methyl β-alanine: Preparation of α-methyl β-alanine Hydrochloride

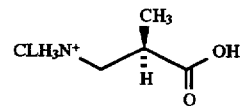

A 5 L three-necked round bottomed flask equipped with a reflux condenser, nitrogen inlet and mechanical stirrer was charged with methyl N-Moz-α-methyl β-alanine (218.6 g, 0.78 mol), glacial acetic acid (975 mL) and 12N hydrochloric acid (1960 mL). The solution was then heated to reflux for 3 h. After the solution had cooled to room temperature (ca. 1 h) the aqueous phase was decanted from organic residue (polymer) and the aqueous phase concentrated on a rotary evaporator. Upon addition of acetone to the concentrated residue a slightly yellow solid formed that was slurried with acetone and the white solid was isolated by filtration on a Buchner funnel. The last traces of acetone were removed by evacuation to give 97.7 g, 90% of pure product, mp 128.5°–130.5° C. $[\alpha]_D$@25° C.=9.0° C. (c=2.535, Methanol). ¹H NMR (D₂O) 300 MHz 3.29(dd, J=8.6, 13.0 Hz, 1H), 3.16(dd, J=5.0, 13.0m Hz, 1H), 2.94 (ddq, J=7.2, 5.0, 8.6 Hz, 1H), 1.30(d,J=7.2 Hz, 3H); ¹³C NMR (D₂O) 180.84, 44.56, 40.27, 17.49.

H. Preparation of N-BoC α-Methyl β-Alanine

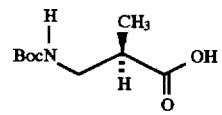

A solution of α-methyl β-alanine hydrochloride (97.7 g, 0.70 mol) in water (1050 mL) and dioxane (1050 mL) the pH was adjusted to 8.9 with 2.9N NaOH solution. This stirring solution was then treated with di-tert- butyl pyrocarbonate (183.3 g, 0.84 mol, 1.2 equivalents) all at once. The pH of the solution was maintained between 8.7 and 9.0 by the periodic addition of 2.5N NaOH solution. After 2.5 h the pH had stabilized and the reaction was judged to be complete. The solution was concentrated on a rotary evaporator (the temperature was maintained at <40° C.). The excess di-tert-butyl pyrocarbonate was removed by extraction with dichloromethane and then the aqueous solution was acidified with cold 1N HCl and immediately extracted with ethyl acetate (4×1000 mL). The combined ethyl acetate extract was washed with brine, dried over anhyd. MgSO₄, filtered and concentrated on a rotary evaporator to give a thick oil 127.3 g, 90% crude yield that was stirred with n-hexane whereupon crystals of pure product formed, 95.65 g, 67%, mp 76°–78° C., $[\alpha]_D$@25° C.=−11.8° C. (c=2.4, EtOH). A second crop was obtained by concentration of the filtrate and dilution with hexane, 15.4 g, for a combined yield of 111.05 g, 78%. ¹H NMR (acetone D₆) 300 MHz 11.7 (brs, 1H), 6.05 (brs 1H), 3.35 (m, 1H), 3.22 (m, 1H), 2.50 (m, 1H), 1.45(s, 9H), 1.19 (d, J=7.3 Hz, 3H); ¹³C NMR (acetone D₆) 177.01, 79.28, 44.44, 40.92, 29.08, 15.50. Elemental analysis calc'd.

for $C_9H_{17}NO_4$: C, 53.19, H, 8.42; N, 6.89. Found: C, 53.36; H, 8.46; N, 6.99.

I. Preparation of N-4-Methoxybenzyloxycarbonyl α-Methyl β-Alanine

A solution of N-4-methoxybenzyloxycarbonyl α-methyl β-alanine methyl ester (2.81 g, 10.0 mmol) in 30 mL of 25% aqueous methanol was treated with lithium hydroxide (1.3 equivalents) at room temperature for a period of 2 h. The solution was concentrated/n vacuo and the residue taken up in a mixture of water and ether and the phases separated and the organic phase discarded. The aqueous phase was acidified with aqueous potassium hydrogen sulfate to pH=1.5 and then extracted three times with ether. The combined ethereal phase was washed with saturated aqueous sodium chloride solution, dried over anhydrous magnesium sulfate, filtered and concentrated in vacuo to give 2.60 g, 97% of N-4-Methoxybenzyloxycarbonyl α-methyl β-alanine (N-Moz-AMBA) which was purified by recrystallization from a mixture of ethyl acetate and hexane to give 2.44 g, 91% of pure product, mp 96°–97° C., MH+=268. $^1$H NMR ($D_6$-acetone/300 MHz) 1.16 (3H, d, J=7.2Hz), 2.70 (1H, m), 3.31 (2H, m), 3.31 (3H, s), 4.99 (2H, s), 6.92 (2H, 4, J=8.7 Hz), 7.13 (2H, d, J=8.7 Hz).

J. Preparation of Propanamide, 3-(4-methoxybenzyloxycarbonyl)-N_[3-[[[(1,1-dimethylethyl)amine]carbonyl](3-methylbutyl)amino]-2-hydroxy-1-(phenylmethyl)propyl]-2-methyl-[IS-[IR*(S*), 2S*]]-

N-Moz-AMBA (468 mg, 1.75 mmol) was dissolved in 5 mL of DMF, HOBT (355 mg, 2.6 mmol) was added and the solution was cooled to 0° C. The solution was treated with (336 mg, 1.75 mmol) EDC for 15 minutes. To this was added (612 mg, 1.75 mmol) of [2R,3S 3-amino-1-isoamyl-1-(t-butylcarbonyl)amino 4-phenyl-2-butanol in 10 mL of DMF and the reaction stirred for 16 hours at room temperature. The DMF was concentrated to 5 mL and the product was precipitated by addition to 60% saturated aqueous $NaHCO_3$. The solid was taken up in ethyl acetate and washed with $KHSO_4$, $NaHCO_3$, NaCl(saturated), dried over $MgSO_4$ and concentrated to yield 680 mg of crude product which was crystallized from $CH_2Cl_2$, $Et_2O$, hexane, to yield 300 mg of pure product.

EXAMPLE 17

The compounds of Table 8 were prepared according to the procedure listed below and that utilized in Example 16.

Propaneamide, 3-[(1,1-dimethylethyl)butoxycarbonyl] amino-N-[3-[[[(1,1-dimethylethyl)amino]carbonyl](3-methylbutyl)amino]-2-hydroxy-1-(phenylmethyl)propyl]-2-methyl-,[1 S-[1R*(S*),2S*]-

Part A. A solution of N-t-butyloxycarbonyl-2-(R)-methyl-3-aminopropionic acid (372 mg, 1.83 mmol) and N-hydroxybenzotriazole (371 mg, 2.75 mmol) in 5 mL of dimethylformamide was cooled to 0 degrees C. To this was added EDC (351 mg, 1.83 mmol) and the solution was stirred for 15 minutes. To this chilled solution was added a solution of 3-[[[(1,1-dimethylethyl)amino]carbonyl](3-methylbutyrl)amino]-2(R)-hydroxy-1(S)(phenylmethyl) propylamine in 5 mL of dimethylformamide and stirred for 15 hours. The dimethylformamide was removed and replaced with 50 mL of ethyl acetate, and the organic phase was extracted with 5% potassium hydrogen sulfate, saturated sodium bicarbonate and brine. The ethyl acetate layer was dried over magnesium sulfate, filtered and concentrated to yield 613 mg of product after recrystallization from ethyl acetate, hexanes. (63% yield). M+Li 541

Part B. Preparation of Propaneamide, 3-amino-N-[3-[[[(1,1-dimethylethyl)amino]carbonyl]-(3-methylbutyl)amino]-2-hydroxy-1-(phenylmethyl)propyl]-2-methyl-,[1S-[1R*(S*), 2S*]-hydrochloride The product from part A. (577 mg, 1.08 mmol) was dissolved in 40 mL of 4N HCl in dioxane and the solution stirred for 2 hours, and concentrated to yield the hydrochloride salt in quantitative yield.

Part C. Preparation of Propaneamide, 3-(2-methylpropanoylamino)-N-[3-[[[(1,1-dimethylethyl)-amino]carbonyl](3-methylbutyl)amino]-2-hydroxy-1-(phenylmethyl)propyl]-2-methyl-,[1S-[1R*(S*),2S*]-

The product from part B. (236 mg, 0.5 mmol) was dissolved in anhydrous tetrahydrofuran and to this was added N-methylmorpholine (160 mg, 1.5 mmol) upon which time a precipitate formed. To this suspension was added isobutyryl chloride (53.5 mg, 0.5 mmol) and the suspension stirred for 15 hours. The suspension was diluted with ethyl acetate and washed with 5% potassium hydrogen sulfate, saturated sodium bicarbonate and brine. the organic layer was dried over magnesium sulfate, filtered and concentrated to yield 195 mg of crude product which was chromatographed on silica gel with 5% methanol methylene chloride to yield 121.5 mg (50 % yield) of pure product. M+Li 511

TABLE 8

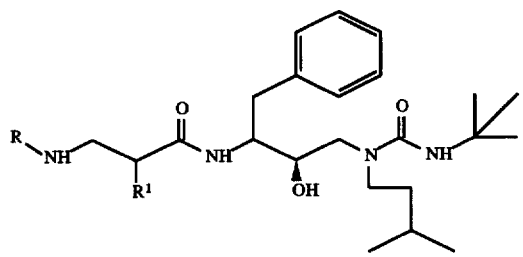

| | R | $R_1$ |
|---|---|---|
| 1. | CH₃O-C₆H₄-CH₂-O-C(O)- | —CH₃ |

TABLE 8-continued
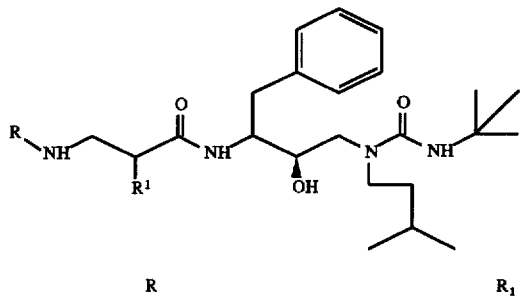
| | R | R₁ |
|---|---|---|
| 2. | 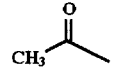 | —CH₃ |
| 3. | 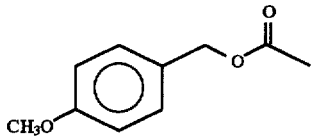 | —CH(CH₃)₂ |
| 4. | 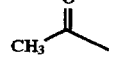 | —CH(CH₃)₂ |
| 5. | 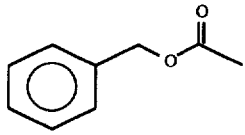 | —C(CH₃)₃ |
| 6. | 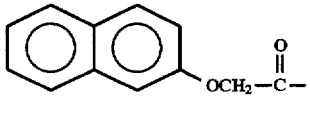 | —CH₃ |
| 7. | 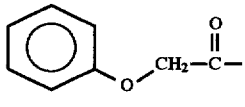 | —CH₃ |
| 8. | $HO_2CCH_2CH_2-\overset{O}{\underset{\|}{C}}-$ | —CH₃ |
| 9. | 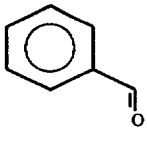 | —CH₃ |
| 10. | $CH_3NH-\overset{O}{\underset{\|}{C}}-$ | —CH₃ |
| 11. | $(CH_3)_2CH-\overset{O}{\underset{\|}{C}}-$ | —CH₃ |
| 12. | $CH_3OCH_2-\overset{O}{\underset{\|}{C}}-$ | —CH₃ |
| 13. | $(CH_3)_2NCH_2-\overset{O}{\underset{\|}{C}}-$ | —CH₃ |
| 14. | $CH_3CH(OH)-\overset{O}{\underset{\|}{C}}-$ | —CH₃ |

TABLE 8-continued
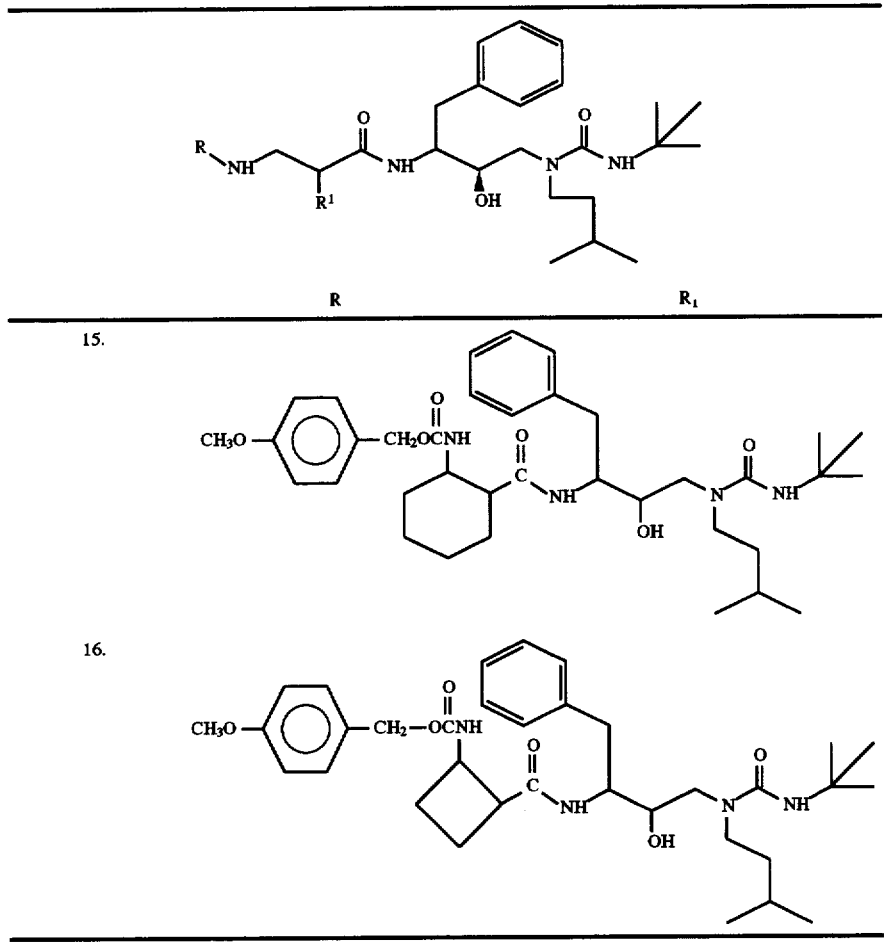
| | R | R₁ |
|---|---|---|
| 15. | (structure shown) | |
| 16. | (structure shown) | |
EXAMPLE 18
Following generally the procedure set forth in Example 16, the compounds shown in Table 9 were prepared.
TABLE 9
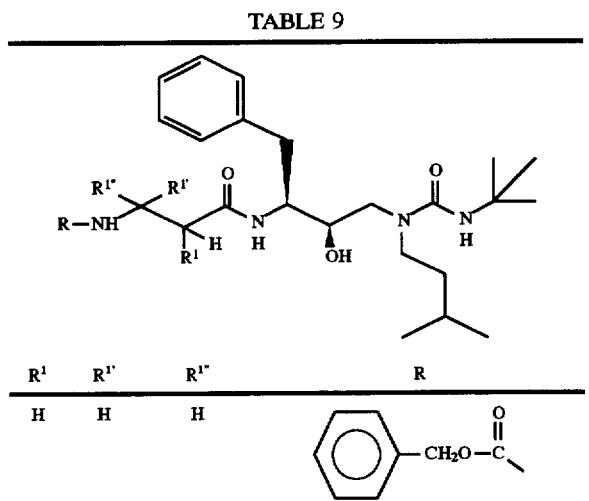
| $R^1$ | $R^{1'}$ | $R^{1''}$ | R |
|---|---|---|---|
| H | H | H | (benzyloxycarbonyl) |
TABLE 9-continued
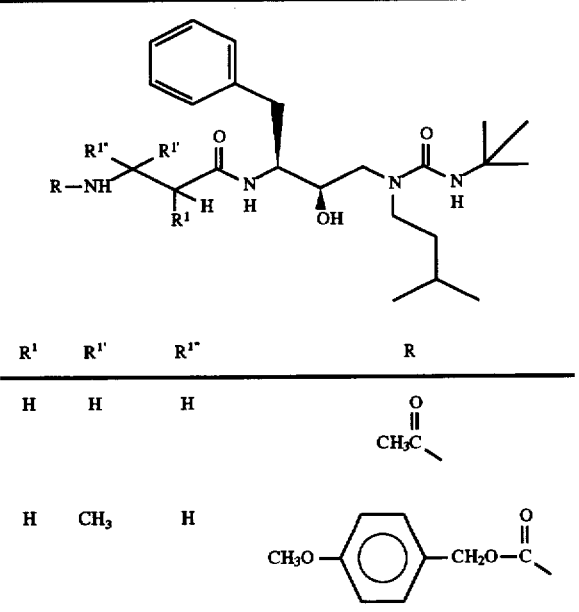
| $R^1$ | $R^{1'}$ | $R^{1''}$ | R |
|---|---|---|---|
| H | H | H | $CH_3C(=O)-$ |
| H | $CH_3$ | H | (4-methoxybenzyloxycarbonyl) |

TABLE 9-continued

[Structure: R-NH-C(R1')(R1'')-C(R1)(H)-C(=O)-NH-CH(CH2Ph)-CH(OH)-CH2-N(H)-C(=O)-N(H)-C(CH3)3]

| R¹ | R¹' | R¹" | R |
|---|---|---|---|
| H | CH₃ | CH₃ | PhCH₂O-C(=O)- |
| H | H | CO₂CH₃ | PhCH₂O-C(=O)- |
| H | H | H | 4-CH₃O-C₆H₄-CH₂O-C(=O)- |
| H | H | H | H₂N-C(=O)- |

EXAMPLE 19

The procedure set forth below was generally utilized to prepare the compounds shown in Table 9

TABLE 10

[Structure: R-N(R')-CH(C(CH3)3)-C(=O)-NH-CH(CH2-C6H4-X)-CH(OH)-CH2-N(H)-C(=O)-N(H)-C(CH3)3]

| R | R' | X |
|---|---|---|
| R=H | R'=H | X=H |
| R=Me | R'=Me | X=H |
| R=H | R'=Me | X=H |
| R=Me | R'=Me | X=F |
| R=H | R'=Me | X=F |
| R=Cbz | R'=Me | X=H |
| R=H | R'=Bz | X=H |
| R + R' = pyrrole* | | X=H |

*Ile in place of t-butylglycine

EXAMPLE 20

This example illustrates preparation of compounds wherein R⁴ and R⁵ together with X equal to N, forms a heterocycloalkyl radical.

a) Pyrrolidine carbamoyl chloride.

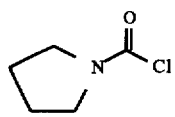

A stirring solution of triphosgene (27.78 g, 0.103 mol) in 40 mL toluene was cooled to −20° C. in an ice/salt bath under a blanket of nitrogen and treated with a solution of N-methylmorpholine (27.3 g, 0.27 mol) in 20 mL of toluene dropwise over 1 h. This solution was then treated with a solution of pyrrolidine (19.8 g, 0.27 mol) in 30 mL of toluene over a period of 30 m. The solution was allowed to warm to room temperature, filtered and the filtrate concentrated in vacuo to give an oil that was purified by vacuum distillation through a 12" Vigeraux column to give 20.7 g, 56%, bp 58° C.@0.6 mm, of pure product.

b) Butanediamide, $N^1$[3-[[(4-fluorophenyl)methyl)](1-pyrrolidinylcarbonyl)amino]-2-hydroxy-1-(phenylmethyl)propyl]-2-[(2-quinolinylcarbonyl)amino]-[1S[1R*(R*),2S*]]-

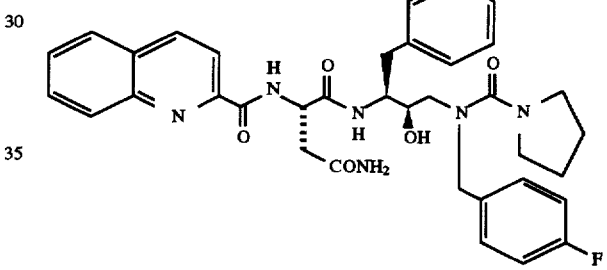

A stirring solution of [1S-[1R*(R*),2S*]]-$N^1$-[3-[[(4-fluorophenyl)methyl]amino]-2-hydroxy-1-(phenylmethyl)propyl]-2-[(2-quinolinylcarbonyl)amino-butanediamide (1.08 g, 1.91 mmol) in 7 mL of anhydrous DMF was treated with pyrrolidine carbamoyl chloride (260 mg, 1.95 mmol), 4-dimethylaminopyridine (15 mg), and N-methylmorpholine (380 mg, 3.76 mmol). The solution was stirred at room temperature for 3 h and then concentrated in vacuo to give a semi-solid that was dissolved in methanol/water ca. 2:1. A solid formed from this solid that was isolated by filtration on a Buchner funnel and washed with water, 5% aq. citric acid and water and air dried to give 130 mg of pure product, TLC on $SiO_2$ eluting with 7% methanol in ethyl acetate showed one spot with $R_f$=0.64, 11%.

c) Butanediamide, $N^1$[3-[[(4-fluorophenyl)methyl)](4-morpholinylcarbonyl)amino]-2-hydroxy-1-(phenylmethyl)propyl]-2-[(2-quinolinylcarbonyl)amino]-[1S[1R*(R*),2S*]]-

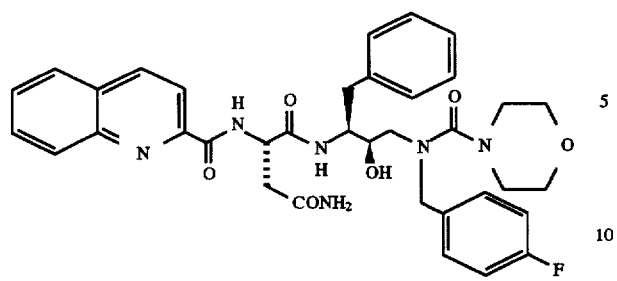

To a stirring solution of [1S-[1R*(R*),2S*]]-N¹-[3-[[(4-fluorophenyl)methyl]amino]-2-hydroxy-1-(phenylmethyl) propyl]-2-[(2-quinolinylcarbonyl)amino-butanediamide (520 mg, 0.922 mmol), triethylamine (172 mg, 1.70 mmol), 4-dimethylaminopyridine (50 mg), and morpholino carbamoyl chloride (157.3 mg, 1.05 mmol) in 5 mL of chloroform. The initially heterogeneous mixture was heated to reflux for 6 h. The solution was then diluted with additional chloroform, poured into a separatory funnel and washed with 1N KHSO₄, sat. aq. NaHCO₃, dried over anhyd. MgSO₄, filtered, and concentrated in vacuo to give a white solid that was purified by column chromatography on SiO₂ eluting with ethanol/ethyl acetate to give 380 mg, 61%, of pure product.

EXAMPLE 21

This example illustrates preparation of compounds wherein $R^4$ and $R^5$ are both other than H.

Butanediamide, N¹[3-[[(diethylamino)carbonyl](3-methylbutyl)amino]-2- hydroxy-1-(phenylmethyl)propyl]-2-[(2-quinolinylcarbonyl) amino]-[1S-[1R*(R*),2S*]]-

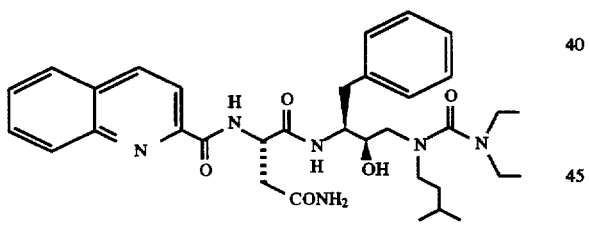

To a stirring solution of [1S-[1R*(R*),2S*]]-N¹-[3-(methylbutyl)amino]-2-hydroxy-1-(phenylmethyl)propyl]-2-[(2-quinolinylcarbonyl)amino-butane diamide] (119 mg, 0.21 mmol) triethylamine (59 mg, 0.58 mmol), 4-dimethylaminopyridine (9 mg), and diethyl carbamoyl chloride (157.3 mg, 1.05 mmol) in 4 mL of chloroform. The mixture was kept at room temperature for 26 h. The solution was then diluted with additional chloroform, poured into a separatory funnel and washed with 1N KHSO₄, sat. aq. NaHCO₃, dried over anhyd. MgSO₄, filtered, and concentrated in vacuo to give a white solid that was purified by column chromatography on SiO₂ eluting with methanol/CH₂Cl₂ to give 20 mg, 15%, of pure product.

EXAMPLE 22

Following the procedures set forth in Example 26, the compounds listed in Table 11 were prepared.

TABLE 11

![structure: Q—ASN—NH—CH(CH2Ph)—CH(OH)—CH2—N(R3)—C(O)—X(R4)—R5]

| $R_3$ | X—R4 / R5 |
|---|---|
| —CH₂CH(CH₃)₂ | —N(CH₃)₂ |
| —CH₂CH(CH₃)₂ | —N(CH₂CH₃)₂ |
| —CH₂CH(CH₃)₂ | —N(CH(CH₃)₂)₂ |
| —CH₂CH₂CH(CH₃)₂ | —(CH₃)₂ |
| —CH₂CH₂CH(CH₃)₂ | —N(CH₂CH₃)₂ |
| —CH₂CH₂CH(CH₃)₂ | morpholino (N-CH₂CH₂-O-CH₂CH₂) |
| —CH₂—C₆H₄—F | —N(CH₃)₂ and —N(CH2CH3)2 |
| —CH₂—C₆H₄—F | piperidino |
| —CH₂—C₆H₄—F | morpholino |
| —CH₂—C₆H₄—F | N(CH₃)(t-Bu) |
| —CH₂—C₆H₄—F | 2-methylpiperidino |
| —CH₂—C₆H₄—F | 2-(CO₂CH₃)pyrrolidino |
| —CH₂—C₆H₄—F | 2-(CH₃-CH₂)piperidino |
| —CH₂—C₆H₄—F | 4-methylpiperazino |

TABLE 11-continued

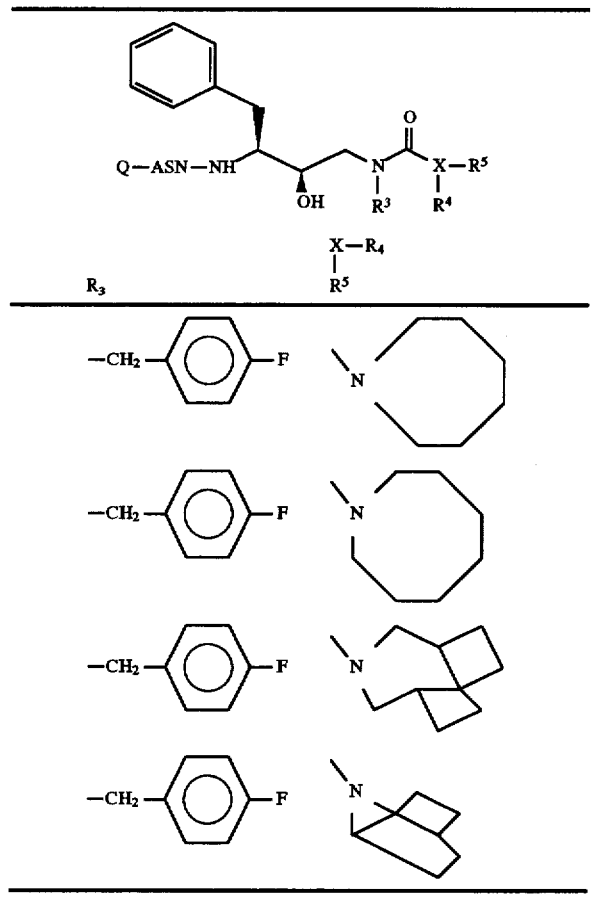

EXAMPLE 23A

This example illustrates preparation of compounds of Formula II wherein $R^1$ is an alkyl group other than an alkyl group of a naturally occurring amino acid side chain. In particular $R^1$ is a t-butyl group.

Part A. 3-[[(1,1-dimethylethyl)amino]carbonyl](3-methylbutyl)amino-2(R)-hydroxy-1(S)-[N-(benzyloxycarbonyl)(phenylmethyl()propyl amine] (4.7 gm, 9.7 mmol) was combined with 10% Pd on carbon (200 mg) and conc. HCl (3 mL) in ethanol (35 mL) and hydrogenated at 50 psi of hydrogen for 2.5 h. The reaction mixture was filtered through diatomaceous earth and concentrated on a rotary evaporator to a yellow hygroscopic solid; 3.7 gm, 100%.

Part B. Butaneamide, 2-[(phenylmethyloxycarbonyl)amino]-N-[3-[[[(1,1-dimethylethyl)amino]carbonyl](3-methylbutyl)amino]-2-hydroxy-1-(phenylmethyl)propyl-3,3-dimethyl-[1S-[1R*(R*),2S*]]-

N-Cbz-L-tert-leucine (172 mg, 0.65 mmol) and N-hydroxybenzotriazole (100 mg, 0.65 mmol) in DMF (3 mL) was cooled to 0° C. and EDC (115 mg, 0.60 mmol) added. After 45 min the amine from Part A (193 mg, 0.50 mmol) and N-methylmorpholine (60 uL, 0.55 mmol) were added. The reaction was stirred at ambient temperature for 18 h and poured into a solution of 50% saturated NaHCO₃ (25 mL). The solid was collected by suction filtration, washed with water and dried in-vacuo. The solid was chromatographed on SiO₂ using 2% MeOH in CH₂Cl₂. The appropriate fractions were pooled and concentrated to afford a white solid; 220 mg, MH+597, TLC (SiO₂ 2% MeOH/CH₂Cl₂) R_f=0.2. CHN requires: C, 68.42, H, 8.78, N, 9.39; found: C, 68.03, H, 8.83, N, 9.33.

Part C. Butaneamide, 2-amino-N-[3-[[[(1,1-dimethylethyl)amino]carbonyl](3-methylbutyl)amino]-2-hydroxy-1-(phenylmethyl)propyl]-3,3-dimethyl-, [1 S-[1 R*(R*), 2S*]-

The product from Part B (570 mg, 0.95 mmol) and 4% Pd on carbon (150 mg) in ethanol (30 mL) was hydrogenated at 5 psi for 2.75 h. The reaction mixture was filtered through diatomaceous earth and concentrated on a rotary evaporator to an oil; 438 mg, 100%.

Part D. Butaneamide, 2-(acetylamino)-N-[3-[[[(1,1-dimethylethyl)amino]carbonyl](3-methylbutyl)amino]-2-hydroxy-1-(phenylmethyl)propyl]-3,3-dimethyl-, [1 S-[1R*(R*), 2S*]-

The product from Part C (206 mg, 0.41 mmol) and N-methylmorpholine (45 uL, 0.41 mmol) were dissolved in CH₂Cl₂ (2.5 mL) and cooled to 0 C. Acetic anhydride (39 uL, 0.41 mmol) was then added and the reaction stirred 30 min at 0 C, then allowed to warm to ambient temperature and stir for 30 min. The solvent was removed on a rotary evaporator and the residue dissolved in ethanol (2 mL). The ethanolic solution was slowly poured into 50% saturated NaHCO₃ (20 mL) and stirred vigorously. The solid was collected by suction filtration and washed with water, 5% citric acid, and again with water; 157 mg, 75%. CHN/1.5 H₂O requires: C 63.24, H, 9.67, N, 10.54; found: C, 63.40, H, 9.41, N, 10.39.

Part D2. Butaneamide, 2-[(2,2-dimethylaminoacetyl)amino]-N-[3-[[[(1,1-dimethylethyl)amino]carbonyl](3-methylbutyl)amino]-2-hydroxy-1-(phenylmethyl)propyl]-3,3-dimethyl-,[1S-[1R*(R*), 2S*]]-

To a solution of N,N-dimethylaminoacetic acid (62 mg, 0.6 mmol) and N-hydroxybensotriazole (87 mg, 0.57 mmol) in 2 mL of DMF at 0° C. was added EDC (109 mg, 0.57 mmol). The reaction mixture was stirred for 1 hour and then (2R, 3S)-3(L-tert-butylglycinyl) amido-1-isoamyl 1(tert-butylcarboamoyl) amino-4-phenyl-2-butanol (231 mg, 0.5 mmol) was added. The reaction was stirred at room temperature for 16 hours and then concentrated in vacuo. The residue was chromatographed on silica (50 gm) using 5% ethanol in dichloromethane. The butaneamide, 2-[(2,2-dimethylaminoacetyl)amino]-N-[3-[[[(1,1-dimethylethyl)amino]carbonyl](3-methylbutyl)amino]-2-hydroxy-1-(phenylmethyl)propyl]-3,3-dimethyl-, [1S-[1R*(R*)),2S*]]- was obtained as a white solid Anal. Calc'd for C₃₀H₅₃N₅O₄.0.3 H₂O:C,65.13;H, 9.77; N, 12.66. Found: C, 65.10; H, 9.79; N, 12.52.

EXAMPLE 23B

The compound of Example 23A, Part D2, was prepared by an alternate method as described below.

To a solution of butaneamide, 2-amino-N-[3-[[[(1,1-dimethylethyl)amino]-carbonyl](3-methylbutyl)amino]-2-hydroxy-1-(phenylmethyl)propyl]-3,3-dimethyl-,[1S-[1 R*(R*), 2S*]- (694 mg, 1.5 mmol) and N-methylmorpholine (175 uL, 1.6 mmol) in 5 mL of dichloromethane was added bromoacetyl chloride (132 uL, 1.6 mmol). After 20 minutes at room temperature the solvent was removed on a rotary evaporator and the residue chromatographed on silica (50 gm) using 2% methanol in dichloromethane. The product was obtained as a white solid Anal. Calc'd for C₂₈H₄₇N₄O₄Br.H₂O: C, 55.90; H, 8.21; N, 9.31. Found: C, 55.67; H, 7.90; N, 9.08.

To a solution of butaneamide, 2-[(2-bromoacetyl) amino]-N-[3-[[[(1,1-dimethylethyl)amino]carbonyl](3-methylbutyl)amino]-2-hydroxy-1-(phenylmethyl)propyl]-3, 3-dimethyl-,[1S-[1R*(R*), 2S*]]- (582 mg, 1.0 mmol) and N,N-diisopropylethylamine (260 mL², 1.5 mmol) in 10 mL of dichloromethane was added N,N-dimethylamine hydrochloride (122 mg 1.5 mmol). The reaction was stirred at room temperature for 16 hours, then concentrated on a rotary evaporator. The residue was chromatographed on silica (50 gm) using 2.5% methanol in dichloromethane. The butaneamide, 2-[(2,2-dimethylaminoacetyl)amino]-N-[3-[[[ (1,1-dimethylethyl)amino]-carbonyl](3-methylbutyl)amino] -2-hydroxy- 1-(phenylmethyl)propyl]-3,3-dimethyl-, [1S-[1R*(R*), S*]]- was obtained as a white solid Anal Calc'd for $C_{30}H_{53}N_5O_4 \cdot 0.22\ CH_2Cl_2$: C, 64.00; H, 9.50; N, 12.35. Found: C, 63.97; H, 9.51; N, 12.24.

Butaneamide, 2-amino-N-[3-[[[(1,1-dimethylethyl) amino]-carbonyl](3-methylbutyl)amino]-2-hydroxy-1-(phenylmethyl)propyl]-3,3-dimethyl-, [1S-[1R*(R*), S*]]- was also capped, generally utilizing the procedures shown in Examples 23A and 23B, with the acyl groups shown in Table 12.

TABLE 12

| Acyl Group (R) |
| --- |
| benzyloxycarbonyl |
| tert-butoxycarbonyl |
| acetyl |
| 2-quinoylcarbonyl |
| phenoxyacetyl |
| benzoyl |
| methyloxaloyl |
| pivaloyl |
| trifluoroacetyl |
| bromoacetyl |
| hydroxyacetyl |
| morpholinylacetyl |
| N,N-dimethylaminoacetyl |
| N-benzylaminoacetyl |
| N-phenylaminoacetyl |
| N-benzyl-N-methylaminoacetyl |
| N-methyl-N-(2-hydroxyethyl)aminoacetyl |
| N-methylcarbamoyl |
| 3-methylbutyryl |
| N-isobutylcarbamoyl |
| succinoyl (3-carboxypropionyl) |
| carbamoyl |
| N-isobutylamino acetyl |
| N,N-diethylamino acetyl |
| N-(2-methoxyethyl)aminoacetyl |
| N-(S-α-methylbenzyl)aminoacetyl |
| N-(R-α-methylbenzyl)amino acetyl |
| N-(S-2-tetralin)amino acetyl |
| N-(R-2-tetralin)amino acetyl |
| N-pyrrolidinylacetyl |
| N-methyl-N-(2-pyridylethyl)amino acetyl |
| N-tetrahydroisoquinolylaminoacetyl |
| N-p-methoxybenzylamino acetyl |

EXAMPLE 24A

The procedure described below illustrates preparation of compounds of Formula III. Propanamide, N-[3-[[[(1,1-dimethylethyl)amino]carbonyl](3-methylbutyl)amino]-2-hydroxy-1-(phenylmethyl)propyl]-2-methyl-3-(2-phenylethylsulfonyl)-[1S-[1R*(R*),2S*]] and its diastereomer.

Part A. A solution of methyl methacrylate (7.25 g, 72.5 mmol) and phenethyl mercaptan (10.0 g, 72.5 mmol) in 100 mL of methanol was cooled in an ice bath and treated with sodium methoxide (100 mg, 1.85 mmol). The solution was stirred under nitrogen for 3 h and then concentrated in vacuo to give an oil that was taken up in ether and washed with 1N aqueous potassium hydrogen sulfate, saturated aqueous sodium chloride, dried over anhydrous magnesium sulfate, filtered and concentrated to give 16.83 g, 97.5% of methyl 2-(R,S)-methyl-4-thia-6-phenyl hexanoate as an oil. TLC on $SiO_2$ eluting with 20:1 hexane:ethyl acetate (v:v) $R_f$=0.41.

Part B. A solution of methyl 2-(R,S)-methyl-4-thia-6-phenyl hexanoate (4.00 g, 16.8 mmol) in 100 mL of dichloromethane was stirred at room temperature and treated portion wise with meta-chloroperoxybenzoic acid (7.38 g, 39.2 mmol) over approximately 40 m. The solution was stirred at room temperature for 16 h and then filtered and the filterate washed with saturated aqueous sodium bicarbonate, 1N sodium hydroxide, saturated aqueous sodium chloride, dried over anhydrous magnesium sulfate, filtered, and concentrated to give 4.50 g, 99% of desired sulfone. The unpurified sulfone was dissolved in 100 mL of tetrahydrofuran and treated with a solution of lithium hydroxide (1.04 g, 24.5 mmol) in 40 mL of water. The solution was stirred at room temperature for 2 m and then concentrated in vacuo. The residue was then acidified with 1N aqueous potassium hydrogen sulfate to pH=1 and then extracted three times with ethyl acetate. The combined ethyl acetate solution was washed with saturated aqueous sodium chloride, dried over anhydrous magnesium sulfate, filtered and concentrated to give a white solid. The solid was taken up in boiling ethyl acetate/hexane and allowed to stand undisturbed whereupon white needles formed that were isolated by filtration and air dried to give 3.38 g, 79% of 2-(R,S)-methyl-3(β-phenethylsulfonyl)-propionic acid, mp 91°–93° C.

Part C. A solution of 2-(R,S)-methyl-3(β-phenethylsulfonyl) -propionic acid (166.1 mg, 0.65 mmol), N-hydroxybenzotriazole (HOBT) (146.9 mg, 0.97 mmol), and 1-(3-dimethylaminopropyl)-3-ethylcarbodiimide hydrochloride (EDC) (145.8 mg, 0.75 mmol) in 4 mL of anhydrous dimethylformamide (DMF) cooled to 0° C. and stirred under nitrogen for 0.5 h. This solution was then treated with 3-[[(dimethylethyl)amino]carbonyl](3-methylbutyl)amino-2(R)-hydroxy-1(S)-(phenylmethyl)propyl amine (201.9 mg, 0.59 mmol) and stirred at room temperature for 16 h. The solution was poured into 30 mL of 60% saturated aqueous sodium bicarbonate solution. The aqueous solution was then decanted from the organic residue. The organic residue was taken up in dichloromethane and washed with 10% aqueous citric acid, brine, dried over anhydrous magnesium sulfate, filtered and concentrated to give 110.0 mg, 32% of (2R,3S) -3-[N-2-(R)-methyl-3-(β-phenethylsulfonyl)propionyl] amido-1-isoamyl-1-(tert-butylcarbamoyl)amino-4-phenyl-2-butanol and (2R,3S)-3-[N-2-(S)-methyl-3-(β-phenethylsulfonyl)propionyl]amido-1-isoamyl-1-(tert-butylcarbamoyl)amino-4-phenyl-2-butanol. FAB mass spectrum (MH+)=588. Flash chromatography of the mixture on silica gel eluting with 1:1 hexane:ethyl acetate afforded the separated diastereomers.

EXAMPLE 24B

Propanamide, N-[3-[[[(1,1-dimethylethyl)amino]carbonyl] (3-methylbutyl)amino]-2-hydroxy-1-(phenylmethyl)propyl] -2-methyl-3-(methylsulfonyl)-[1S-[1R*(R*), 2S*]], and its diastereomer.

Part A. A solution of methyl 2-(bromomethyl)-acrylate (26.4 g, 0.148 mol) in 100 mL of methanol was treated with sodium methanesulfinate (15.1 g, 0.148 mol) portion wise over 10 m at room temperature. The solution was then stirred at room temperature for a period of 1.25 h and the solution concentrated in vacuo. The residue was then taken up in water and extracted four times with ethyl acetate. The combined ethyl acetate solution was washed with saturated sodium chloride, dried over anhydrous magnesium sulfate, filtered and concentrated to give a white solid, 20.7 g which was taken up in boiling acetone/methyl tert-butyl ether and allowed to stand whereupon crystals of pure methyl 2-(methylsulfonylmethyl) acrylate 18.0 g, 68% formed, mp 65°–68 0° C.

Part B. A solution of methyl 2-(methylsulfonylmethyl) acrylate (970 mg, 5.44 mmol) in 15 mL of tetrahydrofuran was treated with a solution of lithium hydroxide (270 mg, 6.4 mmol) in 7 mL of water. The solution was stirred at room temperature for 5 m and then acidified to pH=1 with 1N aqueous potassium hydrogen sulfate and the solution extracted three times with ethyl acetate. The combined ethyl acetate solution was dried over anhydrous magnesium sulfate, filtered, and concentrated to give 793 mg, 89% of 2-(methylsulfonylmethyl) acrylic acid, mp 147°–149 0° C.

Part C. A solution of 2-(methylsulfonylmethyl) acrylic acid (700 mg, 4.26 mmol) in 20 mL of methanol was charged into a Fisher-Porter bottle along with 10% palladium on carbon catalyst under a nitrogen atmosphere. The reaction vessel was sealed and flushed five times with nitrogen and then five times with hydrogen. The pressure was maintained at 50 psig for 16 h and then the hydrogen was replaced with nitrogen and the solution filtered through a pad of celite to remove the catalyst and the filterate concentrated in vacuo to give 682 mg 96% of 2-(R,S)-methyl-3-methylsulfonyl propionic acid.

Part D. A solution of 2-(R,S)-methyl-3(methylsulfonyl) propionic acid (263.5 mg, 1.585 mmol), N-hydroxybenzotriazole (HOBT) (322.2 mg, 2.13 mmol), and 1-(3-dimethylaminopropyl)-3-ethylcarbodiimide hydrochloride (EDC) (339.1 mg, 1.74 mmol) in 4 mL of anhydrous dimethylformamide (DMF) cooled to 0° C. and stirred under nitrogen for 0.5 h. This solution was then treated with 3-[[(1,1 -dimethylethyl)amino]carbonyl](3-methylbutyl) amino-2(R)-hydroxy-1(S)-(phenylmethyl)propyl amine (543.5 mg, 1.58 mmol) and stirred at room temperature for 16 h. The solution was poured into 60 mL of 60% saturated aqueous sodium bicarbonate solution. The aqueous solution was then decanted from the organic residue. The organic residue was taken up in dichloromethane and washed with 10% aqueous citric acid, brine, dried over anhydrous magnesium sulfate, filtered and concentrated to give 471.8 mg, 60% of Propanamide, N-[3-[[[(1,1-dimethylethyl)amino] carbonyl](3-methylbutyl)amino]-2-hydroxy-1 -(phenylmethyl)propyl]-2-methyl-3-(methylsulfonyl)-, [1S-[1R*(R*), 2S*]]- and its diastereomer.

EXAMPLE 25

Preparation of Sulfone Inhibitors from L-(+)-S-acetyl-β-mercaptoisobutyric Acid

Part A. Propanamide, N-[3-[[[(1,1-dimethylethyl)amino] carbonyl](3-methylbutyl)amino]-2-hydroxy-1 -(phenylmethyl)propyl]-2-methyl-3-S-acetyl)-[1 S-[1 R*), 2S*]]-.

A round-bottomed flask was charged with (2R,3R)-3-amino-1 -isoamyl-1 -(tert-butylcarbamoyl)amino-4-phenyl-2-butanol (901.5 mg, 2.575 mmol), L-(+)-S-acetyl-b-mercaptoisobutyric acid (164.5 mg, 2.575 mmol), 1-(3-dimethylaminopropyl)-3-ethylcarbodiimide hydrochloride (EDC) (339.1 mg, 1.74 mmol), and 10 mL of $CH_2Cl_2$ and allowed to stir at room temperature for 16 h. The solution was concentrated in vacuo and the residue taken up in ethyl acetate, washed with 1N $KHSO_4$ sat. aq. $NaHCO_3$, brine, dried over anhydrous $MgSO_4$, filtered and concentrated to give an oil that was purified by radial chromatography on $SiO_2$ eluting with ethyl acetate to give the pure product, 800 mg, 63%.

Part B. Propanamide, N-[3-[[[(1,1-dimethylethyl)amino] carbonyl](3-methylbutyl)amino]-2-hydroxy-1-(phenylmethyl)propyl]-2-methyl-3-mercapto)-, [1S-1R*(R*),2S*]]-.

A solution of [1S-[1R*(R*),2S*]]- N-[3-[[[(1,1-dimethylethyl)amino]carbonyl](3-methylbutyl)amino]-2-hydroxy-1-(phenylmethyl)propyl]-2-methyl-3-S-acetyl)-propanamide (420 mg, 0.85 mmol) in 10 mL of methanol was treated with anhydrous ammonia for ca. 1 m at 0° C. The solution was stirred at that temperature for 16 h and then concentrated in vacuo to give 380 mg, 99%, of the desired product that was used directly in the next step without further purification.

Part C. Propanamide, N-[3-[[[(1,1-dimethylethyl)amino] carbonyl](3-methylbutyl)amino]-2-hydroxy-1-(phenylmethyl)propyl]-2-methyl-3-S-methyl-, [1S-[1R*(R*),2S*]]-.

A solution of [1S-[1R*(R*),2S*]]- N-[3-[[[(1,1-dimethylethyl)amino]carbonyl](3-methylbutyl)amino]-2-hydroxy-1 -(phenylmethyl)propyl]-2-methyl-3-mercapto)-propanamide (380 mg, 0.841 mmol) in 10 mL of dry toluene under nitrogen was treated in rapid succession with 1,8-diazabicyclo[5.4.0]undec-7-ene, (DBU), (128.1 mg, 0.841 mmol) and iodomethane (119.0 mg, 0.841 mmol). After 0.5 h at room temperature the reaction was found to be complete and the solution was diluted with ethyl acetate washed with 1N $KHSO_4$, sat. aq. $NaHCO_3$, brine. After the solution was dried over anhydrous $MgSO_4$, filtered and concentrated in vacuo the desired product was obtained as white foam was obtained, 370 mg, 94.5%, that was used directed in the next step.

Part D. Propanamide, N-[3-[[[(1,1-dimethylethyl)amino] carbonyl](3-methylbutyl)amino]-2-hydroxy-1 -(phenylmethyl)propyl]-2-methyl-3-(methylsulfonyl)-, [1S-[1R*(R*),2S*]]-.

A solution of [1S-[1R*(R*),2S*]]-N-[3-[[[(1,1-dimethylethyl)amino]carbonyl](3-methylbutyl)amino]-2-hydroxy- 1-(phenylmethyl)propyl]-2-methyl-3-S-methyl)-propanamide (340 mg, 0.73 mmol) and sodium perborate (500 mg, 3.25 mmol) in 30 mL of glacial acetic acid was warmed to 55° C. for 16 h. The solution was concentrated in vacuo and then the residue taken up in ethyl acetate, washed with water, sat. aq. $NaHCO_3$, brine, dried over anhydrous $MgSO_4$, filtered and concentrated to give the desired product as a white solid, 350 mg, 96%.

EXAMPLE 26

The compounds shown in Tables 13 and 14 were prepared generally according to the procedure set forth in Examples 24 and 25.

TABLE 13

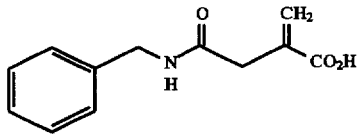

| R' |
| --- |
| CH₃ — |
| CH₃CH₂ — |
| CH₃CH₂CH₂ — |
| PhCH₂CH₂ — |
| PhCH₂ — |
| Ph — |
| (CH₃)₂CH — |
| HOCH₂CH₂ — |
| $C_6H_5CH_2O-\overset{O}{\overset{\|}{C}}CH_2$ |
| $H_2N-\overset{O}{\overset{\|}{C}}-CH_2-$ |
| (cyclohexyl)— |
| CH₂=CH—CH₂— |

TABLE 14

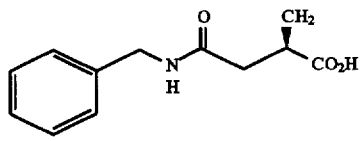

| R' | R₁ |
| --- | --- |
| CH₃ | —CH(CH₃)₂ |

EXAMPLE 27

Preparation of 2(S)-methyl-3-(methylsulfonyl) propionic Acid

To a solution of 10 g of D-(−)-S-benzoyl-b-mercaptioisobutyric acid t-butyl ester in 20 mL of methanol was bubbled in gaseous ammonia at 0° C. The reaction was allowed to then warm to room temperature, stirred overnight and concentrated under reduced pressure. The resulting mixture of a solid (benzamide) and liquid was filtered to provide 5.21 g of a pale oil which then solidified. This was identified as 2(S)-methyl-3-mercaptopropionic aid t-butyl ester.

To a solution of 5.21g of 2(S)-methyl-3-mercaptopropionic acid t-butyl ester in 75 mL of toluene at 0° C. was added 4.50g of 1,8-diazabicyclo[5.40]undec-7-ene and 1.94 mL of methyl iodide. After stirring at room temperature for 2.5 hours, the volatiles were removed, ethyl acetate added, washed with dilute hydrochloric acid, water, brine, dried and concentrated to afford 2.82 g of a pale oil, identified as 2(S)-methyl-3-(thiomethyl)propionic acid t-butyl ester.

To a solution of 2.82 g of 2(S)-methyl-3-(thiomethyl) propionic acid t-butyl ester in 50 mL of acetic acid was added 5.58 g of sodium perborate and the mixture heated to 55° C. for 17 hours. The reaction was poured into water, extracted with methylene chloride, washed with aqueous sodium bicarbonate, dried and concentrated to afford 2.68 g of 2(S)-methyl-3-(methylsulfonyl)propionic acid t-butyl ester as a white solid.

To 2.68 g of 2(S)-methyl-3-(methylsulfonyl)propionic acid t-butyl ester was added 20 mL of 4N hydrochlorid acid/dioxane and the mixture stirred at room temperature for 19 hours. The solvent was removed under reduced pressure to afford 2.18 g of crude product, which was recrystallized from ethyl acetate/hexane to yield 1.44g of 2(S)-methyl-3-(methylsulfonyl)propionic acid as white crystals, mp 81°–83° C.

EXAMPLE 28

This example illustrates preparation of compounds of Formula IV wherein t is 1.

4-N-benzyl itaconamide

A 500 mL three necked round bottomed flask equipped with a dropping funnel, mechanical stirrer, nitrogen inlet and reflux condenser was charged with itaconic anhydride (33.6 g, 0.3 mol) and 150 mL of toluene. This solution was added a solution of benzylamine (32.1 g, 0.3 mol) in 50 mL of toluene dropwise over 30 m at room temperature. The solution was stirred at this temperature an additional 3h and then the solid product isolated by filtration on a Büjchner funnel. The crude product, 64.6 g 98%, was recrystallized from 300 mL of isopropyl alcohol to give after two crops 52.1 g, 79% of pure product, mp 149°–150 ° C.

2(R)-Methyl 4-N-benzyl succinamide

A large Fisher-Porter bottle was charged with the acid from the above reaction (10.95 g, 0.05 mol), rhodium (R,R)-DiPAMP (220 mg, 0.291 mmol) and 125 mL of degassed methanol. The solution was then hydrogenated at 40 psig for 16h at room temperature. After the hydrogen uptake ceased, the vessel was opened and the solution concentrated in vacuo to give a yellow solid, 11.05 g, 100%. The product was then taken up in absolute ethanol and allowed to stand whereupon crystals of the desired product formed, 7.98 g, 72%, mp 127°–129° C. [α]D @25° C.=+

14.9° (c=1.332, EtOH), $^1$H nmr (CDCl$_3$) 300 MHz 7.30(m, 5H), 6.80(brs, 1H), 4.41 (d, J=5.8 Hz, 2H), 2.94(m, 1H), 2.62(dd, J=8.1, 14.9Hz, 1H), 2.33(dd, J=5.5, 14.9 Hz, 1H), 1.23(d, J=7.2 Hz, 3H).

4-N-(4-methoxybenzyl)itaconamide

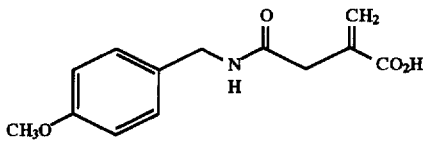

A 500 mL three necked round bottomed flask equipped with a dropping funnel, mechanical stirrer, nitrogen inlet and reflux condenser was charged with itaconic anhydride (44.8 g, 0.4 mol) and 150 mL of toluene. This solution was added a solution of 4-methoxybenzylamine (54.8 g, 0.4 mol) in 50 mL of toluene dropwise over 30 m at room temperature. The solution was stirred at this temperature an additional 2h and then the solid product isolated by filtration on a Büchner funnel. The crude product was recrystallized from ethyl acetate/ethanol to give after two crops 64.8 g, 65% of pure product, mp 132°–134° C., 1H nmr (CDCl$_3$) 300 MHz 7.09(d, J=9.1 Hz, 2H), 6.90(brt, J=5.9 Hz, 1H), 6.74(d, J=9.1 Hz, 2H), 6.22(s, 1H), 5.69(s, 1H), 4.24(d, J=5.9 Hz, 2H), 3.69(s, 3H), 3.15(s, 2H). $^{13}$C nmr (CDCl$_3$) 170.52, 169.29, 159.24, 135.61,131.08, 129.37, 128.97, 114.36, 55.72, 43.37, 40.58.

2(R)-Methyl 4-N-(4-methoxybenzyl)succinamide

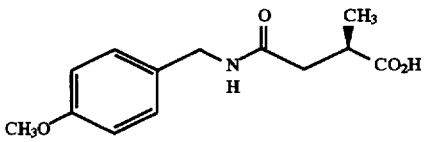

A large Fisher-Porter bottle was charged with the acid from the above reaction (5.00 g, 0.02 mol), rhodium (R,R)-DiPAMP (110 mg, 0.146 mmol) and 50 mL of degassed methanol. The starting acid was not completely soluble initially, but as the reaction progressed the solution became homogeneous. The solution was then hydrogenated at 40 psig for 16h at room temperature. After the hydrogen uptake ceased, the vessel was opened and the solution concentrated in vacuo to give a yellow solid. The crude product was then taken up in ethyl acetate and washed three times with sat. aq. NARCO$_3$ solution. The combined aqueous extracts were acidified to pH=1 with 3N HCl and then extracted three times with ethyl acetate. The combined ethyl acetate extracts were washed with brine, dried over anhyd. MgSO$_4$, filtered and concentrated to give the expected product as a white solid, 4.81 g, 95%. This material was recrystallized from a mixture of methyl ethyl ketone/hexane to give 3.80 g, 75% of pure product, [α]D @25° C.=+11.6° (c=1.572, MeOH). 1H nmr (CDCl$_3$) 300 MHz 11.9(brs, 1H), 7.18(d, J=9.2 Hz, 2H), 6.82(d, J=9.2 Hz, 2H), 6.68(brt, J=5.6 Hz, 1H), 4.33(d, J=5.6 Hz, 2H), 3.77(s, 3H), 2.92(ddq, J=7.9, 5.4, 7.3 Hz, 1H), 2.60(dd, J=5.4, 15.0 Hz, 1H), 2.30(dd, J=7.9, 15.0 Hz, 1H),1.22(d, J=7.3 Hz, 3H).

Butanediamide, N'-[3-[[[(1,1-dimethylethyl)amino]carbonyl](3-methylbutyl)amino]-2-hydroxy-1-(phenylmethyl)propyl]-N-4-methoxyphenylmethyl-2-methyl, [1S-[1R*(2R*),2S*]]-

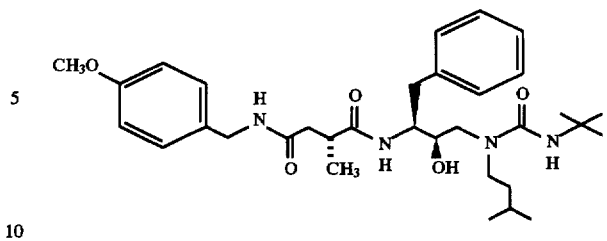

A 50 mL round bottomed flask was charged with 2(R)-methyl 4-N-(4-methoxybenzyl)succinamide (588 mg, 2.35 mmol), N-hydroxybenzotriazole (511 mg, 3.34 mmol) and 6 mL of DMF. The solution was cooled to 0° C. and treated with 1-(3-dimethylaminopropyl)-3-ethylcarbodiimide hydrochloride (502 mg, 2.62 mmol) for 20 m. A solution of (2R,3S)-3-amino-1-(3-methylbutyl)-1-[(1,1-dimethylethyl)amino]carbonyl)-4-phenyl-2-butanol (782 mg, 2.24 mmol) in 2 mL of DMF was added and the solution stirred at room temperature for a period of 24 h. The solution was concentrated in vacuo and poured into 50 mL of 50% sat. aq. NaHCO$_3$, the aqueous phase was extracted with CH$_2$Cl$_2$. The organic phase was washed with 5% citric acid, NaHCO$_3$, brine, dried over anhyd. MgSO$_4$, filtered and concentrated to give an oil that was purified by radial chromatography on SiO$_2$ eluting with hexane/ethyl acetate to give 790 mg, 59% of pure product as a white foam.

Butanediamide, N'-[3-[[[(1,1-dimethylethyl)amino]carbonyl](3-methylbutyl)amino]-2-hydroxy-1-(phenylmethyl)propyl]-N-phenylmethyl-2-methyl, [1S-[1R*(2R*),2S*]]-

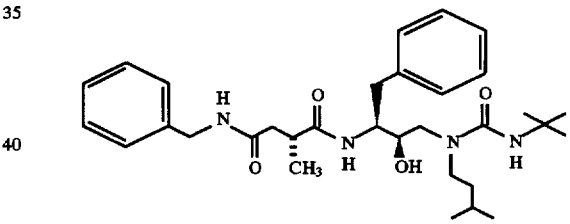

A 50 mL round bottomed flask was charged with 2(R)-methyl 4-N-(benzyl) succinamide (243 mg, 1.1 mmol), N-hydroxybenzotriazole (213 mg, 1.39 mmol) and 3 mL of DMF. The solution was cooled to 0° C. and treated with 1-(3-dimethylaminopropyl)-3-ethylcarbodiimide hydrochloride (228 mg, 1.17 mmol) for 20 m. A solution of (2R,3S)-3-amino-1-(3-methylbutyl)-1-[(1,1-dimethylethyl)amino]carbonyl)-4-phenyl-2-butanol (327 mg, 0.95 mmol) in 2 mL of DMF was added and the solution stirred at room temperature for a period of 24 h. The solution was concentrated in vacuo and poured into 50 mL of 50% sat. aq. NaHCO$_3$, the aqueous phase was extracted with CH$_2$Cl$_2$. The organic phase was washed with 5% citric acid, NaHCO$_3$, brine, dried over anhyd. MgSO$_4$, filtered and concentrated to give an oil that was purified by flash chromatography on SiO$_2$ eluting with hexane/ethyl acetate to give 370 mg, 70% of pure product as a white foam.

EXAMPLE 29

Following the procedure generally as set forth in Example 28, the compounds shown in Table 15 were prepared.

TABLE 15

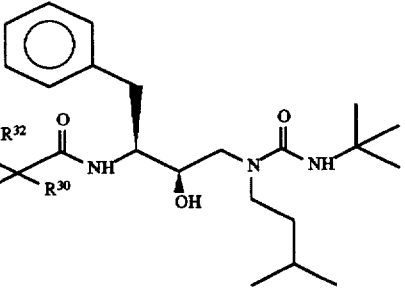

| R¹ | R³⁰ | R³¹ | R³² | X' | R³³ | R³⁴ |
|---|---|---|---|---|---|---|
| H | H | H | H | N | H | H |
| H | H | H | H | O | H | — |
| H | H | H | H | O | CH₃ | — |
| CH₃ | H | H | H | N | H | H |
| CH₃ | H | H | H | O | H | — |
| H | H | CH₃ | H | N | H | H |
| H | H | CH₃ | H | O | H | — |
| CH₃ | CH₃ | H | H | N | H | H |
| CH₃ | CH₃ | H | H | O | H | — |
| CH₃ | CH₃ | H | H | O | CH₂C₆H₄OCH₃ | — |
| H | H | CH₃ | CH₃ | N | H | H |
| H | H | CH₃ | CH₃ | O | H | — |
| H | H | CH₃ | CH₃ | O | CH₂C₆H₄OCH₃ | — |
| CH₃ | H | CH₃ | H | N | H | H |
| CH₃ | H | CH₃ | H | N | H | CH₃ |
| CH₃ | H | CH₃ | H | N | CH₃ | CH₃ |
| CH₃ | H | CH₃ | H | O | H | — |
| CH₃ | H | CH₃ | H | N | H | —CH₂C₆H₅OCH₃ |
| CH | H | H | H | N | H | H |
| CH | H | H | H | O | H | — |
| H | H | OH | H | N | H | H |
| H | H | OH | H | O | H | — |
| CH₂ | H | H | H | N | H | H |
| CH₂C(O)NH₂ | H | H | H | N | H | H |
| CH₂C(O)NH₂ | H | H | H | O | H | — |
| CH₂C(O)NH₂ | H | H | H | O | CH₃ | — |
| CH₂Ph | H | H | H | N | H | H |

EXAMPLE 30

Following the procedure generally as set forth in Example 28, the compounds shown in Table 16 were prepared.

TABLE 16

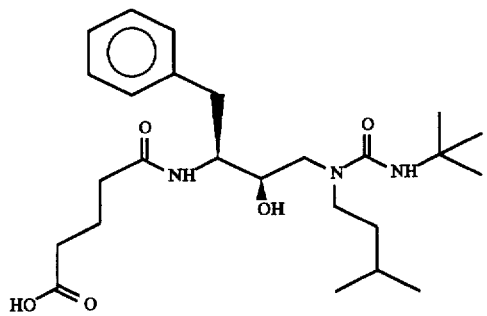

TABLE 16-continued

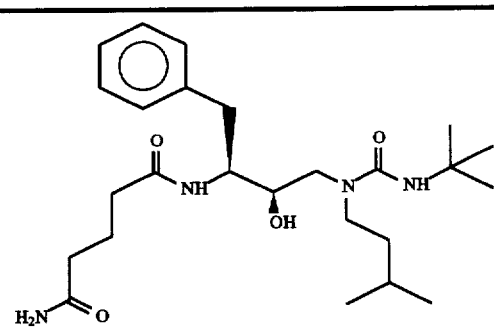

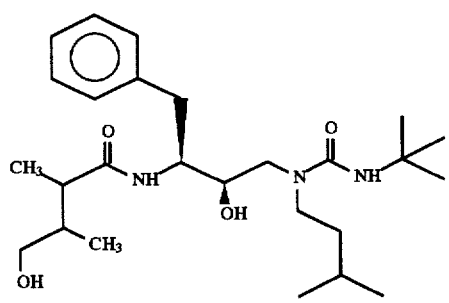

TABLE 16-continued

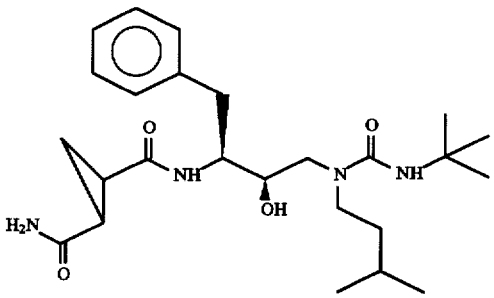

EXAMPLE 31

Preparation of 3(S)-[N-(2-quinolinylcarbonyl)-L-asparaginyl]amino-2(R)-hydroxy-4-phenylbutylamine. N-(3-methylbutyl).

Part A. Preparation of N-3(S)-(Benzyloxycarbonyl)-amino-2(R)-hydroxy-4-phenylbutylamine, N-(3-methylbutyl). A solution of 20 g (67 mmol) of N-benzyloxycarbonyl-3(S)-amino-1,2-(S)-epoxy-4-phenylbutane in 140 mL of isopropyl alcohol was treated with 83 g (952 mmol) of isoamylamine and refluxed for one hour. The solution was cooled, concentrated, hexane added and the resulting solid filtered to afford 22.4 g of the desired product.

Part B. Preparation of N-3(S)-(Benzyloxycarbonyl)-amino-2(R)-hydroxy-4-phenylbutylamine, N-(3-methylbutyl)-N-(t-butyloxycarbonyl). To a solution of 22.4 g (58.3 mmol) of product from Part A above, 6.48 g (64.1 mmol) of triethylamine and 150 mg of N,N-dimethyl-4-aminopyridine in 200 mL of tetrahydrofuran at 0° C. was added 12.7 g (58.3 mmol) of di-t-butylpyrocarbonate in 10 mL of THF. After 3.5 hours at room temperature, the volatiles were removed, ethyl acetate added and washed with 5% citric acid, sat'd NaHCO₃, dried and concentrated to afford 30 g of crude product. Chromatography on silica gel using 20% ethyl acetate/hexane afforded 22.5 g (79%) of the desired product.

Part C. Preparation of N-3(S)-[N-benzyloxycarbonyl-L-asparaginyl]amino-2(R)-hydroxy-4-phenylbutylamine, N-(3-methylbutyl)-N-(t-butyloxycarbonyl). A solution of 22.5 g of product from Part B above in 200 mL of ethanol was hydrogenated over 5.9 g of 10% palladium-on-carbon under 50 psig hydrogen for one hour. The catalyst was filtered and the solvent removed under reduced pressure to afford 15.7 g of free amine. This was dissolved in 130 mL of DMF and 4.54 g (44.9 mmol) of N-methylmorpholine an added to a mixture of 13.3 g (49.9 mmol) N-benzyloxycarbonyl-L-asparagine, 11.5 g (74.9 mmol) of N-hydroxybenzotriazole and 10.5 g (54.9 mmol) of EDC in 120 mL of DMF at 0° C., which had been preactivated for one hour prior to the addition. The mixture was stirred for 2 hours at 0° C. and then for 12 hours at room temperature. The reaction was poured into 1 L of sat'd aqueous sodium bicarbonate, the solid collected, dissolved in ethyl acetate, washed with water, sat'd sodium bicarbonate, 5% citric acid and brine, dried and concentrated to afford 16.7 g of the desired product.

Part D. Preparation of N-3(S)-[N-(2-quinolinylcarbonyl)-L-asparaginyl]amino-2(R)-hydroxy-4-phenylbutylamine, N-(3-methylbutyl)-N-(t-butyloxycarbonyl). A solution of 16.7g (28.0 mmol) of product from Part C in 250 mL of methanol was hydrogenated over 6.0 g of 10% palladium-on-carbon and under 50 psig hydrogen for one hour. The catalyst was filtered and the solution concentrated to afford 10.0 g of free amine. This was dissolved in 100 mL of methylene chloride, 4.35 g (43 mmol) of N-methylmorpholine was added followed by 5.53 g (20.5 mmol) of quinoline-2-carboxylic acid, N-hydroxysuccinimide ester. This was stirred at room temperature overnight, the solvent removed, ethyl acetate added and washed with 5% citric acid, sat'd sodium bicarbonate, brine, dried and concentrated to afford 14 g of crude product. Recrystallization from ethyl acetate and hexane afforded 10.5 g (83%) of desired product.

Part E. Preparation of N-3(S)-[N-(2-quinolinyl-carbonyl)-L-asparaginyl]amino-2(R)-hydroxy-4-phenylbutylamine, N-(3-methylbutyl). To 80 mL of 4N hydrochloric acid in dioxane was added 9.17 g (14.8 mmol) of product from Part D above. After one hour, the product becomes gummy. The solvents were removed, diethyl ether added and removed and the residue dissolved in 20 mL of methanol. This solution was added to 400 mL of sat'd aqueous sodium bicarbonate, the solids collected, washed with acetone and hexane and dried in vacuo over P₂O₅ to afford 4.75 g of the desired product.

EXAMPLE 32A

Preparation of Benzyl 2,2,3(R)-trimethylsuccinate

Part A: Preparation of Methyl(S)-lactate, 2-methoxy-2-propyl ether. To a mixture of methyl(s)-(−)-lactate (13.2 g, 100 mmol) and, 2-methoxypropene (21.6 g, 300 mmol) in CH₂Cl₂ (150 ml) was added POCl₃ (7 drops) at r.t. and the resulting mixture was stirred at this temperature for 16 hours. After the addition of Et₃N (10 drops), the solvents were removed in vacuo to give 20.0 g of (98%) desired product.

Part B. Preparation of 2(S)-hydroxypropanal, 2-methoxy-2-propyl ether. To a solution of compound from Part A (20.0 g) in CH₂Cl₂ (100 ml) was added DIBAL (65 ml of 1.5M solution in toluene, 97.5 mmol) dropwise at −78° C. for 45 min., then stirring was continued at the temperature for another 45 min. To this cold solution was added MeOH (20 ml), saturated NaCl solution (10 ml) and allowed the reaction mixture to warm up to r.t. and diluted with ether (200 ml), MgSO₄ (150 g) was added and stirred for another 2 h. The mixture was filtered and the solid was washed twice with ether. The combined filtrates were rotavaped to afford 11.2 g (78%) of the desired aldehyde.

Part C. Preparation of 2(S)-hydroxy-cis-3-butene, 2-methoxy-2-propyl ether. To a suspension of ethyltriphenylphosphonium bromide (28 g, 75.5 mmol) in THF (125 ml) was added KN (TMS)₂ (15.7 g, 95%, 75 mmol) in portions at 0° C. and stirred for 1 h at the temperature. This red reaction mixture was cooled to −78° C. and to this was added a solution of aldehyde from Part B (11 g, 75 mmol) in THF (25 ml). After the addition was completed, the resulting reaction mixture was allowed to warm up to r.t. and stirred for 16 h. To this mixture was added saturated NH₄Cl (7.5 ml) and filtered through a pad of celite with a thin layer of silica gel on the top. The solid was washed twice with ether. The combined filtrates were concentrated in vacuo to afford 11.5 g of crude product. The purification of crude product by flash chromatography (silica gel, 10:1 Hexanes/EtAc) affording 8.2 g (69%) pure alkene.

Part D. Preparation of 2(S)-hydroxy-cis-3-butene. A mixture of alkene from Part C (8.2 g) and 30% aqueous acetic acid (25 ml) was stirred at r.t. for 1 hour. To this mixture was added NaHCO₃ slowly to the pH~7, then extracted with ether (10 ml×5). The combined ether solutions were dried (Na₂SO₄) and filtered. The filtrate was distilled to remove the ether to give 2.85 g (64%) pure alcohol, m/e=87(M+H).

Part E. Preparation of 2,2,3(S)-trimethyl-hex-(trans)-4-enoic acid. To a mixture of alcohol from Part D (2.5 g, 29 mmol) and pyridine (2.5 ml) in CH2Cl2 (60 ml) was added isobutyryl chloride (3.1 g, 29 mmol) slowly at 0° C. The resulting mixture was stirred at r.t. for 2 hours then washed with H₂O (30 ml×2) and sat. NaCl (25 ml). The combined organic phases were dried (Na₂SO₄), concentrated to afford 4.2 g (93%) ester 2(S)-hydroxy-cis-3-butenyl isobutyrate. This ester was dissolved in THF (10 ml) and was added to a 1.0M LDA soln. (13.5 ml of 2.0M LDA solution in THF and 13.5 ml of THF) slowly at −78° C. The resulting mixture was allowed to warm up to r.t. and stirred for 2 h and diluted with 5% NaOH (40 ml). The organic phase was separated, the aqueous phase was washed with Et2O (10 ml). The aqueous solution was collected and acidified with 6N HCl to pH~3. The mixture was extracted with ether (30 ml×3). The combined ether layers were washed with sat. NaCl (25 ml), dried (Na₂SO₄) and concentrated to afford 2.5 g (60%) of desired acid, m/e=157(M+H).

Part F. Preparation of benzyl 2,2,3(S)-trimethyl-trans-4-hexenoate. A mixture of acid from Part E (2.5 g, 16 mmol), BnBr (2.7 g, 15.8 mmol), K₂CO₃ (2.2 g, 16 mmol), NaI (2.4 g) in acetone (20 ml) was heated at 75° C. (oil bath) for 16 h. The acetone was stripped off and the residue was dissolved in H₂O (25 ml) and ether (35 ml). The ether layer was separated, dried (Na₂SO₄) and concentrated to afford 3.7 g (95%) of benzyl ester, m/e=247(M+H).

Part G. Preparation of benzyl 2,2,3(R)-trimethylsuccinate. To a well-stirred mixture of KMnO₄ (5.4 g, 34, 2 mmol), H₂O (34 ml), CH₂Cl₂ (6 ml) and benzyltriethylammonium chloride (200 mg) was added a solution of ester from Part F (2.1 g, 8.54 mmol) and acetic acid (6 ml) in CH₂Cl₂ (28 ml) slowly at 0° C. The resulting mixture was stirred at the temperature for 2 h then r.t. for 16 h. The mixture was cooled in an ice-water bath, to this was added 6N HCl (3 ml) and solid NaHSO₃ in portions until the red color disappeared. The clear solution was extracted with CH₂Cl₂ (30 ml×3). The combined extracts were washed with sat. NaCl solution, dried (Na₂SO₄) and concentrated to give an oil. This oil was dissolved in Et2O (50 ml) and to this was added sat. NaHCO₃ (50 ml). The aqueous layer was separated and acidified with 6N HCl to pH~3 then extracted with Et2O (30 ml×3). The combined extracts were washed with sat. NaCl solution (15 ml), dried (Na₂SO₄) and concentrated to afford 725 mg (34%) of desired acid, benzyl 2,2,3(R)-trimethylsuccinate, m/e=251(M+H).

EXAMPLE 32B

Part A.

Preparation of Butanediamide, N¹[3-[[[(1,1-dimethylethyl)amino]carbonyl](3-methylbutyl)amino]-2-hydroxy-1-(phenylmethyl)propyl]-2,3-trimethyl-[1-S-, [1R*(2S*),2S*]]-.

To a well-stirred solution of acid benzyl 2,2,3(R)-triemthylsuccinate (225 mg, 0.9 mmol) in DMF (1.0 ml) was added HOBt (230 mg, 1.5 mmol). The clear reaction mixture was then cooled to 0° C., to this was added EDC (210 mg, 1.1 mmol) and stirred for 1 h at the temperature. To this cold mixture was added a powder of (350 mg, 1.0 mmol) and DMF (0.5 ml). The resulting reaction mixture was stirred for 2 h at 0° C. and 16 h at r.t. After the removal of DMF (≦40° C.), a solution of 60% sat. NaHCO₃ (10 ml) was added. This mixture was extracted with EtOAc (10 ml×2). The extracts were combined and washed with sat. NaHCO₃ (10 ml×2), 5% citric acid (10 ml×2), H₂O (10 ml), sat. NaCl (10 ml) and dried (Na₂SO₄) then concentrated to afford 512 mg (98%) of desired product Butanoic Acid, 4-[[3-[[[(1,1-dimethylethyl) amino]carbonyl](3-methylbutyl)amino]-2-hydroxy-1-(phenylmethyl)propyl]amino]-2,2,3-trimethyl-4-oxo, [1S-[1R*(3S*),2S*]]-benzyl ester as a white solid, m/e=582(M+H).

Part B. A mixture of benzyl ester from Part A (480 mg, 0.825 mmol), 10% Pd/C (450 mg) in MeOH (25 ml) was hydrogenated (H₂, 50 psi) for 1/2 h at r.t. The mixture was filtered and the solid was washed with MeOH (10 ml). The collected filtrates were concentrated to afford a crude acid as a white solid. The crude acid was dissolved in Et2O-EtOAc (10:1, 25 ml) and the solution was washed with sat. NaHCO3 (25 ml) then 5% NaOH (10 ml). The combined aqueous layers were cooled to 0° C. and acidified with concentrated HCl (Co₂) to pH~1 then extracted with Et₂O-EtOAC (10:1, 25 ml×3). The combined extracts were washed with sat. NaCl (15 ml), dried (Na₂SO₄) and concentrated to afford 307 mg (75.7%) of pure acid Butanoic acid, 4-[[3-[[[(1,1-dimethylethyl)amino]carbonyl](3-methylbutyl)amino]-2-hydroxy-1-(phenylmethyl)propyl]amino]-2,2,3-trimethyl-4-oxo-,[1S-[1R*(3S*),2S*]]-, as a white solid, m/e=491(M+H).

Part C. Butanoic acid, 4-[[3-[[[(1,1-dimethylethyl)amino carbonyl](3-methylbutyl)amino]-2-hydroxy-1-(phenylmethyl)propyl]amino]-2,2,3-trimethyl-4-oxo-,[1S-[1R*(3S*),2S*]]-, as a white solid, m/e=491(M+H).

To a well-stirred solution of the acid from Part B (245 mg, 0.5 mmol) in DMF (0.5 ml) was added HOBt (153 mg, 1.0 mmol) and EDC (143 mg, 0.75 mmol) at 0° C. After stirring at 0° C. for 2 h, NH₄OH (0.63 ml of 28% NH₄OH, 5 mmol) was added and stirred at 0° C. for 2 h, r.t. for 16 h. The removal of DMF (<40° C.) gave a white solid. The purification of the crude product by flash chromatography (silica gel, 5% MeOH/CH₂Cl₂) gave 172 mg (70%) of pure amide 12 as a white solid, m/e=491 (M+H).

EXAMPLE 33

Preparation of methyl 2,2-dimethyl-3-methyl succinate, (R) and (S) isomers

Part A. Preparation of methyl 2,2-dimethyl-3-oxo-butanoate. A 250 ml RB flask equipped with magnetic stir bar and N₂ inlet was charged with 100 ml dry THF and 4.57 g (180 mmol) of 95% NaH. The slurry was cooled to −20° C. and 10g (87 mmol) methyl acetoacetate was added dropwise followed by 11.3 ml (181 mmol) CH₃I. The reaction was stirred at 0° C. for 2 hours and let cool to room temperature overnight. The reaction was filtered to remove NaI and diluted with 125 ml Et₂O. The organic phase was washed with 1×100 1 5% brine, dried and concentrated in vacuo to a dark golden oil that was filtered through a 30 g plug of silica gel with hexane. Concentration in vacuo yielded 10.05 g of desired methyl ester, as a pale yellow oil, suitable for use without further purification.

Part B. Preparation of methyl 2,2-dimethyl-3-0-(trifluoromethanesulfonate)-but-3-enoate. A 250 ml RB flask equipped with magnetic stir bar and N₂ inlet was charged with 80 1 by THF and 5.25 mL (37.5 mmol) diisopropylamine was added. The solution was cooled to −25° C. (dry ice/ethylene glycol) and 15 ml (37.5 mmol) of 2.5M nbuLi in hexanes was added. After 10 minutes a solution of 5 g (35 mmol) of the compound from Part A in 8 ml dry THF was added. The deep yellow solution was stirred at −20° C. for 10 min. then 12.4 g N-phenyl bis (trifluoromethanesulfonimide) (35 mmol) was added. The reaction was stirred @−10° C. for 2 hours, concentrated in vacuo and partioned between ethyl acetate and sat NaHCO$_3$. The combined organic phase was washed with NaHCO$_3$, brine and conc. to an amber oil that was filtered through 60 g silica gel plug with 300 300 mL of 5% ethyl acetate/hexane. Conc. in vacuo yielded 9.0 g light yellow oil that was diluted with 65 ml EA and washed with 2×50 ml 5% aq K$_2$CO$_3$, brine, dried over Na$_2$SO$_4$ and conc. in vacuo to yield 7.5 g (87%) vinyl triflate, (m/e=277(M+H) suitable for use without further purification.

Part C. Preparation of methyl 2,2-dimethyl-3-carboxyl-but-3-enoate. A 250 mL Fisher Porter bottle was charged with 7.5 g (27 mmol) the compound from Part B, 50 ml dry DMF, 360 mg (1.37 mmol) triphenylphosphine and 155 mg (0.69 mmol) Pd(OAc)$_2$. The reaction mixture was purged twice with N$_2$ then charged with 30 psi CO. Meanwhile a solution of 20 ml dry DMF and 7.56 ml (54 mmol) NEt$_3$ was cooled to 0° C. to this was added 2.0 g (43 mmol) of 99% formic acid. The mixture was swirled and added to the vented Fisher Porter tube. The reaction vessel was recharged to 0 psi of CO and stirred 6 hours at room temperature. The reaction mixture was concentrated in vacuo and partioned between ethyl acetate and 5% aq K$_2$CO$_3$. The aqueous phase was washed with an additional portion of ethyl acetate and then acidified with 12N. HCl. The aqueous phase was extracted with ethyl acetate and the organics were dried and concentrated in vacuo. to yield 3.5 g (75%) white crystals, mp 72°–75° C., identified as the desired product (m/e=173 (M+H).

Part D. Preparation of methyl 2,2-dimethyl-3-methylsuccinate, isomer #1. A steel hydrogenation vessel was charged with 510 mg (3.0 mmol) acrylic acid, from Part C, and 6 mg Ru (acac)2 (R-BINAP) in 10 ml degassed MeOH. The reaction was hydrogenated at 50 psi/room temperature for 12 hours. The reaction was then filtered through celite and conc. to 500 mg clear oil which was shown to be a 93:7 mixture of isomer #1 and #2, respectively as determined by GC analysis using a 50M β-cyclodextrin column: 150° C.—15 min. then ramp 2° C./min.; isomer #1, 17.85 min., isomer #2, 18–20 min.

Part E. Preparation of methyl 2,2-dimethyl-3-methylsuccinate, Isomer #2. A steel hydrogenation vessel was charged with 500 mg (2.9 mmol) acrylic acid, from Part C, and 6 mg Ru(OAc) (acac)(S-BINAP) in 10 ml degassed MeOH. The reaction was hydrogenated at 50 psi/room temperature for 10 hours. The reaction was filtered through celite and concentrated in vacuo to yield 490 mg of product as a 1:99 mixture of isomers #1 and #2, respectively, as determined by chiral GC as above.

EXAMPLE 34

Preparation of 3-[[[(1,1-dimethylethyl)amino] carbonyl](3-methylbutyl)amino]-2(R)-hydroxy-1(S)-(phenylmethyl)propylamine, 1

Part A. To a solution of 75.0 g (0.226 mol) of N-benzyloxycarbonyl-L-phenylalanine chloromethyl ketone in a mixture of 807 mL of methanol and 807 mL of tetrahydrofuran at −2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1 L). The solution was washed sequentially with 1M potassium hydrogen sulfate, saturated sodium bicarbonate and then saturated sodium chloride solution. After drying over anhydrous magnesium sulfate and filtering, the solution was removed under reduced pressure. To the resulting oil was added hexane (approx. 1 L) and the mixture warmed to 60° C. with swirling. After cooling to room temperature, the solids were collected and washed with 2 L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150°–151° C. and M+Li+=340.

Part B. To a solution of 6.52 g (0.116 mol, 1.2 equiv.) of potassium hydroxide in 968 mL of absolute ethanol at room temperature, was added 32.3 g (0.097 mol) of N-CBZ-3(S)-amino-1-chloro-4-phenyl-2(S)-butanol. After stirring for fifteen minutes the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl-3(S)-amino-1, 2(S)-epoxy-4-phenylbutane, mp 102°–103° C. and MH+298.

Part C. A solution of N-benzyloxycarbonyl 3(S)-amino-1,2-(S)-epoxy-4-phenylbutane (30.1 g, 0.10 mol) and 165mL of isoamylamine in 150 mL of isopropyl alcohol was heated to reflux for 2.5 hours. The solution was cooled to room temperature, concentrated/n vacuo and then recrystallized. The product was isolated by filtration and from ethylacetate/hexane to afford 1.7 g (81%) of N[3(S)-benzyloxycarbonylamino-2(R)-hydroxy-4-phenylbutyl]N-isoamylamine.

Part D. A solution of N[3(S)-benzyloxycarbonylamino-2(R)-hydroxy-4-phenyl butyl], N-isoamylamine in 10 ml of tetrahydrofuran was treated with tert-butylisocyanate (267 mg, 2.70 mmol) at room temperature for 5 minutes. The solvent was removed in vacuo and replaced with ethyl acetate. The ethyl acetate solution was washed with 5% citric acid, water, and brine, dried over anhydrous MgSO$_4$, filtered and concentrated in vacuo to give 1.19 g, 97% of N-benzyloxycarbonyl-3-[[[(1,1-dimethylethyl)amino] carbonyl](3-methylbutyl)amino]-2(R)-hydroxy-1 (S)-(phenylmethyl)propylamine, MH+m/z=470.

Part E. A solution of (37.3 g, 77 mmol) of product from Part D in 100 mL of methanol was hydrogenated over 10% palladium-on-carbon for 4 hours to afford 26.1 g of the desired final product.

EXAMPLE 35

Preparation of butanediamide, M-[3-[[[(1,1-dimethylethyl)amino]carbonyl](3-methylbutyl) amino]-2-hydroxy-1-(phenylmethyl)propyl]-, [1S-[1R*, 2S*]]-.

Part A. To a solution of 102 mg (0.29 mmol) of the compound from Example 34, Part E, and 70 mg (0.89 mmol) of pyridine in 2 mL of methylene chloride was added 29 mg (0.29 mmol) of succinic anhydride. After 2 hours, ethyl acetate was added and then extracted with saturated NaHCO$_3$. The aqueous layer was acidified, reextracted with ethyl acetate, washed with saturated brine, dried over magnesium sulfate, filtered and concentrated in vacuo to afford 78 mg (60%) of butanoic acid, 4-[[3-[[[(1,1-dimethylethyl) amino]carbonyl](3-methylbutyl)amino]-2-hydroxy--(phenylmethyl)propyl]amino-4-oxo-, [1 S-[1R*, 2S*]-.

Part B. This was activated with EDC and N-hydroxybenzotriazole in N,N-dimethylformamide and then reacted with ammonia to generate the desired final compound.

EXAMPLE 36

Part A. To a solution of 4.60 g (24.7 mmol) of trans-diethyl 1,2-cyclopropanedicarboxylate in 100 mL of 50:50 v:v tetrahydrofuran/water was added 1.24 g (29.6 mmol) of lithium hydroxide. After 17 hours, the tetrahydrofuran was removed in vacuo, the water layer washed with ethyl acetate, acidified with 1N hydrochloric acid and reextracted with ethyl acetate. The organic layer was dried and stripped to afford 2.1 g of crude product. After recrystallization from diethyl ether/hexane and then methylene chloride/hexane one obtains 1.1 g (28%) of transmonoethyl 1,2-cyclopropanedicarboxylate, m/e=159 (M+H).

Part B. To a solution of 297 mg (1.87 mmol) of trans-monoethyl 1,2-cyclopropanedicarboxylate and 429 mg (2.8 mmol) N-hydroxybenzotriazole (HOBT) in 3 mL of anhydrous N,N-dimethylformamide (DMF) at 0° C. was added 394 mg (2.0 mmol) of 1-(3-dimethylamino-propyl)-3-ethylcarbodiimide hydrochloride (EDC). After 30 min. a solution of 591 mg (1.7 mmol) of the compound from Part A in 2 mL DMF and 171 mg (1.69 mmol) of N-methylmorpholine (NMM) was added. After 2 hours at 0° C., the reaction was stirred at RT overnight, poured into water, extracted with ethyl acetate, washed with water, 5% aq. citric acid, sat'd NaHCO$_3$, brine, dried and stripped to afford 771 mg of crude product. This was chromatographed on silica gel using 5–20% methanol/methylene chloride to afford 670 mg (80%) of cyclopropanecarboxylic acid, 2-[[[3-[[[(1,1-dimethylethyl)amino]carbonyl](3-methylbutyl)amino]-2-hydroxy-1-(phenylmethyl)propyl]amino]carbonyl]-, ethyl ester; m/e-490 (M+H).

Part C. To a solution of 658 mg (1.32 mmol) of product from part B in 5 mL of 50:50 THF/water was added 66 mg (1.58 mmol) of lithium hydroxide. After 19 hours, the THF was removed in vacuo, the water washed with ethyl acetate, acidified and reextracted with ethyl acetate. The organic layer was dried and stripped to afford 328 mg (54%) of the corresponding acid, m/e=62 (M+H).

Part D. To a solution of 304 mg (0.66 mmol) of product from part C, 151 mg (0.99 mmol) HQBT in 2.2 mL DMF at 0° C. was added 139 mg (0.73 mmol) EDC. After 30 min. at 0° C., 1.1 mL of conc. aqueous ammonia was added. After stirring at 0° C. for 2 hours and RT for 20 hours, the reaction was poured into sat'd brine and extracted with ethyl acetate. After washing with sat'd NaHCO$_3$, sat'd brine, drying and stripping, one obtains 141 mg of crude product. This was chromatographed on silica gel with 1–5% methanol/methylene chloride to afford 40 mg (13%) of the desired final product, m/e=561 (M+H).

EXAMPLE 37

Preparation of trans-but-2-enediamide, N[3[[[(1,1-dimethylethyl)amino]carbonyl](3-methylbutyl)amino]-2-hydroxy-1-(phenylmethyl)propyl]-, [1S-[1R*, 2S*]

Part A. To a solution of 137 mg (0.95 mmol) fumaric acid monoethyl ester in 1 mL of DMF at 0° C. was added 183 mg (0.95 mmol) EDC. After 15 minutes, a solution of 333 mg (0.95 mmol) of the compound from Example 34, Part E, in 1 mL DMF was added and the reaction stirred for 14 hours at RT. Ethyl acetate was added and extracted with sat'd brine, 0.2 n HCl, sat'd NaHCO$_3$, dried and stripped to afford 0.32 g of crude product. Chromatography on silica gel using 0–50% ethyl acetate/hexane afforded 0.26 g (58%) of but-2-enoic acid, 4-[[3-[[[(1,1-dimethylethyl)amino]carbonyl](3-methylbutyl)amino]-2-hydroxy-1-(phenylmethyl)propyl]amino]-4-oxo-, [1S-[1R*, 2S*]]-, ethyl ester, m/e=476 (M+H).

Part B. To a solution of 26.6 mg (0.56 mmol) of product from part A in 3 mL of 50:50 THF/water was added 34 mg (0.82 mmol) of lithium hydroxide and the reaction stirred at RT for 1 hour. The THF was removed in vacuo, the aqueous layer acidified with 1N HCl and extracted with ethyl acetate. The organic layer was washed with brine, dried and stripped to afford 233 mg (93%) of trans-but-2-enoic acid, 4-[[3-[[[(1,1-dimethylethyl)amino]carbonyl](3-methylbutyl)amino]-2-hydroxy-1-(phenylmethyl)propyl]amino]-4-oxo-, [1S-[1R*, 2S*]-, m/e=448 (M+H).

Part C. In 1 mL of DMF was added 95 mg (0.50 mmol) EDC. After 15 minutes at RT, 0.50 mL of conc. aqueous ammonia was added and the reaction stirred for 15 hours. Ethyl acetate was added and washed with 0.2N HCl, brine, dried and stripped to afford 170 mg of crude product. After chromatography on silica gel using 0–40% methanol/methylene chloride, one obtains 50 mg (22%) of trans-but-3-enediamide, N-[3-[[[(1,1 -dimethylethyl)amino]carbonyl](3-methylbutyl)amino]-2-hydroxy-1-(phenylmethyl)propyl]-, [1S-[1R*, 2S*]-, m/e=447 (M+H).

EXAMPLE 38

Preparation of butanediamide, N-[3-[[[(1,1-dimethylethyl)amino]carbonyl](3-methylbutyl)amino]-2-hydroxy-1-(phenylmethyl)propyl-2-methyl-, [1S-[1R*(2S*), 2S*]-.

Part A. To a suspension of 24.7 g (0.22 mol) of itaconic anhydride in 100 mL of anhydrous toluene at reflux under a nitrogen atmosphere was added dropwise over 30 minutes 23.9 g (0.22 mol) of benzyl alcohol. The insoluble material dissolved to provide a homogeneous solution which was refluxed for 1.5 hours. The solution was cooled to RT, then in an ice bath and the resulting white precipitate collected by filtration to afford 24.8 g (51%) of 4-benzyl itaconate.

Part B. To a solution of 2.13 g (9.5 mmol) of the product from part A in 12 mL of methylene chloride at 0° C. was added 4.02 g (29.1 mmol) of para-methoxybenzyl alcohol, 605 mg (4.95 mmol) of N,N-dimethyl 4-aminopyridine, 128 mg of N,N-dimethyl 4-aminopyridine hydrochloride salt and then 2.02 g (4.7 mmol) dicyclohexylcarbodiimide (DCC). After stirring at 0° C. for 1 hour and then RT for 2 hours, the precipitate was collected and discarded. The filtrate was washed with 0.5N HCl, sat'd NaHCO$_3$, dried and stripped to afford 4.76 g of crude product. This was chromatographed on silica gel using 0–50% ethyl acetate/hexane to afford 1.24 g of pure 4'-methoxybenzyl-4-benzylitaconate.

Part C. A solution of 1.24 g (3.65 mmol) of product from part B and 20 mg of [(R,R)-Dipamp)cyclooctadienylrhodium] tetrafluoroborate in 30 mL of methanol was throughly degassed, flushed with nitrogen and then hydrogen and then stirred under 50 psig of hydrogen for 15 hours. The solution was filtered and stripped, dissolved in methylene chloride and washed with sat'd NaHCO$_3$, dried and stripped to afford 0.99 g of a brown oil. This was then dissolved in 40 mL of methylene chloride, 3 mL of trifluoroacetic acid added and the solution stirred at RT for 3.5 hours. Water was added and separated and the organic layer extracted with sat'd NaHCO$_3$. The aqueous layer was acidified and reextracted with ethyl acetate, separated and the organic layer washed with brine, dried and stripped to afford 320 mg (50%) of 2(R)-methyl-4-benzylsuccinic acid.

Part D. To a solution of 320 mg (1.44 mmol) of product from part C and 314 mg (2.05 mmol) HOBT in DMF at 0° C. was added 303 mg (1.58 mmol) of EDC. After stirring for 30 minutes, a solution of 467 mg (1.34 mmol) of 1 in 4 mL of DMF was added. After stirring for 1 hour at 0° C. and 14 hours at RT, ethyl acetate was added and washed with sat'd NaHCO$_3$, 5% aqueous citric acid, dried and stripped to afford 0.97 g of crude product. This was chromatographed on silica gel using 0–10% ethyl acetate/hexane to afford 420 mg of pure butanoic acid, 4-[[3-[[[(1,1-dimethylethyl) amino]carbonyl](3-methylbutyl)amino]-2-hydroxy-1 -(phenylmethyl)propyl]amino]-3-methyl-4-oxo-, [1 S-[1 R*(3S*), 2S*]-, benzyl ester.

Part E. A solution of 150 mg (0.27 mmol) of product from part D in 15 mL of methanol was hydrogenated over 10% palladium on carbon under 50 psig hydrogen for 17 hours. The reaction was filtered and stripped to afford 125 mg (100%) of butanoic acid, 4-[[3-[[[(1,1 -dimethylethyl) amino]carbonyl](3-methylbutyl)amino]-2-hydroxy-1-(phenylmethyl)propyl]amino]-3-methyl-4-oxo-, [1S-[1R*(3S*), 2S*]-.

Part F. To a solution of 125 mg (0.27 mmol) of product from part E and 65 mg (0.42 mmol) of HOBT in 5 mL of DMF at 0° C. was added 59 mg (0.31 mmol) of EDC. After 30 min. at 0° C., 1 mL of conc. aqueous ammonia was added. After stirring at 0° C. for 2 hours and RT fro 15 hours, ethyl acetate was added and washed with sat'd $NaHCO_3$, 5% aqueous citric acid, dried and stripped to afford 90 mg of crude product. This was recrystallized from ethyl acetate/ hexane to afford 40 mg (32%) of pure butanediamide, N-[3-[[[(1,1-dimethylethyl)amino]carbonyl](3-methylbutyl)amino]-2-hydroxy-1 -(phenylmethyl)propyl]-2-methyl, [1S-[1R*(2S*), 2S*]-.

EXAMPLE 39 preparation of butanediamide, N-[3-[[[(1,1-dimethylethyl)amino]carbonyl](3-methylbutyl) amino]-2-hydroxy-1-(phenylmethyl)propyl]2-methyl, [1S-[1R*(2R*), 2S*]-.

Part A. A solution of 1.41 g (4.1 mmol) of 4-methoxybenzyl 4-benzylitaconate and 25 mg of [(S,S-Dipamp) cyclooctadienylrhodium]tetrafluoroborate in 20 mL of methanol was thoroughly degassed, flushed with nitrogen and then hydrogen and then stirred under 40 psig hydrogen for 72 hours. The solution was filtered and concentrated to provide 1.34 g of a brown oil. This was dissolved in 40 mL of methylene chloride and 3 mL of trifluoroacetic acid was added. After stirring for 4 hours, water was added, separated and the organic layer extracted with sat'd $NaHCO_3$. The aqueous layer was separated, reacidified, extracted with ethyl acetate which was separated, washed with brine, dried and stripped to afford 440 mg of 2(S)-methyl-4-benzylsuccinic acid.

Part B. To a solution of 440 mg (1.98 mmol) of the product from part A and 437 mg (2.86 mmol) of HOBT in 9 mL of DMF at 0° C. was added 427 mg (2.23 mmol) of EDC. After 30 minutes at 0° C., a solution of 653 mg (1.87 mmol) of 1 in 3 mL DMF was added. After 1 hour at 0° C. and 15 hours at RT, ethyl acetate was added, extracted with sat'd $NaHCO_3$, 5% aqueous citric acid, dried and concentrated to afford 0.98 g of crude product. Chromatography on silica gel using 0–10% ethyl acetate afforded 610 mg (59%) of pure butanoic acid, 4-[[3-[[[(1,1-dimethylethyl)-amino]carbonyl] (3- methylbutyl)amino]-2-hydroxy- 1-(phenylmethyl) propyl]amino]-3-methyl-4-oxo-, [1 S-[1R*(3R*), 2S*], benzyl ester.

Part C. A solution of 310 mg (0.56 mmol) of the product from part B in 20 mL of methanol was hydrogenated over 20 mg of 10% palladium on carbon under 50 psig hydrogen for 19 hours. The solution was filtered and concentrated to afford 220 mg (85%) of butanoic acid, 4-[[3-[[[(1,1-dimethylethyl)-amino]carbonyl](3-methylbutyl)amino]-2-hydroxy-1-(phenylmethyl)propyl]amino]-3-methyl-4-oxo-, [1S-[1R*(3R*), 2S*].

Part D. To a solution of 190 mg (0.41 mmol) of the product from part C and 90 mg (0.58 mmol) HOBT in 5 mL of DMF at 0° C., was added 88 mg (0.46 mmol) of EDC. After 30 minutes at 0° C., 2 mL of conc. aqueous ammonia was added. After 1 hour at 0° C. and 15 hours at RT, ethyl acetate was added, washed with sat'd $NaHCO_3$, 5% aqueous citric acid, dried and concentrated to afford crude product. Recrystallization from ethyl acetate/hexane afforded 20 mg (11%) of butanediamide, N-[3-[[[(1,1-dimethylethyl)amino] carbonyl](3-methylbutyl)amino]-2-hydroxy-1-(phenylmethyl)propyl]-2-methyl, [1 S-[1R*(2R*), 2S*]-.

EXAMPLE 40

Preparation of butanediamide, N-[3-[[[(1,1-dimethylethyl)amino]carbonyl](3-methylbutyl) amino]-2-hydroxy-1-(phenylmethyl)propyl]-3-methyl-, [1S-[1R*(3S*), 2S*]-.

Part A. In a similar manner to the procedure used above, p-methoxybenzyl alcohol was reacted with itaconic anhydride in refluxing toluene to provide 4-(p-methoxybenzyl) itaconate.

Part B. To a solution of 3.30 g (13.2 mmol) of the product from part A in 17 mL of toluene, was added 2.08 g (13.7 mmol) of 1,8-diazabicyclo[5.40]undec-7-enc and then 2.35 g (13.7 mmol) of benzyl bromide. After 2 hours, the solution was filtered and the filtrate washed with sat'd $NaHCO_3$, 3N HCl, brine, dried and concentrated to afford 3.12 g of an oil. After chromatography on silica gel using 0–5% ethyl acetate/hexane one obtains 2.19 g (49%) of benzyl 4-(4-methoxybenzyl)itaconate.

Part C. A solution of 1.22 g (3.6 mmol) of product from part B and 150 mg of [((R,R-Dipamp)) cyclooctadienylrhodium] tetrafluoroborate in 15 mL of methanol was thoroughly degassed, flushed with nitrogen and then hydrogen and hydrogenated under 50 psig for 16 hours. The solution was filtered and concentrated to afford 1.2 g of a brown oil. This was dissolved in 5 mL of methylene chloride and 5 mL of toluene and 3 mL of trifluoroacetic acid was added. After 4 hours, the solvents were removed in vacuo, the residue dissolved in methylene chloride, which was then extracted with sat'd $NaHCO_3$. After separation, the aqueous layer was acidified, reextracted with methylene chloride which was then dried and concentrated to afford 470 mg (60%) of 2(R)-methyl-4-benzylsuccinic acid. Part D. To a solution of 470 mg (2.11 mmol) of product from part C and 463 mg (3.03 mg) of HOBT in 5 mL of DMF at 0° C. was added 451 mg (2.35 mmol) of EDC. After 30 min. at 0° C, a solution of 728 mg (2.08 mmol) of 1 in 3 mL of DMF was added. After stirring at 0° C. for 1 hour and 15 hours at RT, ethyl acetate was added and extracted with sat'd $NaHCO_3$, 5% aqueous citric acid, brine, dried and concentrated to give 930 mg of crude product chromatography on silica gel using 0–10% ethyl acetate/hexane one obtains 570 mg (50%) of butanoic acid, 4-[[3-[[[(1,1-dimethylethyl)amino]carbonyl] (3-methylbutyl)amino]-2-hydroxy-1-(phenylmethyl)propyl] amino]-2-methyl-4-oxo-, [1S-[1R*(2S*), 2S*]-, benzyl ester.

Part E. The product was hydrogenated in methanol using 10% palladium on carbon under 40 psig of hydrogen to afford butanoic acid, 4-[[3-[[[(1,1-dimethylethyl)amino] carbonyl]-(3-methylbutyl)amino]-2-hydroxy-1-(phenylmethyl)propyl]amino]-2-methyl-4-oxo-, [1 S-[1R* (2S*), 2S*]-.

Part F. To a solution of 427 mg (0.92 mmol) of product from part E and 210 mg (1.37 mmol) in 3 mL of DMF at 0° C. was added 196 mg (1.02 mmol) of EDC. After 30 min. at 0° C., 2 mL of conc. aqueous ammonia was added. After 1 hour at 0° C. and 15 hours at RT, ethyl acetate was added and then extracted with sat'd NaHCO₃, brine, dried and concentrated to afford crude product. Recrystallization from ethyl acetate/hexane afforded 50 mg (12%) of butanediamide, N-[3-[[[(1,1-dimethylethyl)amino]carbonyl](3-methylbutyl)amino]-2-hydroxy-1-(phenylmethyl)propyl]-3-methyl-, [1 S-[1R*(3S*), 2S*]]-.

EXAMPLE 41

Preparation of butanediamide, N-3-[[[1,1-dimethylethylamino]carbonyl](3-methylbutyl)amino]-2-hydroxy-1-(phenylmethyl)propyl]-3-methyl-, [1S-[1R*(3R*), 2S*]]-.

This was prepared in an identical manner to the previous example except that the asymmetric hydrogenation step was done in the presence of [((S,S-dipamp)cyclooctadienyl)rhodium]-tetrafluoroborate as catalyst.

EXAMPLE 42

Preparation of butanediamide, N-[3-[[[(1,1-dimethylethyl)amino]carbonyl](3-methylbutyl)amino]-2-hydroxy-1-phenylmethyl)propyl]-, 1S-[1R* (2S*, 3R*), 2S*]], and 1S-[1R*(2R*, 3S*), 2S*]].

Part A. To a solution of 863 mg (5.91 mmol) of meso-2,3-dimethylsuccinic acid in 7 mL of DMF at RT was added 1.13 g (5.91 mmol) of EDC. After 15 minutes, a solution of 2.07 g (5.91 mmol) of 1 and 1.4 mL of pyridine in 7 mL of anhydrous methylene chloride was added. After 11 hours, ethyl acetate was added and washed with 0.2N HCl, brine, dried and concentrated to afford 2.73 g (97%) of a 1:1 mixture of diastereomeric acids.

Part B. To a solution of 1.45 g (3.04 mmol) of the 1:1 mixture from part A and 613 mg (4.51 mmol) of HOBT in 10 mL of DMF at 0° C. was added 635 mg (3.31 mmol) of EDC. After 30 minutes at 0° C., 5 mL of conc. aqueous ammonia was added. After 1 hour at 0° C. and 14 hours at RT, ethyl acetate was added, washed with 0.2N HCl, sat'd NaHCO₃, brine, dried and concentrated to afford 0.64 g (44%) of a 1:1 mixture of amides.

These were separated on a Whatman 10 micron partisil column using 8%-14% isopropanol/-methylene chloride. The first isomer to elute was identified as butanediamide, N-[3-[[[(1,1 -dimethylethyl)amino]carbonyl](3-methylbutyl)amino]-2-hydroxy-1-(phenylmethyl)propyl]-, [1S-[1R*(2R*, 3S*), 2S*], m/e/=477 (M+H).

The second isomer to elute was identified as butanediamide, N-[3-[[[(1,1-dimethylethyl)amino]-carbonyl](3-methylbutyl)amino]-2-hydroxy-1 -(phenylmethyl)propyl]-, [1S-[1R*(2S*, 3R*), 2S*], m/e= 477 (M+H).

Preparation of pentanediamide, N-[3-[[[(1,1-dimethylethyl)amino]carbonyl](3-methylbutyl)amino-2-hydroxy-1-(phenylmethyl)propyl-3,3-dimethyl]-, [1S-[1R*, 2S*].

Part A. To a solution of 232 mg (0.66 mmol) of the product from Example 34, Part E, and 98 mg (1.2 mmol) of pyridine in 2 mL of methylene chloride was added 95 mg (0.66 mmol) of 3,3-dimethylglutaric anhydride at RT. After 15 hours, ethyl acetate was added, washed with 1N HCl, brine, dried and concentrated to afford 261 mg of crude product. Chromatography on silica gel using 5–20% methanol/methylene chloride afforded 108 mg of acid, m/e=492 (M+H).

Part B. To a solution of 92 mg (0.19 mmol) of product from part A and 38 mg (0.28 mmol) HOBT in 0.5 mL DMF at 0° C. was added 36 mg (0.19 mmol) of EDC. After 30 minutes at 0° C., 0.25 mL of conc. aqueous ammonia was added. After 1 hour at 0° C. and 16 hours at RT, ethyl acetate was added, washed with 0.2N HCl, sat'd NaHCO₃, brine, dried and concentrated to afford 72 mg of crude product. This was passed through a one-inch column of basic alumina with 10% methanol/methylene chloride to afford 53 mg of desired product, m/e=491 (M+H).

EXAMPLE 44

Preparation of butanediamide, N-[3-[[[(1,1-dimethylethyl)amino]carbonyl](3-methylbutyl)amino]-2-hydroxy-1-(phenylmethyl)propyl]-2,3-dimethyl-[1S-[1R*(2R*, 3S*), 2S*]](Isomer #1)

and

Preparation of butanediamide, N-[3-[[[1,1-dimethylethyl)amino]carbonyl](3-methylbutyl)amino]-2-hydroxy-1-(phenylmethyl)propyl]-2,3-dimethyl-[1S-[1R*(2R*, 3S*), 2S*]](Isomer #2).

Part A. To a solution of 1.47 g (4.20 mmol) of the product from Example 34, Part E, and 1.4 mL of pyridine in 9 mL of methylene chloride at RT was added 538 mg (4.20 mmol) of 2,2-dimethylsuccinic anhydride. After 15 hours, ethyl acetate was added and washed with 0.2N HCl, brine, dried and concentrated to afford 1.87 g of crude product (approx. 3:1 mixture of isomer).

Part B. To a solution of 1.85 g (3.9 mmol) of crude product from part A and 887 mg (5.8 mmol) of HOBT in 10 mL of DMF at 0° C. was added 809 mg (4.2 mmol) EDC. After 30 minutes at 0° C., 6 mL of conc. aqueous ammonia was added. After 1 hour at 0° C. and 15 hours at RT, ethyl acetate was added, washed with 0.2N HCl, sat'd NaHCO₃, brine, dried and concentrated to afford 923 mg of crude product. The two isomers were separated on a Whatman Partisil 5 column using 8–14% isopropanol/methylene chloride. The major isomer was identified as Isomer #1, m/e=477 (M+H).

The minor isomer was identified as Isomer #2, m/e=477 (M+H).

EXAMPLE 45

This example illustrates the procedure utilized to prepare compounds wherein the stereochemistry about the hydroxyl group is (S).

Part A. A solution of 3(S)-(1,1-dimethylethoxycarbonyl)amino-1,2-(R)-epoxy-4-phenylbutane (1.00 g, 3.80 mmol) and isobutylamine (5.55 g, 76 mmol, 20 equiv.) in 10 mL of isopropyl alcohol was warmed to 60° C. for 1 hour. The solution was cooled to room temperature and concentrated in vacuo and the residue recrystallized from hexane/methylene chloride to give 0.93 g, 73% of [2(S), 3(S)]-N-[[[3-[(1,1-dimethylethyl)carbamoyl]amino]]-2-hydroxy-4-phenylbutyl]N-[(3-methylbutyl)]amine, mp 91.3°–93.0° C.

Part B. The product from Part A (46.3 mg, 0.14 mmol) was dissolved in a mixture of 5 mL of tetrahydrofuran and 2 mL of methylene chloride and treated with tert-butylisocyanate (136.4 mg, 1.376 mmol) via syringe. The solution was stirred at room temperature for 0.5 hour and then the solvent was removed in vacuo. The product, TLC on SiO₂, 1:1 hexane: Ethyl acetate had Rf=0.74 and was used directly in the next step without further purification.

Part C. The crude product from Part B was taken up in 10 mL of 4N hydrochloric acid in dioxane and stirred at room temperature for 0.25 hours. The solvent and excess hydrochloric acid was removed in vacuo whereupon the product crystallized. The solid was isolated by filtration washed with acetone and dried in vacuo to 3-[[(1,1 -dimethylethyl) amino]carbonyl](2-methylpropyl)amino-2(S)-hydroxy-1(S) -(phenylmethyl)propylamine hydrochloride.

Part D. A solution of N-Cbz-L-asparagine (225.5 mg, 0.847 mmol) and N-hydroxybenzotriazole (182.9 mg, 1.21 mmol) was dissolved in 2 mL of dimethylformamide and cooled to 0° C. and then treated with EDC (170.2 mg, 0.898 mmol) for 10 minutes. This mixture was then treated with 3-[[(1,1-dimethylethyl)amino]carbonyl](2-methylpropyl)amino-2(S) -hydroxy-1 (S)-(phenylmethyl)propylamine hydrochloride. (300.0 mg, 0.807 mmol) followed by N-methylmorpholine (90.0 mg, 0.888 mmol) via syringe. The solution was stirred at room temperature for 16 hours and then poured into 20 mL of rapidly stirring 60% saturated aqueous sodium bicarbonate solution whereupon a white precipitate formed. The solid was isolated by filtration, washed with saturated aqueous sodium bicarbonate solution, water, 5% aqueous citric acid solution, water and then dried in vacuo to give 319 mg, 68% of butanediamide, N1-[3-[[[( 1,1 -dimethylethyl) amino]carboyl](2-methylpropyl)amino]-2(S)-hydroxy-1 (S)-(phenylmethyl)propyl]-2(S)-[(benzyloxycarbonyl) amino]mp 139°–141° C., MH+m/z=584.

EXAMPLE 46

Exemplary compounds of the present invention were prepared by the following methods.

METHOD A—Urea formation from 3(S)-benzyloxycarbonylamino-(R)hydroxy 4-phenyl butyl amine and an amino acid or peptide utilizing carbodiimidazole.

Part A. A Fisher-Porter bottle was charged with 3(S)-(benzyloxycarbonyl)amino-1,2(S)epoxy-phenylbutane (520 mg, 1.75 mmol) and 20 ml of isopropyl alcohol. Anhydrous ammonia was then bubbled into the solution at 0° C. until the solution was saturated. The bottle was capped and the solution warmed to 0° C. for 16 hours. The solvent was removed/n vacuo and a white solid was isolated, 460 mg, 84% 3(S)-benzyloxycarbonylamino-(R)-hydroxy-4-phenylbutyl amine, which was used directly in the next step.

Part B. L-leucine methyl ester hydrochloride (265.9 mg, 1.465 mmol) was dissolved in 20 ml of chloroform at 50° C. To this solution was added carbonyldiimidazole (237.6 mg, 1.465 mmol). The crude amino alcohol from Part A was dissolved in chloroform and added to the reaction mixture. The mixture was maintained at 50° C. for 16 hours. The reaction mixture was cooled to room temperature and poured into a separatory funnel and washed with 1N KHSO$_4$, saturated aqueous NaHCO$_3$ saturated aqueous NaCl, the chloroform layer was dried over anhydrous magnesium sulfate, filtered and concentrated in vacuo to give a white solid. The solid was recrystallized from ethyl acetate to give 503 mg, 71% of pure [[[3(S)-3[[1,1-dimethylethoxycarbonyl]]amino 2(S)-hydroxy-4-phenylbutyl][amino carbonyl]]]-L-leucine methyl ester. TLC SiO$_2$ 1:1 hexane: EtOAc Rf=0.52, mp 156.5°–157.5° C.

METHOD B—Preparation Utilizing Peptide Coupling.

Part A. L-Leucine methyl ester hydrochloride (527 mg, 2.9 mmol), carbonyldiimidazole (470 mg, 29 mmol) and 50 ml of chloroform were warmed to 50° C. for 1.5 hours and then treated with 3(S)-1,1-dimethylethoxycarbonylamino- 2(S)-hydroxy 4-phenylbutyl methyl amine (852 mg, 2.9 mmol) followed by triethylamine (404 mg, 4.0 mmol). The mixture was maintained at 50° C. for an additional 2 hours and then the reaction mixture was poured into a separatory funnel. The chloroform solution was washed with saturated aqueous NaHCO$_3$, twice with 1N aq. KHSO$_4$, once with water, and once with brine. The organic phase was dried over anhyd. MgSO$_4$, filtered and concentrated to give 1.38 g of an oil. The oil was chromatographed on SiO$_2$ eluting with hexanes/ ethyl acetate to give N-[[[3(S)-3[[1,1-dimethylethoxycarbonyl]]amino-2(S)-hydroxy-4-phenylbutyl][methylaminocarbonyl]]]-L-leucine methyl ester as a glassy foam, 870 mg, 65%, TLC on SiO$_2$ eluting with 1:1 hexane: ethyl acetate showed Rf=0.35.

Part B. The purified product from Part A (580 mg, 1.24 mmol) was treated with a solution of lithium hydroxide (65 mg, 1.5 mmol, 1.2 eq) in water (12 ml) and methanol (15 ml). The reaction was stirred at room temperature for 13 hours. The solution was concentrated in vacuo and diluted with water, acidified to pH=1 with 1N KHSO$_4$, filtered and concentrated in vacuo to give 560 mg of N-[[[3(S)-3[[1,1-dimethylethoxycarbonyl]]amino-2(S)-hydroxy-4-phenylbutyl][methylamino carbonyl]]]-L-leucine as a glassy foam, mp 145°–146° C. 100%.

Part C. The product from Part B (219 mg, 0.486 mmol), 1-hydroxybenzotriazole (74.3 mg, 0.486 mmol), 1-(3-dimethylaminopropyl)-3-ethylcarbodiimide hydrochloride (93.1 mg, 0.486 mmol), and L-phenylalanine methyl ester hydrochloride (105 mg, 0.486 mmol) were dissolved in 10 ml of chloroform. The solution was cooled to 0° C. and treated with N-methyl morpholine (54 mg, 0.534 mmol) via syringe. The reaction was maintained at 0° C. for 1 hour and at room temperature for an additional hour. The reaction was poured into a separatory funnel and diluted with chloroform and washed twice with 1N aqueous KHSO$_4$, once with H$_2$O, twice with saturated aqueous NaHCO$_3$, once with brine dried over anhydrous MgSO$_4$, filtered and concentrated in vacuo to give a white solid. The solid was recrystallized from ethyl acetate/hexane to give 160 mg, 54% of pure N[[[3(S)-3[[1,1-dimethylethoxycarbonyl]]amino-2(S)-hydroxy-4-phenylbutyl][methylaminocarbonyl]]]-L-leucyI-L-phenylalanine methyl ester, mp 150°–151° C. TLC SiO$_2$:1 ethyl acetate:hexane Rf=0.50.

Part D. A sample of the product from Part C (48.6 mg, 0.79 mmol) was dissolved in anhydrous methanol and treated in with anhydrous ammonia at 0° C. until the solution was saturated. The reaction was allowed to stand undisturbed for 96 hours and then concentrated in vacuo. The crude solid was taken up in ether with a small amount of isopropyl alcohol and allowed to stand undisturbed whereupon crystals of pure N-[[3(S)-3[[1,1-dimethylethoxycarbonyl]] amino-2(S)-hydroxy-4-phenyl-butyl] [methylaminocarbonyl][-L-leucyI-L-phenylalanyl]]]amide 21.4 mg, 45%, mp 120°–122° C. TLC SiO$_2$ 100% ethyl acetate Rf=0.33.

METHOD C—Synthesis Via Dipeptide Coupling

Part A. L-Leucyl-L-phenylalanine methyl ester hydrochloride.

A solution of Boc-L-LeucyI-L-phenylalanine methyl ester (2.01 g, 5.13 mmol) in 10 ml of 4N HCl in dioxane was stirred at room temperature for 45m whereupon the entire solution solidified. The solid was crushed and slurried with anhydrous ether and isolated by filtration on a Buchner funnel. The solid was dried in vacuo to give 1.65 g, 97%, of L-leucyl-L-phenylalanine methyl ester hydrochloride suitable for subsequent reaction.

Part B. A solution of 3(S)-1,1-dimethylethoxycarbonyl, amino 1,2(S)-epoxy 4-phenyl butane (1.30 g, 4.94 mmol) in 40 ml of isopropyl alcohol was treated with benzyl amine (529 mg, 4.94 mmol) at 50° C. for 16 hours. The solution was concentrated in vacuo to give an oil that was triturated with n-hexane to give N-[[3(S)-311,1-dimethylethoxycarbonyl]amino-2(S)-hydroxy-4-phenylbutyl]]N-benzylamine, a white solid, 1.36 g, 74% mp 87.5°–89.5° C.

Part C. A solution of L-leucyl L-phenylalanine methyl ester hydrochloride (172.1 mg, 0.524 mmol), in 5 ml of chloroform was treated with carbonyldiimidazole (89.2 mg, 0.55 mmol, 1.05 equiv.). The solution was cooled with an ice bath and treated with N-methyl morpholine (53 mg, 0.524 mmol) and then with imidazole (35.6 mg, 0.524 mmol). The solution was maintained at 0° C. for 0.5 hour and then treated with the amino alcohol from Part B (193.8 mg, 0.524 mmol). The solution was allowed to warm to room temperature and maintained at that temperature for 3 hours. The reaction mixture was poured into a separatory funnel, diluted with additional chloroform and washed twice with 1N KHSO$_4$, twice with saturated aqueous NaHCO$_3$, once with brine, dried over anhydrous magnesium sulfate, filtered and concentrated in vacuo. The crude product was purified by radial chromatography on SiO$_2$ eluting with hexanes/ethyl acetate to give pure N-[[[3(S)-3-[[1,1-dimethylethoxycarbonyl]]amino-2(S)-hydroxy-4-phenylbutyl][benzylamino carbonyl]]]-L-leucyl-L-phenylalanine]]] methyl ester as a white solid 226.8 mg, 63%, mp 9.5°–70.5° C. TLC on SiO$_2$ 1:1 hexanes: EtQAc Rf=0.60.

Part D. A sample of the purified material from Part C (59.1 mg, 0.85 mmol) in 3 ml of methanol was cooled to 0° C. and treated with anhydrous ammonia until the solution was saturated. The mixture was set aside at room temperature for 24 hours and then concentrated in vacuo to give a white solid. This material was recrystallized from hexanes/ethyl acetate to give pure N-[[[3(S)-3-[[1,1-dimethylethoxycarbonyl]]amino-2(S)-hydroxy-4-phenylbutyl][benzylamino carbonyl]]]-L-leucyl-L-phenylalanyl amide 39.9 mg 69%, mp 137°–138° C.

METHOD D—Synthesis via Curtius Rearrangement.

Part A. A solution consisting of 4(S)I,1-dimethylethoxycarbonylamino-3(S)-hydroxy-5-phenyl pentanoic acid (800 mg, 2.59 mmol), imidazole (847 mg, 12.43 mmol), tert-butyldimethylsilyl chloride (937 mg, 6.22 mmol) in 10 ml of dry dimethylformamide was stirred at room temperature for 24 hours. The solvent was removed in vacuo and the residue dissolved in ethyl acetate; the solution was washed with water, 5% aqueous citric acid, water and brine. The ethyl acetate solution was dried over anhydrous MgSO$_4$, filtered and concentrated in vacuo to give a thick oil that was dissolved in 40 ml of methanol. The methanolic solution was then treated with 7 ml of 10% aqueous K$_2$CO$_3$. After stirring for an hour the solution was concentrated in vacuo and the residue dissolved in water. The aqueous phase was acidified to pH=1 with 1N KHSO$_4$ and then extracted three times with ether. The combined ethereal solution was washed with brine, dried over anhydrous MgSO$_4$, filtered and concentrated in vacuo to give 1.00 g, 98% of 4(S)-1,1-dimethylethoxycarbonylamino-3(S)tert-butyldimethylsilyloxy-5-phenylpentanoic acid, as a white solid. The solid was recrystallized from n-hexane to provide 803 mg, 79% of pure acid, mp 148°–149° C.

Part B. A solution of the product from Part A (300 mg, 0.76 mmol) and triethylamine (153 mg, 1.52 mmol, 2.0 eq) was dissolved in 30 ml of toluene and warmed to 90° C. To this stirring solution was added diphenylphosphorylazide (219 mg, 0.80 mmol, 1.05 eq) via syringe. After 1.5 hours at 90° C. the solution was treated with L-leucyl-L-phenylalanine methyl ester hydrochloride (251 mg, 0.80 mmol). The solution was allowed to stir at 45° C. for 16 hours and then the solution was cooled to room temperature and poured into a separatory funnel. The solution was washed with water, twice with 1N KHSO$_4$, water, sat. aq. NaHCO$_3$, & brine. The solution was then dried over anhydrous MgSO$_4$, filtered and the material was purified by radial chromatography on SiO$_2$ eluting with hexanes/ethyl acetate to provide 270 mg, 50% of pure urea N-[[[3(S)-3-[[1,1-dimethylethoxycarbonyl]amino-2(S)-tert-butyldimethylsilyloxy,-4-phenylbutyl][amino carbonyl]]]-L-leucyl-L-phenylalanine methyl ester, mp 146°–147° C.

Part C. A solution of the product from Part B (250 mg, 0.35 mmol) in tetrahydrofuran (5 ml) was treated with a 1N solution of tetra-N-butylammonium fluoride (0.7 ml, 0.7 mmol, 2 eq). The solution was stirred for 1 hour at room temperature and then concentrated in vacuo. The residue was dissolved in ethyl acetate and washed four times with water, brine, dried over anhydrous MgSO$_4$, filtered and concentrated in vacuo to give N-[[[3(S)-3-[[1,1-dimethylethoxycarbonyl]]amino-2(S)-hydroxy-4-phenylbutyl][amino carbonyl]]]-L-leucyl-L-phenylalanine methyl ester as a white solid 200 mg, 96%, mp 180°–182° C., TLC on SiO$_2$ 100% EtAc Rf=0.64.

Part D. The product from Part C (20.2 mg, 0.34 mmol) was dissolved in 1 ml of methanol and cooled to 0° C. The solution was saturated with anhyd. ammonia and then kept at room temperature for 48 hours. The solvent was removed in vacuo and was a white solid obtained and was recrystallized from methanol to give 19.5 mg, 97% of pure N-[[[3(S)-3[[1,1-dimethylethoxycarbonyl]]amino-2(S)-hydroxy-4-phenylbutyl][amino carbonyl]]]-L-leucyl-L-phenylalanyl amide mp 187°–188° C. (dec). TLC on SiO$_2$ 100% EtOAc Rf=0.29.

EXAMPLE 47

Following the procedures set forth in Example 46, the compounds set forth in Tables 17 and 18 were prepared.

TABLE 17

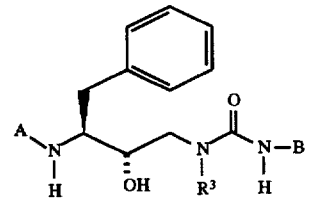

| Entry | NH—B | R$^3$ | A |
|---|---|---|---|
| 1.* | L-Leu—OMe | CH$_2$C$_6$H$_5$ | Cbz-L-Asn |
| 2. | L-Leu—OMe | CH$_2$C$_6$H$_5$ | Cbz-L-Asn |
| 3. | Leu—PheOCH$_3$ | H | Boc |
| 4. | Leu—Phe—NH$_2$ | H | Boc |
| 5. | Leu Phe—NH$_2$ | CH$_3$ | Boc |
| 6. | Leu Phe—NH$_2$ | CH$_2$C$_6$H$_5$ | Boc |
| 7. | LeuNHCH$_2$C$_6$H$_5$ | H | Boc |
| 8. | CH$_2$C$_6$H$_5$ | 2-Nap | Boc |
| 9. | 2-Nap | 2-Nap | Boc |
| 10. | Phe—LeuOMe | H | Boc |

TABLE 17-continued

[Structure: phenyl-CH2-CH(NHA where A is attached, H on N)-CH(OH)-CH2-N(R3)-C(=O)-NH-B]

| Entry | NH—B | R³ | A |
|---|---|---|---|
| 11. | Phe—Leu—NH₂ | H | Boc |
| 12. | PheLeuPheNH₂ | H | Boc |

*(R) Stereochemistry at C-2

TABLE 18

[Structure: Boc-NH-CH(R²)-CH(OH)-CH2-NH-C(=O)-NH-B]

| Entry | NH—B | R² |
|---|---|---|
| 1. | LeuPhe—OMe | CH₂SCH₃ |
| 2. | LeuPhe—NH₂ | CH₂SCH₃ |
| 3. | LeuPhe—NH₂ | CH₂CH₂CH₃ |
| 4. | LeuPhe—OMe | CH₂CH₂CH₃ |
| 5. | GlnArg—NH₂ | CH₂CH₂CH₃ |
| 6. | LeuPhe—NH₂ | 2-Naphthyl |

EXAMPLE 48

Following the procedures set forth above in Example 46, the compounds set forth in Tables 19 and 20 were prepared.

TABLE 19

[Structure with isobutyl group and t-Bu]

| Entry | R² | A |
|---|---|---|
| 1. | n-Bu | Boc |
| 2. | n-Bu | Cbz |
| 3. | C₆H₅CH₂ | Boc |
| 4. | C₆H₅CH₂ | Cbz |
| 5. | C₆H₅CH₂ | benzoyl |
| 6. | cyclohexylmethyl | Cbz |
| 7. | 2-naphthylmethyl | Cbz |

TABLE 20

[Structure: Cbz-NH-CH(CH2Ph)-CH(OH)-CH2-N(isobutyl)-C(=S)-N(H)R⁴]

| Entry | XHR⁴ |
|---|---|
| 1. | NHEt |
| 2. | NHᵗBu |

EXAMPLE 49

The compounds of Table 21 were prepared according to the generalized procedures set forth above in Example 46.

TABLE 21

[Structure: R-C(=O)-NH-CH(CH2Ph)-CH(OH)-CH2-N(isobutyl)-C(=S)-NH-tBu]

| Entry | R |
|---|---|
| 1. | C₆H₅CH₂O— |
| 2. | (CH₃)₃C— |
| 3. | (CH₃)₂CH— |
| 4. | C₆H₅ |
| 5. | 2-quinoyl |
| 6. | (CH₃)₃C—NH— |
| 7. | CH₃CH₂CH₂CH₂NH— |
| 8. | (CH₃)₃CO— |
| 9. | C₆H₅CH₂CH₂— |
| 10. | (E)C₆H₅CHCH— |
| 11. | (CH₃)₂CHCH₂O |
| 12. | C₆H₅OCH₂— |
| 13. | CH₃CH₂CH₂— |
| 14. | 2-naphthyl- |
| 15. | C₆H₅CH₂NH— |
| 16. | (CH₃)₂CHCH₂— |
| 17. | (CH₃)₃CCH₂— |
| 18. | C₆H₅CH₂O— |
| 19. | CH₃OC₆H₅CH₂O— |
| 20. | C₆H₅CH(CH₃)O— |
| 21. | (CH₃)₂CH—O— |
| 22. | (CH₃)₂CH—O— |
| 23. | (CH₃)₂CHCH₂O— |
| 24. | Cyclopropyl-CH₂O— |
| 25. | Cyclobutyl-CH₂O— |
| 26. | C₆H₅O— |
| 27. | CH₃CH₂CH₂O— |
| 28. | CH₂CHCH₂O— |
| 29. | CH₃CH₂O— |
| 30. | CH₃CH₂CH₂—O— |
| 31. | (CH₃)₃CCH₂—O— |
| 32. | C₆H₅—O— |
| 33. | 2-naphthyl-O— |
| 34. | (CH₃)₂CH—O— |

TABLE 21-continued

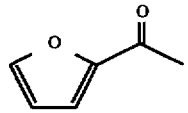

| Entry | R |
|---|---|
| 35. | Cyclohexyl-O— |
| 36. | 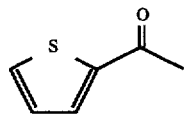 |
| 37. | 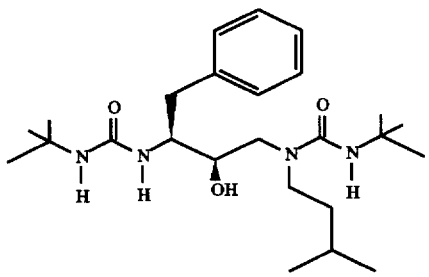 |

EXAMPLE 50

A bis-t-butyl urea compound of the formula:

was prepared according to the following procedure.

Part A. A solution of 3(S)-(benzyloxycarbonyl)-1,2-(S) epoxy-4-phenylbutane (12.02 g, 40.4 mmol) was treated with excess isoamylamine as described previously to give 12.06 g, 78% of N[3(S)obenzyloxycarbonyl-amino-2(R)-hydroxy-4-phenylbutyl]N-isoamyl amine, mp 130°–132° C., MH+m/z=385. Part B. The product from Part A (470.6 mg, 1.22 mmol) was treated with one equivalent of tert-butyl isocyanate as described previously to give 550 mg, 93% of (2R,3S)-3(N-benzyloxycarbonyl)amido-1-isoamyl-1-(tert-butylcarbamoyl)amino-4-phenyl-2-butanol as a foam, MH+, m/z =484.

Part C. The product from Part B (500 mg, 1.03 mmol) was hydrogenated in the presence of 10% palladium-on-carbon catalyst to give 356 mg, 99%, of (2R, 3S)-3-amino-1-isoamyl-1-(tert-butyl-carbamoyl)amino-4-phenyl-2-butanol as an oil.

Part D. The product from Part C (197.1 mg, 0.564 mmol) in 2 mL of tetrahydrofuran was treated with tert-butylisocyanate (55.9 mg, 0.564 mmol) via syringe. The mixture was allowed to stand at room temperature for 3 hours and then concentrated in vacuo to give a white foam 240 mg, 95%, of (2R, 3S)-3(N-tert-butylcarbamoyl)amino-1-isoamyl-1 (tert-butylcarbamoyl)amino-4-phenyl-2-butanol, mp 79°–81° C., MH+m/z=449.

EXAMPLE 51

The compounds of the present invention are effective HIV protease inhibitors. Utilizing an enzyme assay as described below, the compounds set forth in the examples herein disclosed inhibited the HIV enzyme. The preferred compounds of the present invention and their calculated $IC_{50}$ (inhibiting concentration 50%, i.e., the concentration at which the inhibitor compound reduces enzyme activity by 50%) values are shown in Table 22. The enzyme method is described below. The substrate is 2-aminobenzoyl-Ile-Nle-Phe(p-$NO_2$)-Gln-Arg$NH_2$. The positive control is MVT-101 (Miller, M. et al, Science, 246, 1149 (1989)] The assay conditions are as follows:

Assay buffer:

20 mM sodium phosphate, pH 6.4

20% glycerol 1 mM EDTA 1 mM DTT 0.1% CHAPS

The above described substrate is dissolved in DMSO, then diluted 10 fold in assay buffer. Final substrate concentration in the assay is 80 μM.

HIV protease is diluted in the assay buffer to a final enzyme concentration of 12.3 nanomolar, based on a molecular weight of 10,780.

The final concentration of DMSO is 14% and the final concentration of glycerol is 18%. The test compound is dissolved in DMSO and diluted in DMSO to 10× the test concentration; 10 μl of the enzyme preparation is added, the materials mixed and then the mixture is incubated at ambient temperature for 15 minutes. The enzyme reaction is initiated by the addition of 40 μl of substrate. The increase in fluorescence is monitored at 4 time points (0, 8, 16 and 24 minutes) at ambient temperature. Each assay is carried out in duplicate wells.

TABLE 22

| Compound | $IC_{50}$ |
|---|---|
| (2S,3S)-3-(N-1,1-dimethylethoxy-carbonyl)amido-1-(L-phenylalanyl-L-leucylcarbamoyl)amino-4-phenyl butanol | 5 μM |
| (2R,3S)-3-(N-2-quinoylcarbonyl-L-asparaginyl)amido-1-iso-butyl-1-(t-butylcarbamoyl)amino-4-phenyl-2-butanol | 7 nM |
| Carbamic acid, [3-[[[(1,1-dimethyl-ethyl)amino]carbonyl](3-methylbutyl)-amino]-2-hydroxy-1-(phenylmethyl)-propyl]-, (4-methoxyphenyl)methyl ester, [1S-[1R*,2S*]] | 489 nM |
| Carbamic acid, [3-[[[(1,1-dimethyl-ethyl)amino]carbonyl](3-methylbutyl)-amino]-2-hydroxy-1-(phenylmethyl)-propyl]-, phenylmethyl ester, [1S-[1R*,2S*]] | 112 nM |
| Carbamic acid, [3-[[[(1,1-dimethyl-ethyl)amino]carbonyl](3-methylbutyl) amino]-2-hydroxy-1-(phenylmethyl) propyl]-, prop-2-enyl ester, [1S-[1R*,2S*]] | 170 nM |
| Butaneamide, N-[3-[[[(1,1-dimethyl-ethyl)amino]carbonyl](3-methylbutyl) amino]-2-hydroxy-1-(phenylmethyl)-propyl]-3,3-dimethyl-, [1S-[1R*,2S*]] | 3.7 nM |

TABLE 22-continued

| Compound | IC$_{50}$ |
| --- | --- |
| Phenylmethylamide, N-[3-[[[(1,1-dimethylethyl)amino]carbonyl](3-methylbutyl)amino]-2-hydroxy-1-(phenylmethyl)propyl]-3,3-dimethyl-, [1S-[1R*,2S*]] | 850 nM |

EXAMPLE 52

The effectiveness of the compounds listed in Table 23 were determined in the above-described enzyme assay and in a CEM cell assay.

The HIV inhibition assay method of acutely infected cells is an automated tetrazolium based colorimetric assay essentially that reported by Pauwles et al, *J. Virol. Methods* 20, 309–321 (1988). Assays were performed in 96-well tissue culture plates. CEM cells, a CD4+cell line, were grown in RPMI-1640 medium (Gibco) supplemented with a 10% fetal calf serum and were then treated with polybrene (2 µg/ml). An 80 µl volume of medium containing 1×10$^4$ cells was dispensed into each well of the tissue culture plate. To each well was added a 100µl volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of 5×10$^4$ TCID$_{50}$ per ml (TCID$_{50}$=the dose of virus that infects 50% of cells in tissue culture), and a 20 µL volume of the virus sample (containing 1000 TCID$_{50}$ of virus) was added to wells containing test compound and to wells containing only medium (infected control cells). Several wells received culture medium without virus (uninfected control cells). Likewise, the intrinsic toxicity of the test compound was determined by adding medium without virus to several wells containing test compound. In summary, the tissue culture plates contained the following experiments:

|   | Cells | Drug | Virus |
| --- | --- | --- | --- |
| 1. | + | − | − |
| 2. | + | + | − |
| 3. | + | − | + |
| 4. | + | + | + |

In experiments 2 and 4 the final concentrations of test compounds were 1, 10, 100 and 500 µg/ml. Either azidothymidine (AZT) or dideoxyinosine (ddI) was included as a positive drug control. Test compounds were dissolved in DMSO and diluted into tissue culture medium so that the final DMSO concentration did not exceed 1.5% in any case. DMSO was added to all control wells at an appropriate concentration.

Following the addition of virus, cells were incubated at 37° C. in a humidified, 5% CO$_2$ atmosphere for 7 days. Test compounds could be added on days 0, 2 and 5 if desired. On day 7, post-infection, the cells in each well were resuspended and a 100 µl sample of each cell suspension was removed for assay. A 20 µL volume of a 5 mg/ml solution of 3-(4,5-dimethylthiazol-2-yl)-2,5-diphenyltetrazolium bromide (MTT) was added to each 100 µL cell suspension, and the cells were incubated for 4 hours at 27° C. in a 5% CO$_2$ environment. During this incubation, MTT is metabolically reduced by living cells resulting in the production in the cell of a colored formazan product. To each sample was added 100 µl of 10% sodium dodecylsulfate in 0.01N HCl to lyse the cells, and samples were incubated overnight. The absorbance at 590 nm was determined for each sample using a Molecular Devices microplate reader. Absorbance values for each set of wells is compared to assess viral control infection, uninfected control cell response as well as test compound by cytotoxicity and antiviral efficacy.

TABLE 23

| Compound | IC$_{50}$ | EC$_{50}$ | TD$_{50}$ |
| --- | --- | --- | --- |
| (2S,3S)-3-(N-1,1-dimethylethoxy-carbonyl)amido-1-(L-phenylalanyl-L-leucylcarbamoyl)amino-4-phenyl butanol | 5 µM | 13 µM | 54 µM |
| (2R,3S)-3-(N-2-quinoylcarbonyl-L-asparaginyl)amido-1-iso-butyl-1-(t-butylcarbamoyl)amino-4-phenyl-2-butanol | 7 nM | 10 nM | 16 µM |
| Carbamic acid, [3-[[[(1,1-dimethylethyl)amino]carbonyl](3-methylbutyl)amino]-2-hydroxy-1-(phenylmethyl)propyl]-, (4-methoxyphenyl)methyl ester, [1S-[1R*,2S*]] | 489 nM | 820 nM | |
| Carbamic acid, [3-[[[(1,1-dimethylethyl)amino]carbonyl](3-methylbutyl)amino]-2-hydroxy-1-(phenylmethyl)propyl]-, phenylmethyl ester, [1S-[1R*,2S*]] | 112 nM | | |
| Carbamic acid, [3-[[[(1,1-dimethylethyl)amino]carbonyl](3-methylbutyl)amino]-2-hydroxy-1-(phenylmethyl)propyl]-, prop-2-enyl ester, [1S-[1R*,2S*]] | 170 nM | | |
| Butaneamide, N-[3-[[[(1,1-dimethylethyl)amino]carbonyl](3-methylbutyl)amino]-2-hydroxy-1-(phenylmethyl)propyl]-3,3-dimethyl-, [1S-[1R*,2S*]] | 3.7 nM | | |
| Phenylmethylamide, N-[3-[[[(1,1-dimethylethyl)amino]carbonyl](3-methylbutyl)amino]-2-hydroxy-1-(phenylmethyl)propyl]-3,3-dimethyl-, [1S-[1R*,2S*]] | 850 nM | 2 nM | |

Thus, utilizing the procedures set forth above, the compounds set forth in Tables 24–28 could be prepared.

TABLE 24

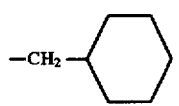

| Entry No. | R | R³ | R⁴ |
|---|---|---|---|
| 1. | Cbz[a] | CH₃ | n-Butyl |
| 2. | Cbz | i-Butyl | CH₃ |
| 3. | Cbz | i-Butyl | n-Butyl |
| 4. | Q[b] | i-Butyl | n-Butyl |
| 5. | Cbz | i-Propyl | n-Butyl |
| 6. | Q | i-Propyl | n-Butyl |
| 7. | Cbz | C₆H₅ | n-Butyl |
| 8. | Cbz | —CH₂-cyclohexyl | n-Butyl |
| 9. | Cbz | —CH₂-phenyl | n-Butyl |
| 10. | Q | —CH₂-phenyl | n-Butyl |
| 11. | Cbz | cyclohexyl | n-Butyl |
| 12. | Cbz | i-Butyl | n-Propyl |
| 13. | Cbz | i-Butyl | —CH₂CH(CH₃)₂ |
| 14 | Cbz | (R)—CH(CH₃)-phenyl | n-Butyl |
| 15. | Cbz | —CH₂-cyclohexyl | i-Propyl |
| 16. | Cbz | —CH₂-cyclohexyl | —CH₂CH₂CH(CH₃)₂ |
| 17. | Cbz | i-Butyl | —CH₂CH₃ |
| 18. | Cbz | i-Butyl | —CH(CH₃)₂ |
| 19. | Cbz | i-Butyl | cyclohexyl |
| 20. | Q | i-Butyl | cyclohexyl |
| 21. | Cbz | —CH₂-cyclohexyl | —(CH₂)₂CH(CH₃)₂ |

TABLE 24-continued

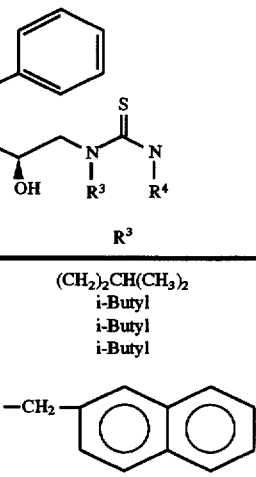

| Entry No. | R | R³ | R⁴ |
|---|---|---|---|
| 22. | Cbz | $-(CH_2)_2CH(CH_3)_2$ | $-CH(CH_3)_2$ |
| 23. | Q | i-Butyl | $-CH(CH_3)_2$ |
| 24. | Cbz | i-Butyl | $-(CH_3)_3$ |
| 25. | Q | i-Butyl | $-(CH_3)_3$ |
| 26. | Cbz | 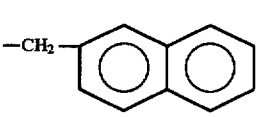 | $-(CH_3)_3$ |
| 27. | Q | 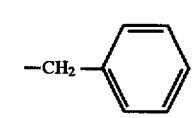 | $-(CH_3)_3$ |
| 28. | Cbz | $-(CH_2)_2CH(CH_3)_2$ | $-(CH_3)_3$ |
| 29. | Q | $-(CH_2)_2CH(CH_3)_2$ | $-(CH_3)_3$ |
| 30. | Cbz | $-CH_2C_6H_5$ | $-(CH_3)_3$ |
| 31. | Q | $-CH_2C_6H_5$ | $-(CH_3)_3$ |
| 32. | Cbz | $-(CH_2)_2C_6H_5$ | $-(CH_3)_3$ |
| 33. | Cbz | $-(CH_2)_2C_6H_5$ | $-(CH_3)_3$ |
| 34. | Cbz | n-Butyl | $-(CH_3)_3$ |
| 35. | Cbz | n-Pentyl | $-(CH_3)_3$ |
| 36. | Cbz | n-Hexyl | $-(CH_3)_3$ |
| 37. | Cbz | 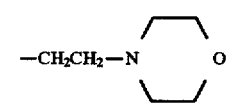 | $-(CH_3)_3$ |
| 38. | Cbz | $-CH_2C(CH_3)_3$ | $-(CH_3)_3$ |
| 39. | Q | $-CH_2C(CH_3)_3$ | $-(CH_3)_3$ |
| 40. | Cbz | 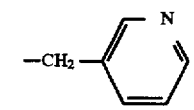 | $-(CH_3)_3$ |
| 41. | Cbz | $-CH_2C_6H_5OCH_3(para)$ | $-(CH_3)_3$ |
| 42. | Cbz | 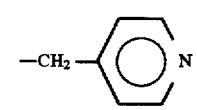 | $-(CH_3)_3$ |
| 43. | Cbz | 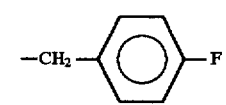 | $-(CH_3)_3$ |
| 44. | Cbz | $-(CH_2)_2C(CH_3)_3$ | $-(CH_3)_3$ |
| 45. | Q | $-(CH_2)_2C(CH_3)_3$ | $-(CH_3)_3$ |
| 46. | Cbz | $-(CH_2)_4OH$ | $-(CH_3)_3$ |
| 47. | Q | $-(CH_2)_4OH$ | $-(CH_3)_3$ |
| 48. | Q |  | $-(CH_3)_3$ |

TABLE 24-continued

| Entry No. | R | R³ | R⁴ |
|---|---|---|---|
| 49. | Q | —CH₂-(4-pyridyl) | —(CH₃)₃ |
| 50 | PhCH₂O-C(=O)-CH₂- | —(CH₂CH(CH₃)₂ | —(CH₃)₃ |
| 51. | 2-quinolinyl-C(=O)-CH₂- | —(CH₂CH(CH₃)₂ | —C(CH₃)₃ |
| 52. | (CH₃)₂N-CH₂-C(=O)-CH₂- | —(CH₂CH(CH₃)₂ | —C(CH₃)₃ |
| 53. | (pyrimidin-2-yl)-S-CH₂-C(=O)-CH₂- | —(CH₂CH(CH₃)₂ | —C(CH₃)₃ |
| 54. | (benzofuran-2-yl)-C(=O)-CH₂- | —(CH₂CH(CH₃)₂ | —C(CH₃)₃ |
| 55. | CH₃-C(=O)-CH₂- | —(CH₂CH(CH₃)₂ | —C(CH₃)₃ |
| 56. | (2-amidino-phenyl)-C(=O)-CH₂- | —(CH₂CH(CH₃)₂ | —C(CH₃)₃ |
| 57. | (pyridin-2-yl)-C(=O)-CH₂- | —(CH₂CH(CH₃)₂ | —C(CH₃)₃ |
| 58. | (3-hydroxyquinoxalin-2-yl)-C(=O)- | —(CH₂CH(CH₃)₂ | —C(CH₃)₃ |
| 59. | (3-hydroxypyridin-2-yl)-C(=O)- | —(CH₂CH(CH₃)₂ | —C(CH₃)₃ |

TABLE 24-continued
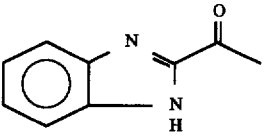
| Entry No. | R | R³ | R⁴ |
|---|---|---|---|
| 60. | 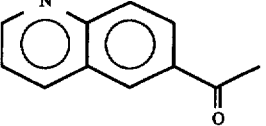 | —(CH₂CH(CH₃)₂ | —C(CH₃)₃ |
| 61. | 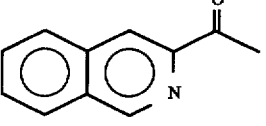 | —(CH₂CH(CH₃)₂ | —C(CH₃)₃ |
| 62. | 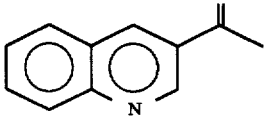 | —(CH₂CH(CH₃)₂ | —C(CH₃)₃ |
| 63. | 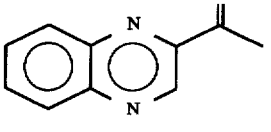 | —(CH₂CH(CH₃)₂ | —C(CH₃)₃ |
| 64. | 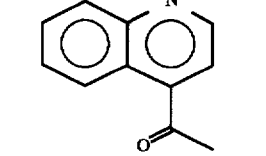 | —(CH₂CH(CH₃)₂ | —C(CH₃)₃ |
| 65. | 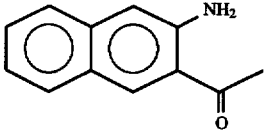 | —(CH₂CH(CH₃)₂ | —C(CH₃)₃ |
| 66. | 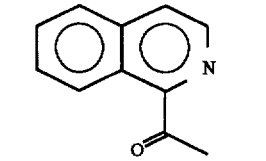 | —(CH₂CH(CH₃)₂ | —C(CH₃)₃ |
| 67. |  | —(CH₂CH(CH₃)₂ | —C(CH₃)₃ |

TABLE 24-continued

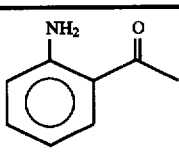

| Entry No. | R | R³ | R⁴ |
|---|---|---|---|
| 68. | (2-aminophenyl)carbonyl | —(CH₂CH(CH₃)₂ | —C(CH₃)₃ |
| 69. | (1-hydroxy-2-naphthyl)carbonyl | —(CH₂CH(CH₃)₂ | —C(CH₃)₃ |

TABLE 25

| Entry | R² | A |
|---|---|---|
| 1. | n-Bu | Cbz |
| 2. | cyclohexylmethyl | Cbz |
| 3. | i-butyl | Boc |
| 4. | n-Bu | Cbz |
| 5. | C₆H₅CH₂ | Boc |
| 6. | C₆H₅CH₂ | Cbz |
| 7. | C₆H₅CH₂ | benzoyl |
| 8. | cyclohexylmethyl | Cbz |
| 9. | n-Bu | Q |
| 10. | cyclohexylmethyl | Q |
| 11. | C₆H₅CH₂ | Cbz |
| 12. | C₆H₅CH₂ | Q |
| 13. | C₆H₅CH₂ | benzoyl |
| 14. | C₆H₅CH₂ | N,N-dimethylacetyl |
| 15. | C₆H₅CH₂ | aminocarbonyl |
| 16. | C₆H₅CH₂ | Boc |
| 17. | 2-naphthylmethyl | Boc |
| 18. | 2-naphthylmethyl | Q |
| 19. | 2-naphthylmethyl | Cbz |
| 20. | p-F(C₆H₄)CH₂ | Q |
| 21. | p-F(C₆H₄)CH₂ | Cbz |
| 22. | p-F(C₆H₄)CH₂ | Boc |

TABLE 26

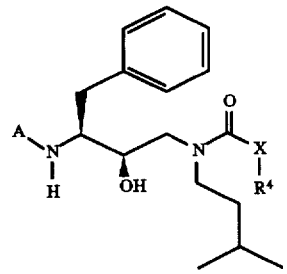

| Entry | XR⁴ | A |
|---|---|---|
| 1. | —NH$^t$Bu | Cbz |
| 2. | —NEt₂ | Cbz |
| 3. | —NHC(CH₃)₂CH₂CH₃ | Cbz |

TABLE 27

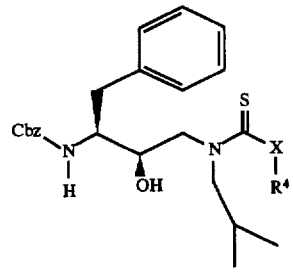

| Entry | XHR⁴ |
|---|---|
| 1. | NHEt |
| 2. | NH$^t$Bu |

TABLE 28

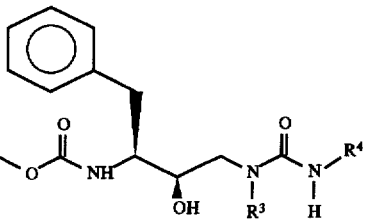

| R³ | R⁴ |
|---|---|
| —CH₂CH(CH₃)₂ | —C(CH₃)₃ |
| —CH₂CH₂CH(CH₃)₂ |  |
| —CH₂CH₂CH(CH₃)₂ |  |
| —CH₂CH₂CH(CH₃)₂ |  |
| —CH₂CH₂CH(CH₃)₂ |  |

The compounds of the present invention are effective antiviral compounds and, in particular, are effective inhibitors of retroviruses, particularly, lentroviruses as shown above. Thus, the subject compounds are effective inhibitors of HIV. It is contemplated that the subject compounds will also inhibit other strains of HIV, such as HIV-2 and other viruses such as, for example, human T-cell leukemia virus, feline leukemia virus, simiam immunodeficiency virus, respiratory syncitial virus, hepadnavirus, cytomegalovirus and picornavirus. Thus, the subject compounds are effective in the treatment and/or proplylaxis of retroviral infections.

Compounds of the present can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomericaly pure compound. The optically active compounds of Formula I can likewise be obtained by utilizing optically active starting materials.

These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more immunomodulators, antiviral agents or other antiinfective agents. For example, the compounds of the invention can be administered in combination with DDI, DDC, AZT or with N-butyl-1-deoynojirimycin or the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound represented by the formula:

wherein A represents radicals represented by formula:

wherein $R^2$ represents alkyl, aryl, cycloalkyl, cycloalkylalkyl and aralkyl radicals, which radicals are optionally substituted with a group selected from —$OR^9$, —$SR^9$, and halogen radicals, wherein $R^9$ represents hydrogen and alkyl radicals;

$R^3$ represents alkyl, alkenyl, alkynyl, hydoxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals where said substitutents are selected from alkyl, aryl, aralkyl, cycloalkyl, cycloalkylalkyl, heteroaryl, heteroalkyl, heterocycloalkyl, and heterocycloalkylalkyl radicals;

X' represents O, C($R^{17}$) where $R^{17}$ represents hydrogen and alkyl radicals, and N provided that when X' is O, $R^{12}$ is absent;

Y and Y' independents represent O,S and $NR^{15}$ wherein $R^{15}$ represents radicals as defined for $R^3$;

$R^4$, $R^5$, $R^{11}$ and $R^{12}$ independently represent hydrogen and radicals as defined by $R^3$, or $R^4$ and $R^5$, and/or $R^{11}$ and $R^{12}$ together with the nitrogen atom to which they are bonded represent heterocycloalkyl and heteroaryl radicals, or $R^{11}$ and $R^{12}$ together with a carbon atom to which they are attached represent cycloalkyl and aryl radicals;

B represents $R^5$ and radicals represented by the formula:

wherein:

$R^7$ and $R^{7'}$ represent radicals as defined for $R^3$ and amino acid side chains selected from valine, isoleuceine, glycine, alaninc, allo-isoleucine, asparagine, leucine, glutamine and t-butylglycine;

and $R^8$ represents an amide derivative of an amino acid;

and $R^6$ represents hydrogen and alkyl radicals.

2. A compound of claim 1 represented by the formula:

or a pharmaceutically acceptable salt, prodrug or ester thereof, wherein

R² represents alkyl, aryl, cycloalkyl and aralkyl radicals;

R³ represents alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals where said substiments are selected from alkyl, aryl, aralkyl, cycloalkyl, cycloalkylalkyl, heteroaryl, heteroalkyl, heterocycloalkyl, and heterocycloalkylalkyl radicals;

R⁶ represents hydrogen and alkyl radicals;

R⁴, R⁵, R¹¹ and R¹² independently represent radicals as defined for R³ or, R⁴ and R¹¹, or R¹² together with the nitrogen atom to which they are bonded, represent pyrrolidinyl, piperidinyl, morpholinyl and piperazinyl radicals.

X' represents C(H), O and N provided that when X' is O, R¹² is absent; and

Y and Y' independently represent O and S.

3. Compound of claim 2 wherein R² represents alkyl, cycloalkylalkyl and aralkyl radicals, which radicals are optionally substituted with halogen radicals and radicals represented by the formula —OR⁹ and SR⁹ wherein R⁹ represents hydrogen and alkyl radicals.

4. Compound of claim 2 wherein R² represents alkyl, cycloalkylalkyl and aralkyl radicals.

5. Compound of claim 2 wherein R² represents alkyl radicals.

6. Compound of claim 2 wherein R² represents aralkyl radicals.

7. Compound of claim 2 wherein R² represents cycloalkylalkyl radicals.

8. Compound of claim 2 wherein R² represents $CH_3SCH_2CH_2$—, n-butyl, iso-butyl, benzyl, 2-naphthylmethyl and cyclohexylmethyl.

9. Compound of claim 2 wherein R² represents n-butyl and iso-butyl radicals.

10. Compound of claim 2 wherein R² represents benzyl and 2-naphthylmethyl.

11. Compound of claim 2 wherein R² represents n-butyl.

12. Compound of claim 2 wherein R² represents cyclohexylmethyl.

13. Compound of claim 2 wherein R³, R⁴, R⁵, R⁶, R¹¹ and R¹² independently represent alkyl, alkenyl, hydroxyalkyl, cycloalkyl, cycloalkylalkyl, heterocycloalkyl, heterocycloalkylalkyl, aryl, aralkyl, and heteroaralkyl.

14. Compound of claim 2 wherein R³, R⁴, R⁵, R⁶, R¹¹ and R¹² independently represent alkyl radicals.

15. Compound of claim 2 wherein R³, R⁴, R⁵, R⁶, R¹¹ and R¹² independently represent alkenyl radicals.

16. Compound of claim 2 wherein R³, R⁴, R⁵, R⁶, R¹¹ and R¹² independently represent hydroxyalkyl radicals.

17. Compound of claim 2 wherein R³, R⁴, R⁵, R⁶, R¹¹ and R¹² independently represent cycloalkyl and cycloalkylalkyl radicals.

18. Compound of claim 2 wherein R³, R⁴, R⁵, R⁶, R¹¹ and R¹² independently represent heterocycloalkyl and heterocycloalkylalkyl radicals.

19. Compound of claim 2 wherein R³, R⁴, R⁵, R⁶, R¹¹ and R¹² independently represent aryl and aralkyl radicals.

20. Compound of claim 2 wherein R³, R⁴, R⁵, R⁶, R¹¹ and R¹² independently represent heteroaralkyl radicals.

21. Compound of claim 2 wherein R³, R⁴, R⁵, R⁶, R¹¹ and R¹² independently represent alkyl radicals having from about 2 to about 5 carbon atoms.

22. Compound of claim 2 wherein R³, R⁴, R⁵, R⁶, R¹¹ and R¹² independently represent alkyl radicals having from about 2 to about 5 carbon atoms, cycloalkylalkyl radicals, aralkyl radicals, heterocycloalkyl radicals and heteroaryl radicals.

23. Compound of claim 2 wherein R³, R⁴, R⁵, R⁶, R¹¹ and R¹² independently represent methyl, iopropyl, i-butyl, i-amyl, t-butyl, n-butyl, neo-pentyl, benzyl, para-methoxybenzyl, para-methylbenzyl, 2-naphthylmethyl and cyclohexylmethyl radicals.

24. A pharmaceutical composition comprising a compound of claim 1 and a pharmaceutically acceptable carrier.

25. A pharmaceutical composition comprising a compound of claim 2 and a pharmaceutically acceptable carrier.

26. Method of inhibiting a retroviral protease comprising administering a protease inhibiting amount of a composition of claim 24.

27. Method of claim 26 wherein the retroviral protease is HIV protease.

28. Method for treating a retroviral infection comprising administering an effective amount of a composition of claim 24.

29. Method of claim 28 wherein the retroviral infection is an HIV infection.

30. Method for treating AIDS comprising administering an effective amount of a composition of claim 24.

31. Method of inhibiting a retroviral protease comprising administering a protease inhibiting amount of a composition of claim 25.

32. Method of claim 31 wherein the retroviral protease is HIV protease.

33. Method for treating a retroviral infection comprising administering an effective amount of a composition of claim 25.

34. Method of claim 33 wherein the retroviral infection is an HIV infection.

35. Method for treating AIDS comprising administering an effective amount of a composition of claim 25.

* * * * *